United States Patent
Kajiyama

(10) Patent No.: US 8,844,338 B2
(45) Date of Patent: Sep. 30, 2014

(54) GAS SENSOR ELEMENT AND GAS SENSOR

(75) Inventor: Norikazu Kajiyama, Kariya (JP)

(73) Assignee: Denso Corporation, Kariya (JP)

( * ) Notice: Subject to any disclaimer, the term of this patent is extended or adjusted under 35 U.S.C. 154(b) by 551 days.

(21) Appl. No.: 13/178,622

(22) Filed: Jul. 8, 2011

(65) Prior Publication Data

US 2012/0006099 A1    Jan. 12, 2012

(30) Foreign Application Priority Data

Jul. 9, 2010    (JP) .................................. 2010-157133
May 11, 2011   (JP) .................................. 2011-106436

(51) Int. Cl.
*G01N 9/00* (2006.01)
*G01N 27/407* (2006.01)
*G01N 27/12* (2006.01)

(52) U.S. Cl.
CPC ............ *G01N 27/4071* (2013.01); *G01N 27/12* (2013.01); *G01N 27/4077* (2013.01)
USPC ...................................................... 73/31.05

(58) Field of Classification Search
CPC . G01N 27/4077; G01N 27/12; G01N 27/414; G01N 27/3504
USPC ............................................................ 73/31.05
See application file for complete search history.

(56) References Cited

U.S. PATENT DOCUMENTS 6,389,877 B1 *   5/2002  Takeuchi et al. .............. 73/19.03
2008/0121020 A1 *  5/2008  Oya et al. ..................... 73/31.05

FOREIGN PATENT DOCUMENTS

JP    H08-008044     1/1996
JP    2007-292510    11/2007

OTHER PUBLICATIONS

Office Action (2 pages) dated Jun. 25, 2013, issued in corresponding Japanese Application No. 2011-106436 and English translation (2 pages).

* cited by examiner

*Primary Examiner* — Hezron E Williams
*Assistant Examiner* — Rodney T Frank
(74) *Attorney, Agent, or Firm* — Nixon & Vanderhye PC

(57) ABSTRACT

A gas sensor element of the present invention detects concentration of a specific gas within a measured gas. The gas sensor element comprises: a wiring layer formed inside a sensor; an insulating layer covering a front surface of the wiring layer; an electrode terminal provided on a main surface of the insulating layer on an opposite side of the insulating layer from the wiring layer, and electrically connected to the wiring layer; and an intermediate layer interposed between the electrode terminal and the wiring layer, and electrically connecting the electrode terminal and the wiring layer. The electrode terminal is composed of a first metal material. The wiring layer is composed of a second metal material. The intermediate layer is composed of whichever of the first metal material and the second metal material has the lower melting point.

10 Claims, 34 Drawing Sheets

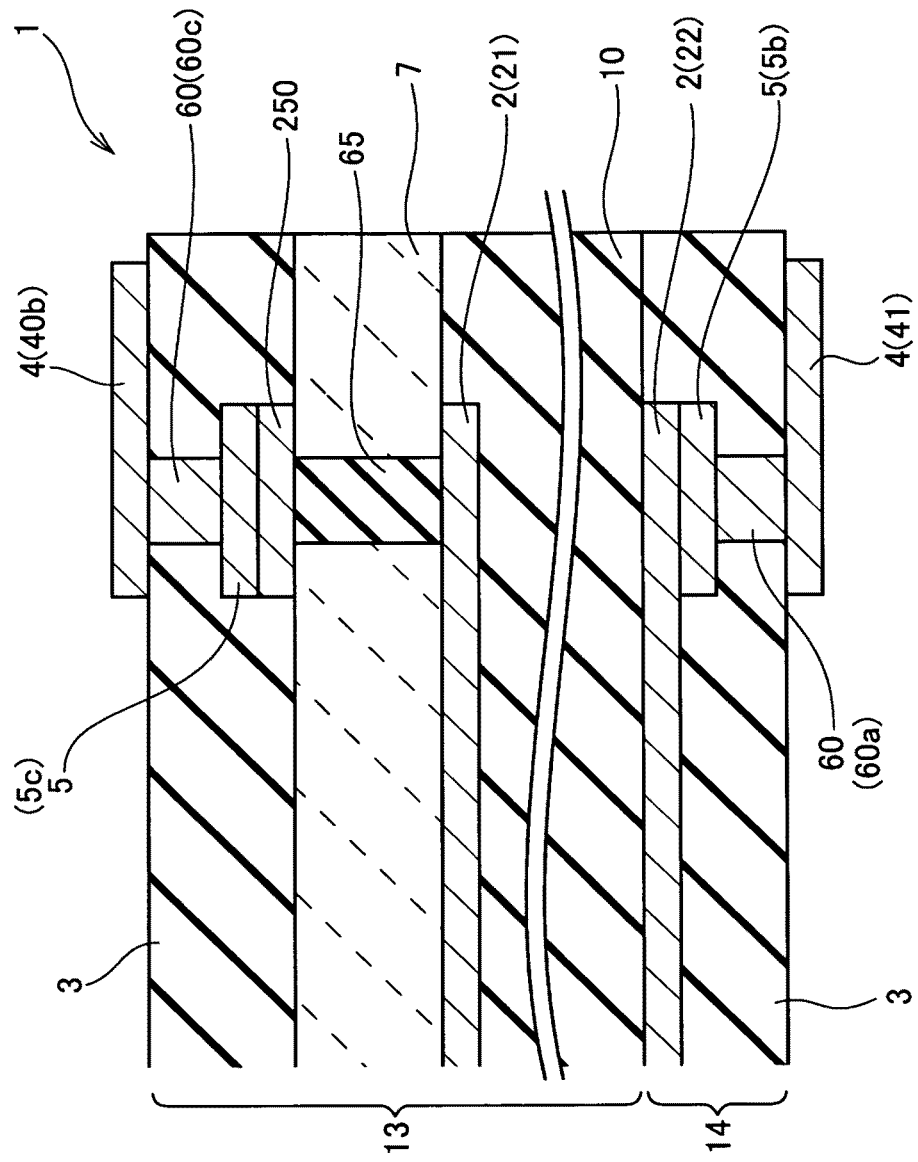

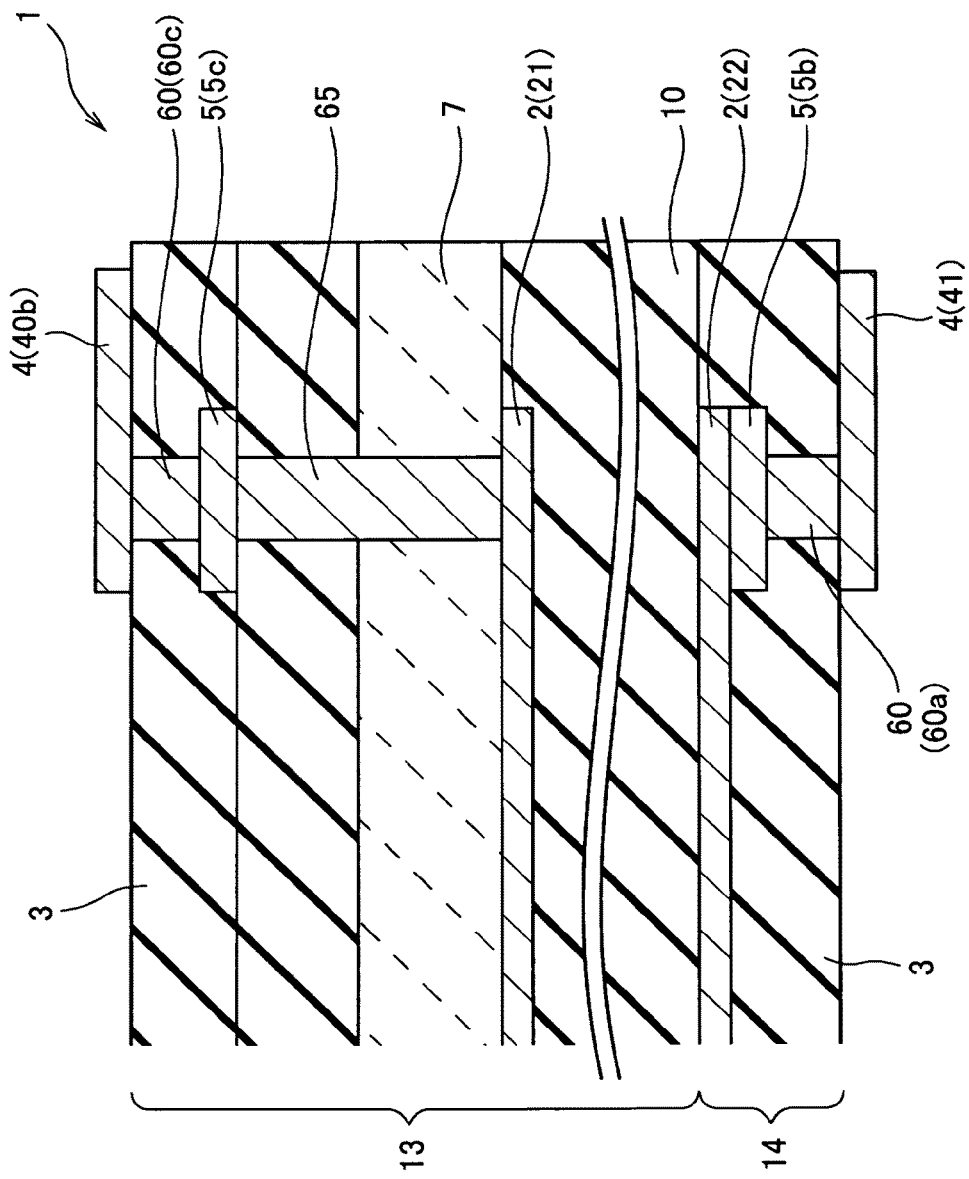

GAS SENSOR ELEMENT AND GAS SENSOR

CROSS REFERENCE TO RELATED APPLICATION

This application is based upon and claims the benefit of priority from the prior Japanese Patent Application Nos. 2010-157133 filed Jul. 9, 2010 and 2011-106436 filed May 11, 2011, the entire contents of which is incorporated herein by reference.

BACKGROUND OF THE INVENTION

1. Field of the Invention

The present invention relates to a gas sensor element for detecting concentration of a specific gas within a measured gas, and a gas sensor including the gas sensor element.

2. Description of the Related Art

Gas sensors are widely used for detecting leakage of combustible gas serving as fuel and detecting gas included in exhaust gas. To measure oxygen gas concentration within exhaust gas, solid electrolyte sensors that detect electromotive force attributed to a specific gas and in which a battery is composed of ionic conductors have been used since the past.

For example, Japanese Unexamined Patent Publication H08-8044 discloses a gas sensor element included in a gas sensor shown in FIG. 1. As shown in FIG. 1, a gas sensor element 91 includes a solid electrolyte body 97 having oxygen ion conductivity, a wiring layer 92 formed on both main surfaces of the solid electrolyte body 97, and an insulating layer 93 layered on one main surface 970 of the solid electrolyte body 97.

An electrode terminal 94 for connecting to an external device is formed on a surface of the insulating layer 93. An intermediate layer 95 is interposed between the electrode terminal 94 and the wiring layer 92. A through hole 96 is formed in the insulating layer 93, and a metal connecting member 96a is provided within the through hole 96. The electrode terminal 94 and the wiring layer 92 are electrically connected by the connecting member 96a and the intermediate layer 95.

The gas sensor element 91 includes a heater section 980 for heating the solid electrolyte body 97. The heater section 980 includes the wiring layer 92, the insulating layer 93, the heater connecting member 911, the intermediate layer 95, the connecting member 96a, and the electrode terminal 94. A heater connecting member 911 is interposed between the wiring layer 92 and the intermediate layer 95. Furthermore, a heating element (not shown) is connected to the wiring layer 92.

The gas sensor element 91 is used in a state heated by the heater section 980. Therefore, as a result of the overall section (the wiring layer 92, the intermediate layer 95, the connecting member 96a, the electrode terminal 94, and the heater connecting member 911) being composed of a metal material of which the main component is platinum, the gas sensor element 91 is capable of withstanding high temperature environments.

However, because the heater section 980 in the conventional gas sensor element 91 is composed of a metal material of which the main component is platinum, manufacturing cost is high. Therefore, a gas sensor element 91 capable of being manufactured at a low cost is desired.

As shown in FIG. 2, an attempt has been made to reduce manufacturing cost of the gas sensor element 91 by forming the wiring layer 92 from palladium that is less expensive than platinum (Pt). When the gas sensor element 91 is manufactured, as shown in FIG. 2, the insulating layer 93, the wiring layer 92, the solid electrolyte body 97, and the like are stacked and subsequently fired. Because the wiring layer 92 (palladium) and the intermediate layer 95 (platinum) are composed of differing materials, when fired, platinum and palladium alloy is formed on an interface 99 between the wiring layer 92 and the intermediate layer 95. In accompaniment with the alloying, metal in the periphery moves towards the interface 99. Because palladium has a lower melting point than platinum, when fired, palladium moves to the interface 99 before platinum as shown in FIG. 3. As a result, a void 90 is formed in the wiring layer 92, causing disconnection in the wiring layer 92 in some instances. Electrical resistance between the electrode terminal 94 and the wiring layer 92 becomes high. Therefore, temperature rise in the gas sensor element 91 becomes insufficient and electrical resistance in the gas sensor increases. As a result, detection accuracy of the gas sensor element 91 may decrease. Alternatively, the gas sensor element 91 may become unable to perform detection.

Furthermore, the electrode terminal 94 and the wiring layer 92 are used within a wide temperature range, such as from −40° C. to 1000° C. Therefore, when the electrode terminal 94 and the wiring layer 92 are formed using metal materials having differing coefficients of thermal expansion, stress occurs as a result of the difference in thermal expansion, and disconnection may occur in the wiring layer 92. Electrical resistance between the electrode terminal 94 and the wiring layer 92 becomes high. As a result, as described above, detection accuracy of the gas sensor element 91 may decrease. Alternatively, the gas sensor element 91 may become unable to perform detection.

SUMMARY OF THE INVENTION

The present invention has been achieved in light of the above-described issues. An object of the present invention is to provide a gas sensor element having high connection reliability between a wiring layer and an electrode terminal and high detection accuracy, and a gas sensor including the gas sensor element.

A first aspect of the invention is a gas sensor element that detects concentration of a specific gas within a measured gas, the gas sensor element comprising: a wiring layer formed inside a sensor; an insulating layer covering a front surface of the wiring layer; an electrode terminal provided on a main surface of the insulating layer on an opposite side of the insulating layer from the wiring layer, and electrically connected to the wiring layer; and an intermediate layer interposed between the electrode terminal and the wiring layer, and electrically connecting the electrode terminal and the wiring layer, wherein the electrode terminal is composed of a first metal material, the wiring layer is composed of a second metal material, and the intermediate layer is composed of whichever of the first metal material and the second metal material has the lower melting point.

In the present, the electrode terminal is composed of the first metal material, the wiring layer is composed of the second metal material, and the intermediate layer is composed of whichever of the first metal material and the second metal material has the lower melting point. In a manufacturing process of the gas sensor element, when a firing procedure is performed, the metal material forming the intermediate layer and the metal material differing from that of the intermediate layer alloy are in contact. The metal material in the peripheral portion of the intermediate layer having a low melting point may move, thereby forming a void in the peripheral portion of the intermediate layer. However, because the peripheral portion of the intermediate layer does not directly contribute to electrical connection, defects, such as increase in electrical resistance, do not easily occur even when a void is formed.

Furthermore, when the electrode terminal and the wiring layer are composed of metal materials having differing coefficients of thermal expansion, stress attributed to difference in thermal expansion in a usage environment may occur. In this instance as well, defects, such as disconnection in the wiring layer, do not easily occur because the intermediate layer is formed. As a result, connection reliability between the electrode terminal and the wiring layer can be increased.

In addition, the gas sensor element suppresses increase in electrical resistance between the wiring layer (heater wiring) disposed on the heater side and the electrode terminal. Therefore, sufficient current can be sent through the heater wiring, and the temperature of the gas sensor element can be sufficiently increased. As a result, detection accuracy of the gas sensor element can be increased.

A second aspect of the invention is a gas sensor including the above-described gas sensor element.

According to the second aspect of the invention, because the gas sensor element is included, a gas sensor having high connection reliability between the wiring layer and the electrode terminal, and high detection accuracy can be achieved.

BRIEF DESCRIPTION OF THE DRAWINGS

The invention will be more particularly described with reference to the accompanying drawings in which:

FIG. 4 is a cross-sectional view of a gas sensor element before firing according to a first embodiment of the present invention, and is a cross-sectional view of a first sensor element 40a shown in FIG. 6 taken along a line parallel to the paper on which

FIG. 5 is a cross-sectional view of the gas sensor element before firing according to a first embodiment of the present invention, and is a cross-sectional view of a second sensor element 40b shown in FIG. 6 taken along a line parallel to the paper on which FIG. 6 is printed;

FIG. 6 is an exploded perspective view of the gas sensor element according to a first embodiment of the present invention;

FIG. 36 is a cross-sectional view of a gas sensor element passing through a second sensor electrode 40*b* before firing according to a nineteenth embodiment of the present invention; and FIG. 37 is a cross-sectional view of a gas sensor element passing through a second sensor electrode 40*b* before firing according to a twentieth embodiment of the present invention.

DETAILED DESCRIPTION OF THE PREFERRED EMBODIMENTS

A gas sensor element according to the embodiments of the present invention will be described using each embodiment with reference to the drawings.

First Embodiment

FIG. 4 to FIG. 15 and Table 1 to Table 5

A gas sensor element according to a first embodiment of the present invention will be described with reference to FIG. 4 to FIG. 8 and Example 1.

Figure 4:
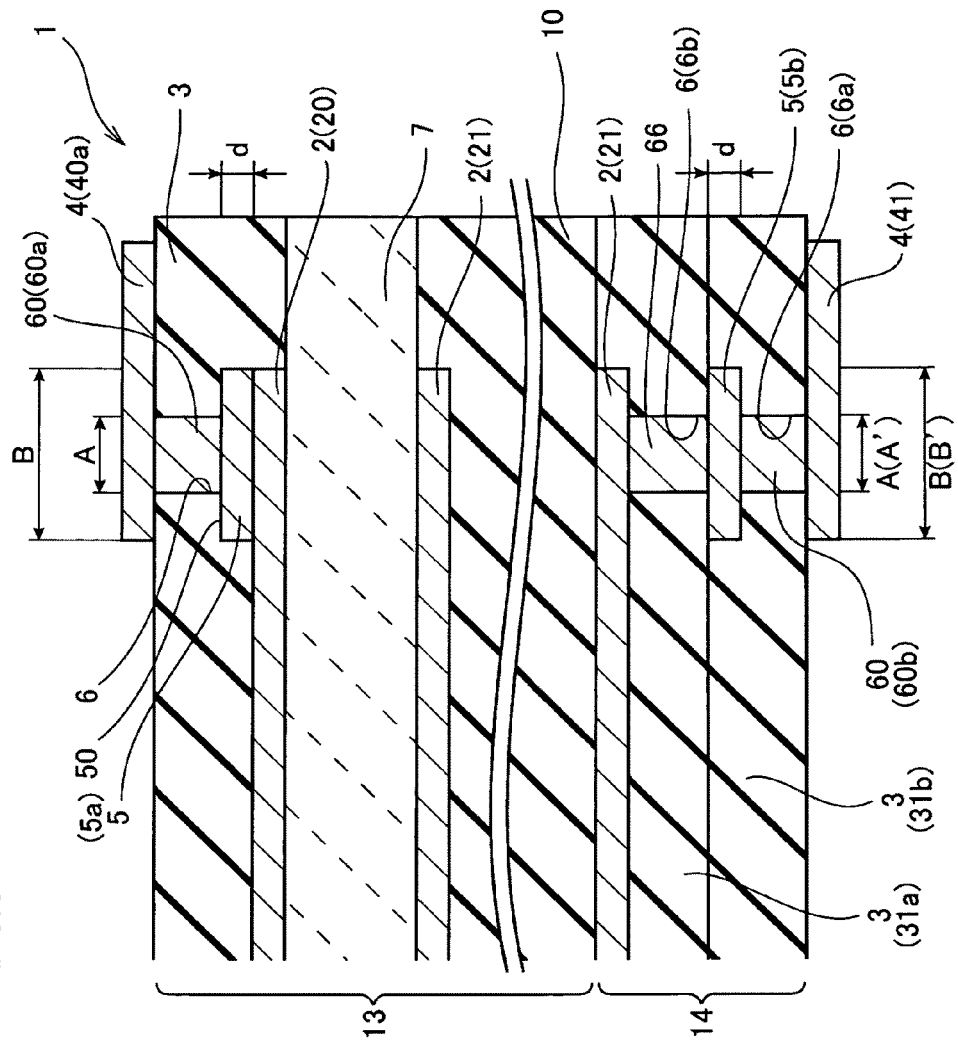

FIG. 4 is a cross-sectional view of a gas sensor element 1 before firing. As shown in FIG. 4, in the gas sensor element 1, a wiring layer 2 is disposed within a sensor section 13, and the surface of the wiring layer 2 is covered by an insulating layer 3. An electrode terminal 4 is disposed on a main surface of the insulating layer 3 on the opposite side of the insulating layer 3 from the wiring layer 2. An intermediate layer 5 is interposed between the electrode terminal 4 and the wiring layer 2, and the electrode terminal 4 is electrically connected to the wiring layer 2.

The electrode terminal 4 is composed of a first metal material. The wiring layer 2 is composed of a second metal material. The intermediate layer 5 is composed of whichever of the first metal material and the second metal material has the lower melting point.

Figure 6:
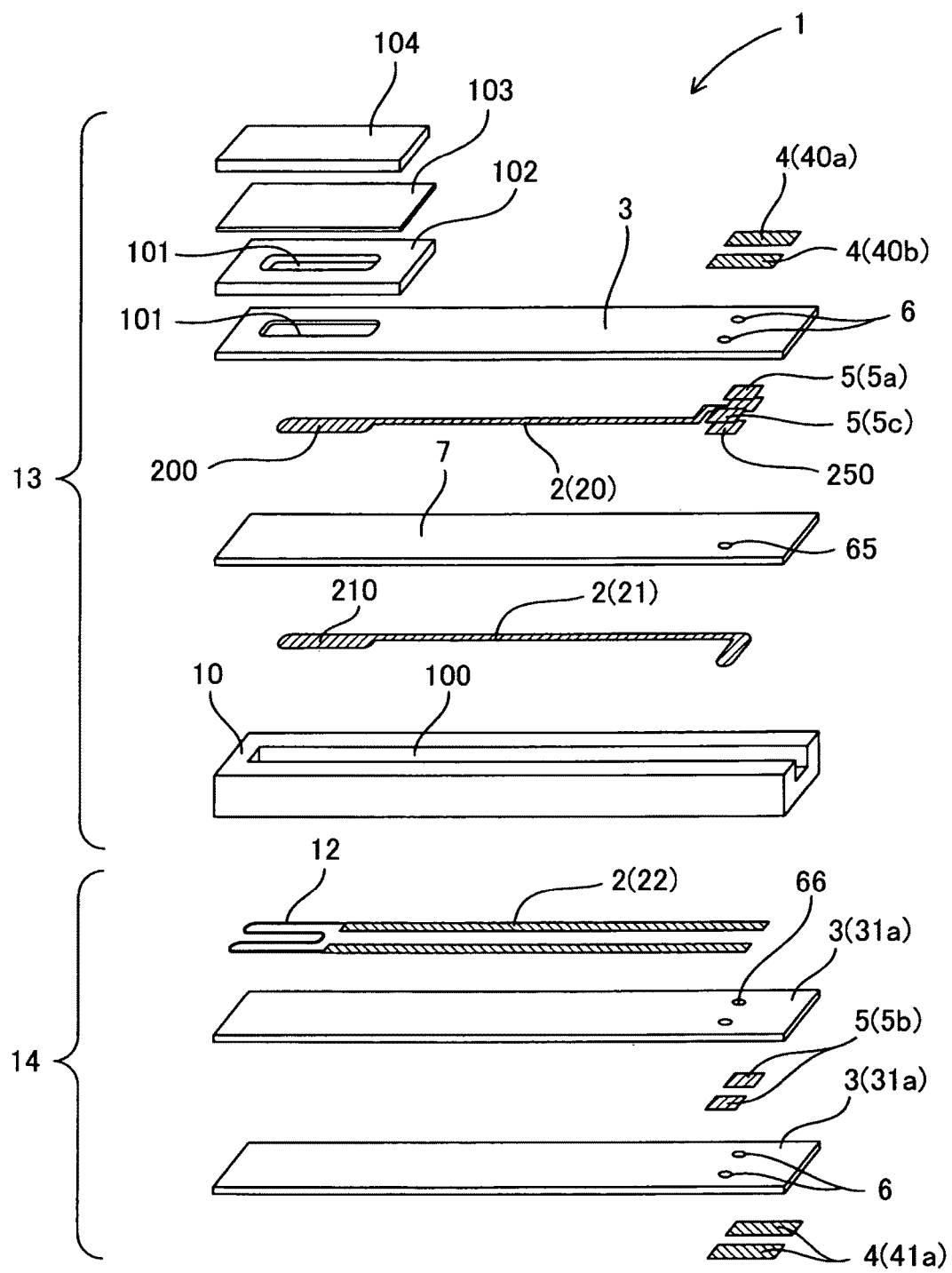
FIG. 6 is printed.

More specifically, as shown in FIG. 6, the gas sensor element 1 is configured by a sensor section 13 and a heater section 14.

The sensor section 13 is configured by a shielding layer 104, a diffusion resistance layer 103, a spacer layer 102, an insulating layer 3, a solid electrolyte body 7, and a duct formation layer 10 being stacked. The wiring layer 2 (measured gas side wiring 20 and reference gas side wiring 21) is formed on both main surfaces of the solid electrolyte body 7. The intermediate layer 5 is interposed between the wiring layer 2 and the electrode terminal 4. The electrode terminal 4 is configured by a first sensor electrode 40*a* and a second sensor electrode 40*b*. The first sensor electrode 40*a* is connected to the measured gas side wiring 20. The second sensor electrode 40*b* is connected to the reference gas side wiring 21.

Figure 7:
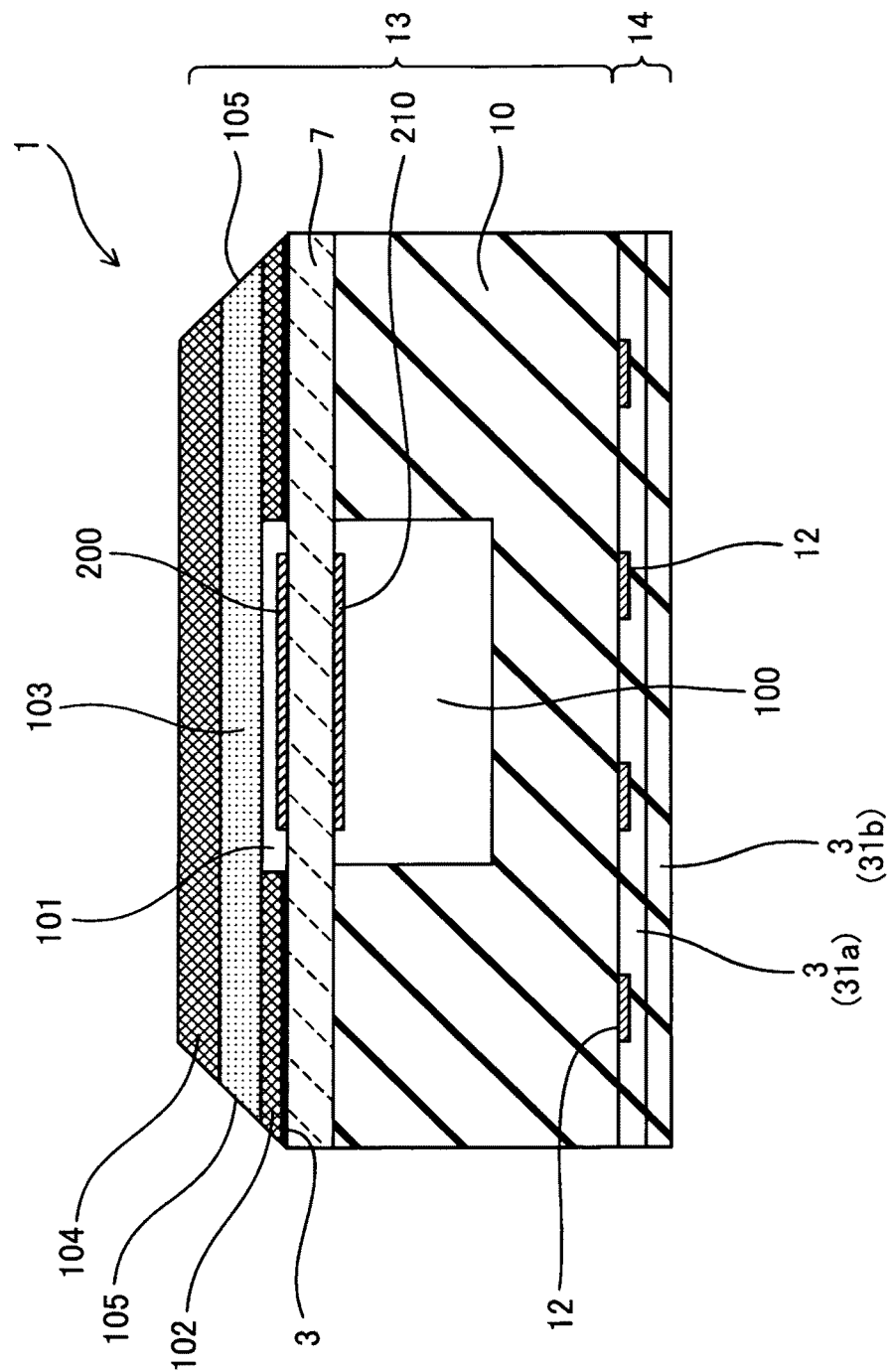
FIG. 7 is a cross-sectional view of a tip end section of a gas sensor according to a first embodiment of the present invention.

As shown in FIG. 6 and FIG. 7, a measured gas chamber 101 for introducing the measured gas (such as exhaust gas) is formed in the spacer layer 102 and the insulating layer 3. A reference gas chamber 100 for introducing reference gas (atmosphere) is formed in the duct formation layer 10.

A measured gas side electrode 200 is formed at the tip end of the measured gas side wiring 20. A reference gas side electrode 210 is formed at the tip end of the reference gas side wiring 21. The measured gas side electrode 200 is exposed within the measured gas chamber 101. The reference gas side electrode 210 is exposed within the reference gas chamber 100.

The solid electrolyte body 7 has oxygen ion conductivity. Therefore, when a voltage is applied between the reference gas side electrode 210 and the measured gas side electrode 200, a current corresponding to the difference in oxygen concentration between the reference gas and the measured gas flows between the reference gas side electrode 210 and the measured gas side electrode 200. The oxygen concentration within the measured gas is detected by the current value being measured.

The heater section 14 includes a heating element 12, a wiring layer 2 (heater wiring 22) connected to the heating element 12, two insulating layers 3 (first heater substrate 31*a* and second heater substrate 31*b*), and an electrode terminal 4 (heater electrode 41). An intermediate layer 5 is interposed between the two insulating layers 3.

As shown in FIG. 4, in the sensor section 13 of the gas sensor element 1 according to the first embodiment, a through hole 6 is provided that passes through the insulating layer 3, and connects an intermediate layer 5*a* and the electrode terminal 4. The through hole 6 has a smaller outer diameter than the intermediate layer 5*a*. A metal connecting member 60*a* is disposed within the through hole 6.

In the heater section 14, a first through hole 6*a* is provided that passes through the second heater substrate 31*b*, and connects an intermediate layer 5*b* and the heater electrode 41. The through hole 6*a* has a smaller outer diameter than the intermediate layer 5*b*. A metal first connecting member 60*b* is disposed within the through hole 6*a*. In addition, a second through hole 6*b* is provided that passes through the first heater substrate 31*a*, and connects the wiring layer 22 and the intermediate layer 5*b*. The second through hole 6*b* has a smaller outer diameter than the intermediate layer 5*b*. A metal second connecting member 66 is disposed within the second through hole 6*b*.

The first sensor electrode 40*a* and the connecting member 60*a* of the sensor section 13 are composed of the first metal material. The intermediate layers 5*a* and 5*b*, the measured gas side wiring 20, and the reference gas side wiring 21 are composed of the second metal material having a lower melting point than the first metal material.

The heater electrode 41 and the first connecting member 60*b* of the heater section are composed of the first metal material. The heater wiring 22, the second connecting member 66, and the intermediate layer 5*b* are composed of the second metal material.

The first metal material and the second metal material contain at least one material selected from Mg, Al, Sc, V, Cr, Mn, Fe, Co, Ni, Cu, Zn, Ga, Nb, Mo, Ru, Rh, Pd, Ag, In, Sn, W, Re, Os, Ir, Pt, Au, and Pb. The first metal material and the second metal material also contain at least one type of ceramic, such as alumina, zirconia, and yttria. As a result of the ceramic being added to the first metal material and the second metal material in this way, bonding between the insulating layer 3, the solid electrolyte body 7 and the like, and the first metal material and the second metal material can be increased. A weight ratio of ceramic/metal in the first metal material and the second metal material is 1% wt to 25% wt.

More preferably, the first metal material and the second metal material contain at least one of Pt and Pd, and at least one type of ceramic such as alumina, zirconia, and yttria. The weight ratio of ceramic/metal in the first metal material and the second metal material is preferably 1% wt to 25% wt. As a result of a composition such as this, the melting point of the first metal material and the second metal material becomes 1500° C. or higher. Therefore, even when the gas sensor element 1 is fired at a high temperature (such as 1450±50° C.) during manufacturing, the risk of the metal materials melting is reduced. In addition, the coefficients of thermal expansion of the first metal material and the second metal material become close to the coefficient of thermal expansion $9.2 \times 10^{-6}/°$ C. of the solid electrolyte body 7. Therefore, occurrence of large thermal stress between the metal materials and the solid electrolyte body 7 during firing can be suppressed.

Figure 5:
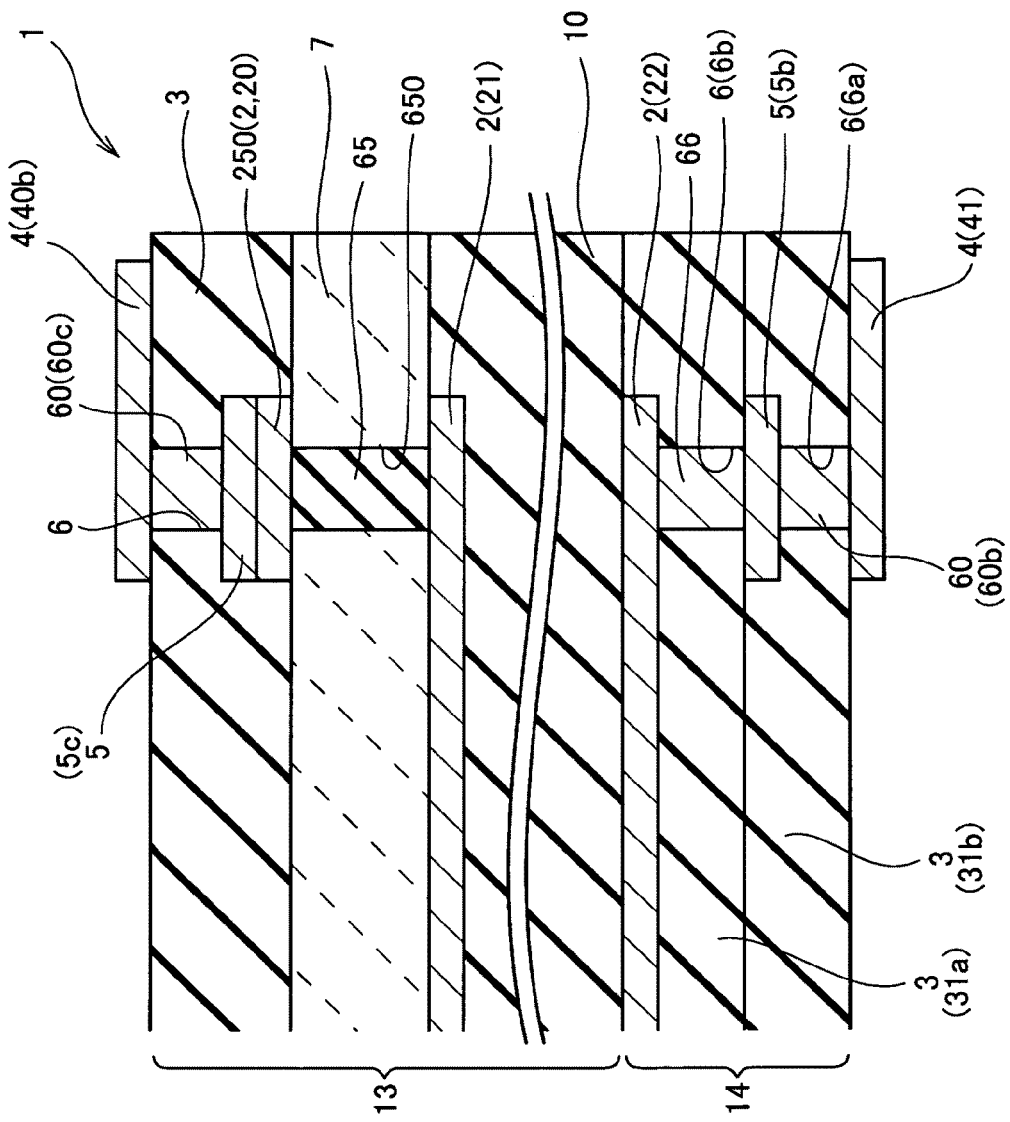

Furthermore, as shown in FIG. 5, a through hole 650 is formed in the solid electrolyte body 7. A metal sensor side second connecting member 65 is disposed within the through hole 650. A connecting layer 250 is formed by the wiring layer 2 configuring the measured gas side wiring 20. The second sensor electrode 40b and the reference gas side wiring 21 are electrically connected by the connecting layer 250, adjacent intermediate layer 5c and sensor side second connecting member 65, and the sensor side first connecting member 60c adjacent to the intermediate layer 5c. Here, the second sensor electrode 40b and the sensor side first connecting member 60c are composed of the first metal material. The intermediate layer 5c, the connecting layer 250, the sensor side second connecting member 65, and the reference gas side wiring 21 are composed of the second metal material having a lower melting point than the first metal material.

The intermediate layer 5 and the through hole 6 have a circular shape when viewed from an axial line direction. An outer diameter A of the through hole 6 (see FIG. 4) is 0.01 mm≤A≤1.315 mm. An outer diameter B of the intermediate layer 5 is 0.02 mm≤B≤2.63 mm. A relationship B/A≥2 is established between the outer diameter A of the though hole 6 and the outer diameter B of the intermediate layer 5. A thickness d of the intermediate layer 5 is 0.01 mm≤d≤0.1 mm.

The outer diameter A of the through hole 6 is set to 0.01 mm or more because detection accuracy of the gas sensor cannot be sufficiently ensured when the outer diameter A is less than 0.01 mm.

The outer diameter B of the intermediate layer 5 is set to 2.63 mm or less because, when the outer diameter B of the intermediate layer 5 exceeds 2.63 mm, because sensor element width is 5.28 mm, adjacent intermediate layers 5 connect with each other and short-circuit. Conductivity cannot be ensured, and detection accuracy of the gas sensor element 1 decreases.

As a result of the relationship B/A≥2 being established, an upper limit value of the outer diameter A of the through hole 6 is set to 1.315 mm from an upper limit value (2.63 mm) of the outer diameter B of the intermediate layer 5. A lower limit value of the outer diameter B of the intermediate layer 5 is set to 0.02 mm from a lower limit value (0.01 mm) of the outer diameter A of the through hole 6.

The thickness d of the intermediate layer 5 is set to 0.01 mm or more because a void is formed in an area other than the periphery of the intermediate layer 5 when the thickness d is less than 0.01 mm. On the other hand, when the thickness d of the intermediate layer 5 exceeds 0.1 mm, in terms of manufacturing the gas sensor element 1, the shape of the gas sensor element 1 becomes defective as a result of the thickness of the intermediate layer 5. Conductivity cannot be ensured, and sensor detection cannot be performed.

In this way, the relationship B/A≥2 is established between the outer diameter A of the through hole 6 and the outer diameter B of the intermediate layer 5. In addition, the thickness d of the intermediate layer 5 is 0.01 mm or more. As a result, because the outer diameter A of the intermediate layer 5 is sufficiently large and the thickness d of the intermediate layer 5 is sufficiently thick, a void V can be formed in only a peripheral portion 50 of the intermediate layer 5. As a result, formation of the void V in the interface 500 between the intermediate layer 5 and the connecting member 60 is eliminated, and increase in electrical resistance between the electrode terminal 4 and the wiring layer 2 can be suppressed.

Furthermore, as shown in FIG. 7, the side surfaces of a shielding layer 104, the diffusion resistance layer 103, and the spacer layer 102 are formed having a tapered shape. The diffusion resistance layer 103 is composed of a porous body allowing the measured gas to pass through the diffusion resistance layer 103. Therefore, the side surface of the diffusion resistance layer 103 serves as a gas inlet 105 for introducing the measured gas.

The measured gas enters into the diffusion resistance layer 103 from the gas inlet 105 and is introduced into the measured gas chamber 101.

Operational effects of the gas sensor element 2 according to the first embodiment will be described below.

Figure 8:
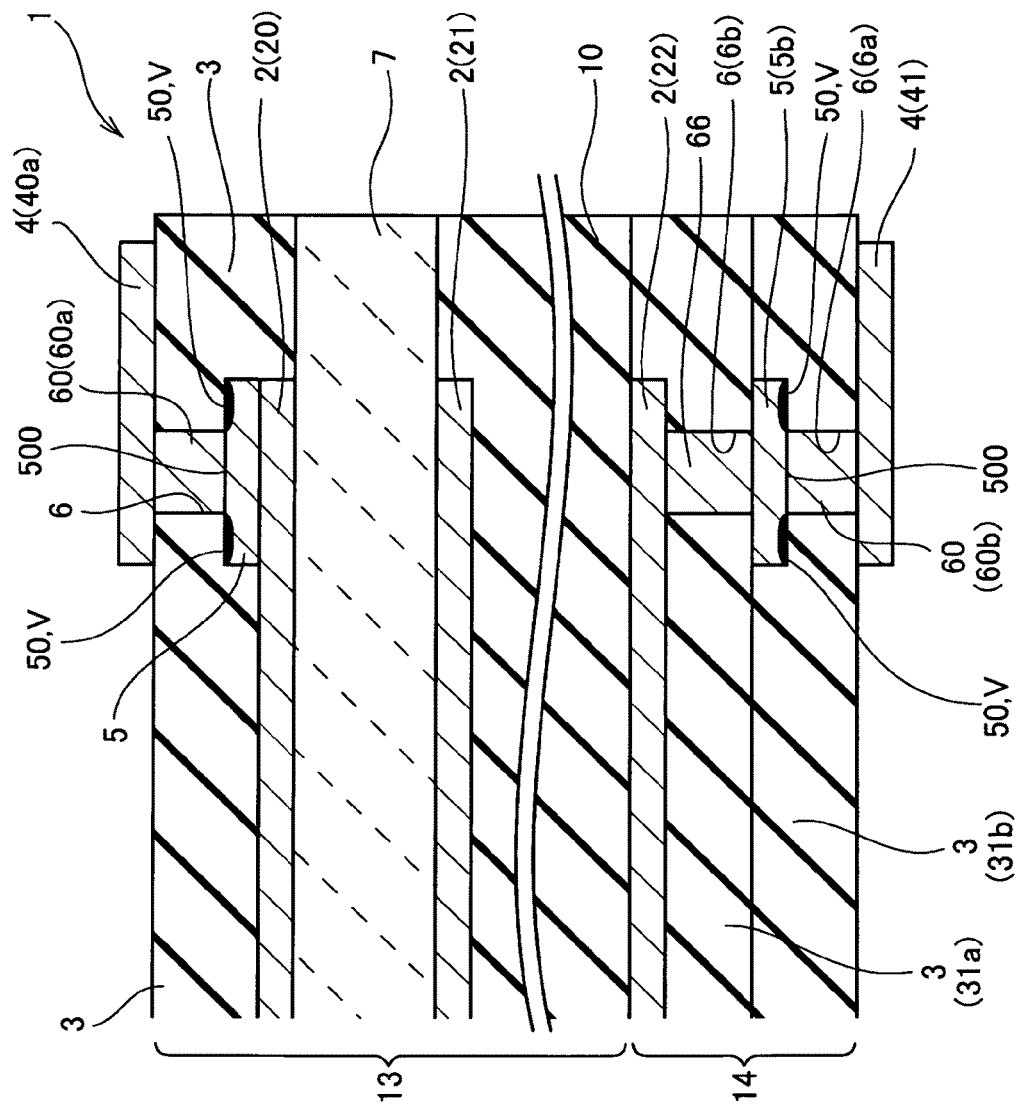
FIG. 8 is a cross-sectional view of the gas sensor element after firing according to a first embodiment of the present invention.

In the gas sensor element 1 according to the first embodiment, as shown in FIG. 4, the electrode terminal 4 is composed of the first metal material. The wiring layer 2 is composed of the second metal material. The intermediate layer 5 is composed of the second metal material having a lower melting point than the first metal material. Therefore, when firing is performed in the manufacturing process of the gas sensor element 1, as shown in FIG. 8, the second metal material configuring the intermediate layer 5 and the first metal material in contact with the intermediate layer 5 become alloyed. With the alloying of the metal materials, the metal material of the peripheral portion 50 of the intermediate layer 5 composed of the second metal material with the low melting point moves, forming a void in the peripheral portion 50 of the intermediate layer 5. In other words, the void is formed as a result of an interface where differing metal materials come into contact being alloyed by heat during ceramic firing. Metal atoms move from the periphery towards the interface, thereby forming the void. However, the peripheral portion 50 of the intermediate layer 5 in which the void is formed is an area in which current does not flow and does not directly contribute to electrical connection. Therefore, even when the void V is formed in the peripheral portion 50 of the intermediate layer 5, electrical resistance between the electrode terminal 4 and the wiring layer 2 does not significantly change.

As a result of the void being formed in the peripheral portion 50 of the intermediate layer 5 by intentionally moving the metal atoms from the peripheral portion 50 of the intermediate layer 5 in this way, movement of metal atoms from the connecting members and the wiring layer 2 can be suppressed. Because the connecting members and the wiring layer 2 are sections directly contributing to electrical connection, increase in electrical resistance is suppressed by preventing the formation of voids. Connection reliability between the electrode terminal 4 and the wiring layer 2 is improved.

In addition, in the gas sensor element 1 according to the first embodiment, the increase in electrical resistance between the heater wiring 22 and the heater electrode 41 can be suppressed. Therefore, sufficient current can be sent to the heater wiring 22. As a result of the temperature of the gas sensor element 1 being sufficiently increased, detection accuracy of the gas sensor element 1 can be increased.

In the gas sensor element 1 according to the first embodiment, as shown in FIG. 4, because the electrode terminal 4 and the intermediate layer 5 are connected by the connecting member 60a having a smaller outer diameter than the intermediate layer 5, the connecting member 60a does not come into contact with the peripheral portion 50 of the intermediate layer 5. Therefore, when firing is performed, because the intermediate layer 5 is composed of a material with a low melting point, as shown in FIG. 8, the movement of the metal material of the peripheral portion 50 of the intermediate layer 5 to a center portion (portion in contact with the connecting member 60a) is facilitated. Therefore, as a result of the void being formed in the peripheral portion 50 of the intermediate layer 5 that is the periphery of the interface 500 with the intermediate layer 5 that is in contact with the connecting member 60a, connection reliability between the electrode terminal 4 and the wiring layer 2 is improved.

Furthermore, in the gas sensor element 1 according to the first embodiment, as shown in FIG. 4, in the heater section 14, the wiring layer 22 and the electrode terminal 41 are connected by the first connecting member 60b and the second connecting member 66 having a smaller outer diameter than the intermediate layer 5b. Therefore, because the first connecting member 60b and the second connecting member 66 having a smaller outer diameter than the intermediate layer 5b are connected to the intermediate layer 5b, the first connecting member 60b and the second connecting member 66 do not come into contact with the peripheral portion 50 of the intermediate layer 5b. Because the intermediate layer 5b is composed of a metal material having a low melting point, when firing is performed, as shown in FIG. 8, the movement of the metal material of the peripheral portion 50 of the intermediate layer 5b to the center is facilitated. Therefore, the void is formed in the peripheral portion 50 of the intermediate layer 5b. Here, the peripheral portion 50 means the portion of the intermediate layer 5b except for the interface 500 with the intermediate layer 5b in contact with the connecting members 60b and 66. As a result, connection reliability between the electrode terminal 41 and the wiring layer 23 is improved, and detection accuracy of the gas sensor element 1 increases.

As described above, according to the first embodiment, a gas sensor element having high connection reliability between a wiring layer and an electrode terminal and high detection accuracy can be achieved.

Hereafter, experiments were conducted to confirm the effects of the gas sensor element of the present invention using Example 1.

Example 1

In Example 1, a sample was manufactured having the same structure as the gas sensor element 1 according to the first embodiment (FIG. 4 and FIG. 5) by stacking the electrode terminal 4, the insulating layer 3, the intermediate layer 5, and the like. Here, the sensor electrode 40, the heater electrode 41, and the connecting members 60a and 60b were formed using the first metal material. The intermediate layer 5a and 5b, the wiring layers 20, 21, and 22, and the second connecting member 66 were formed using the second metal material having a lower melting point than the first metal material.

Specifically, a following material was used as the first metal material. The material contains 100% Pt as the metallic component, and has a melting point of 1774° C. and a coefficient of linear expansion of $9.1 \times 10^{-6}$/° C. The material uses alumina as the ceramic. The weight ratio of alumina/Pt=10 wt %. A following material was used as the second metal material. The material contains 100% Pd as the metallic component, and has a melting point of 1555° C. and a coefficient of linear expansion of $1.176 \times 10^{-5}$/° C. The material uses alumina as the ceramic. The weight ratio of alumina/Pd=10 wt %. Similar materials were also used in embodiments described hereafter.

Each dimension is as follows. The thickness of the electrode terminal 4 (40 and 41) is 0.02 mm. The height of the connecting member 60 is 0.16 mm. The thickness d of the intermediate layers 5a and 5b is 0.03 mm. The respective thicknesses of the wiring layers 20, 21, and 22 are 0.01 mm, 0.018 mm, and 0.03 mm. The outer diameters A and A' of the connecting member 60 are 0.248 mm. The outer diameter B of the intermediate layer 5a is 0.6 mm. The outer diameter B' of the intermediate layer 5b is 0.5 mm. The thickness of the insulating layer 3 of the sensor section 13 is 0.2 mm. The thickness of the first heater substrate 31a is 0.19 mm. The thickness of the second heater substrate 31b is 0.19 mm. As a result, Sample 1 before firing of the gas sensor element 1 of the present invention was obtained.

Figure 1:
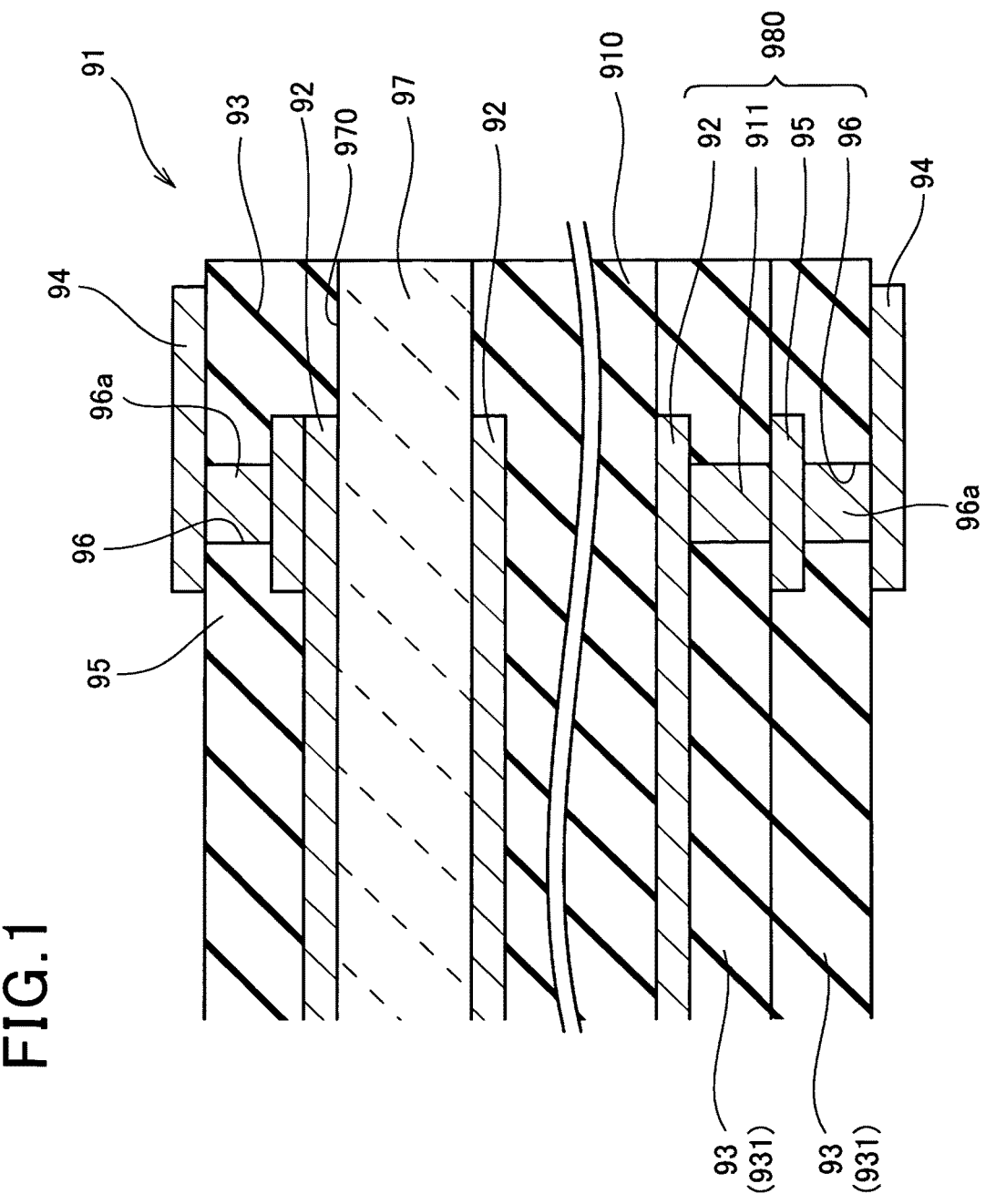
FIG. 1 is a cross-sectional view of a gas sensor element in a conventional example.
Figure 2:
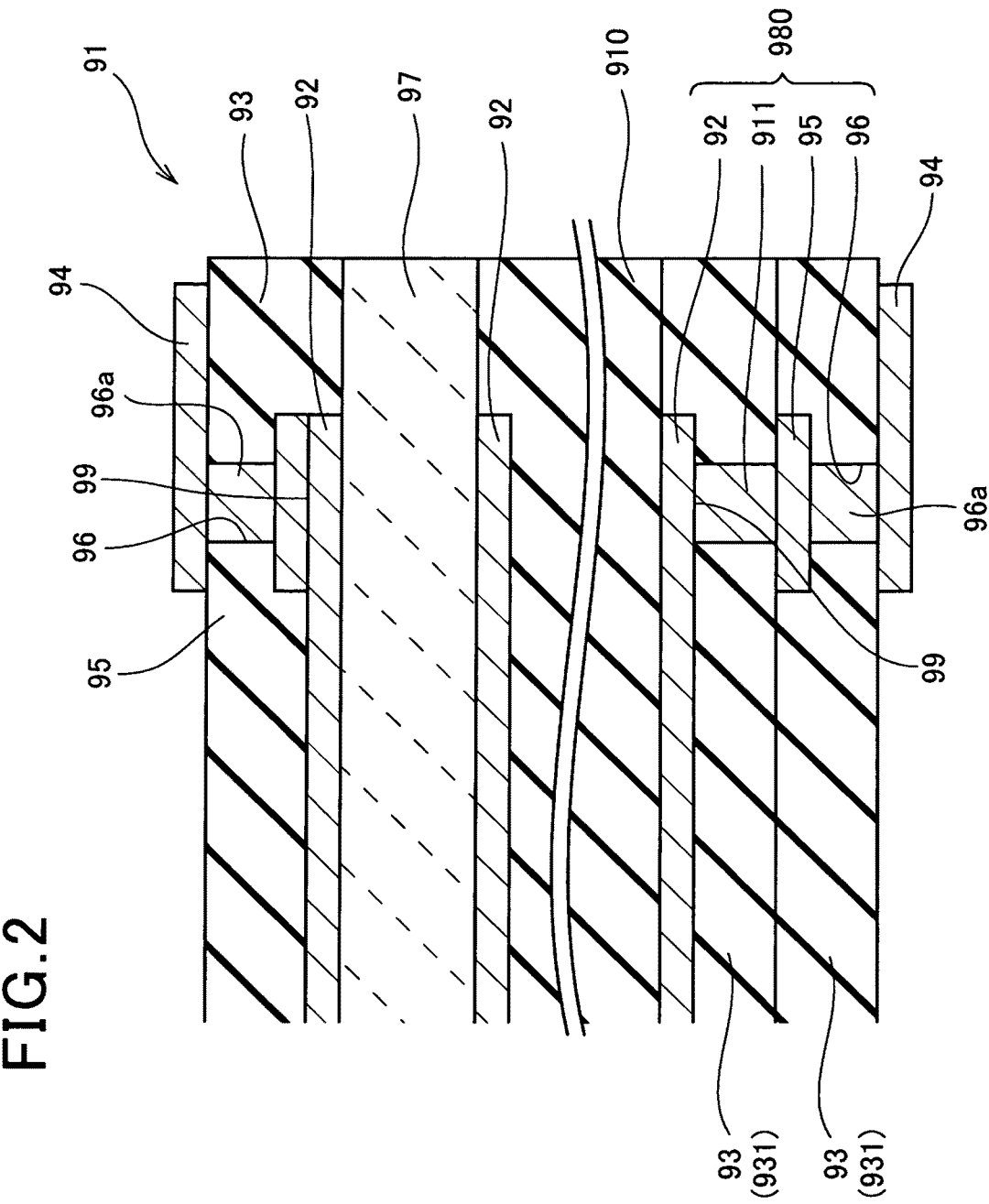
FIG. 2 is a cross-sectional view of a gas sensor in a conventional example in which only a wiring layer is composed of a different metal material, and shows a state before firing.
Figure 3:
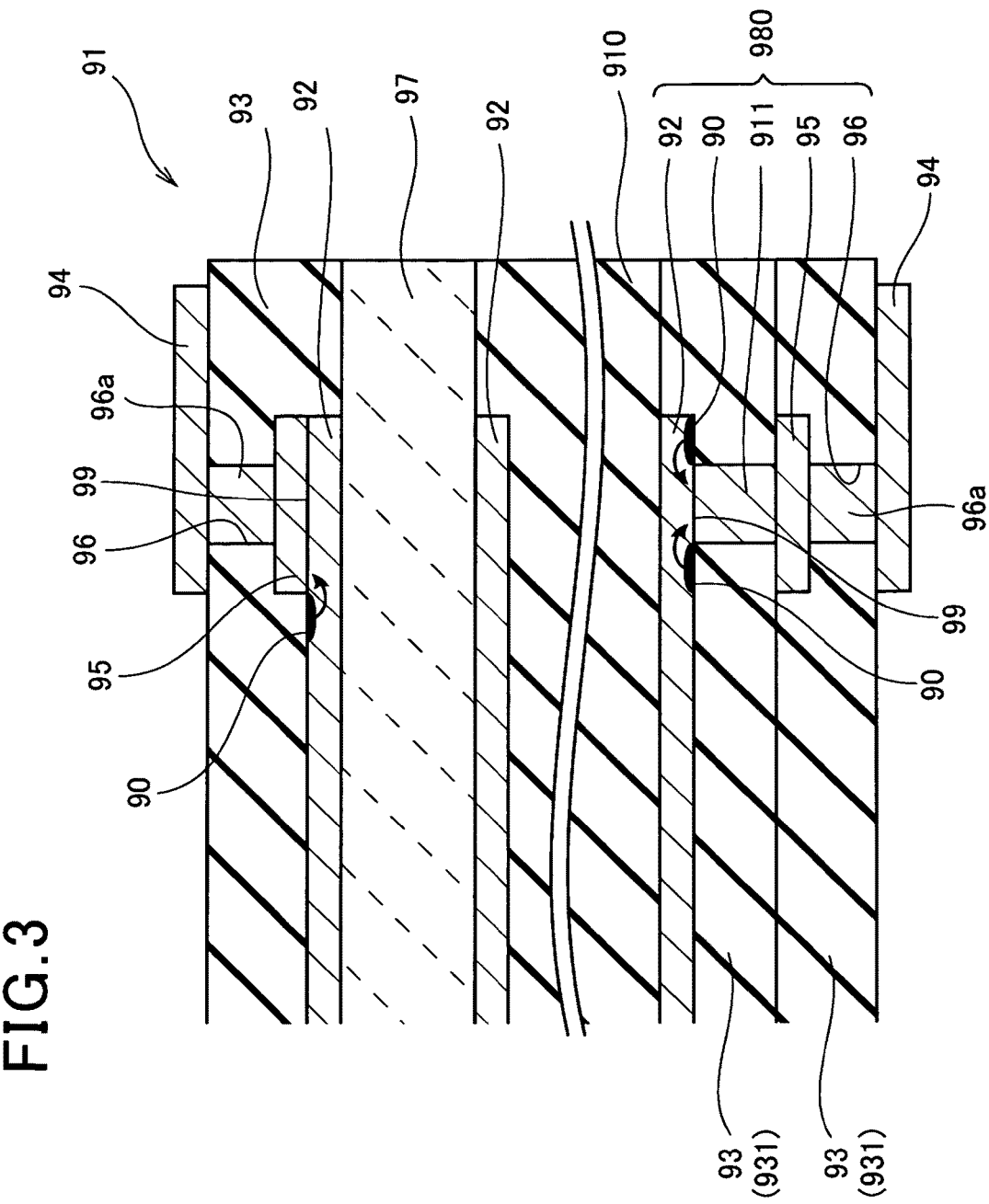
FIG. 3 is a cross-sectional view of the gas sensor shown in FIG. 2, and shows a state after firing.

As a comparative example, Sample 2 before firing was manufactured (see FIG. 3) in which the sensor electrode 40, the heater electrode 41, the connecting members 60a and 60b, the intermediate layers 5a and 5b, and the second connecting member 66 are composed of the first metal material. The wiring layers 20, 21, and 22 are composed of the second metal material. Other structures are similar to those of Sample 1.

Figure 9:
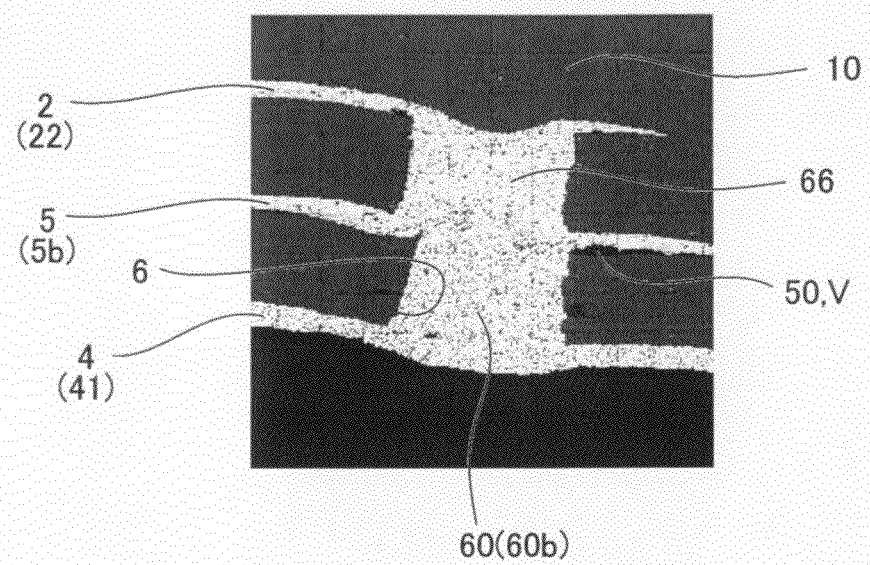
FIG. 9 is a microphotograph of the gas sensor of the present invention in Example 1.
Figure 10:
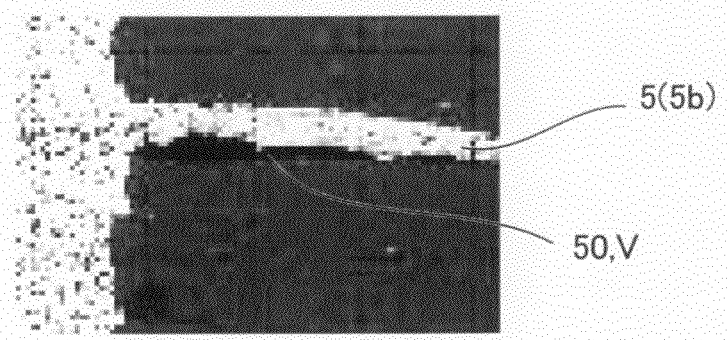
FIG. 10 is an enlarged photograph of a main section in FIG. 7.
Figure 11:
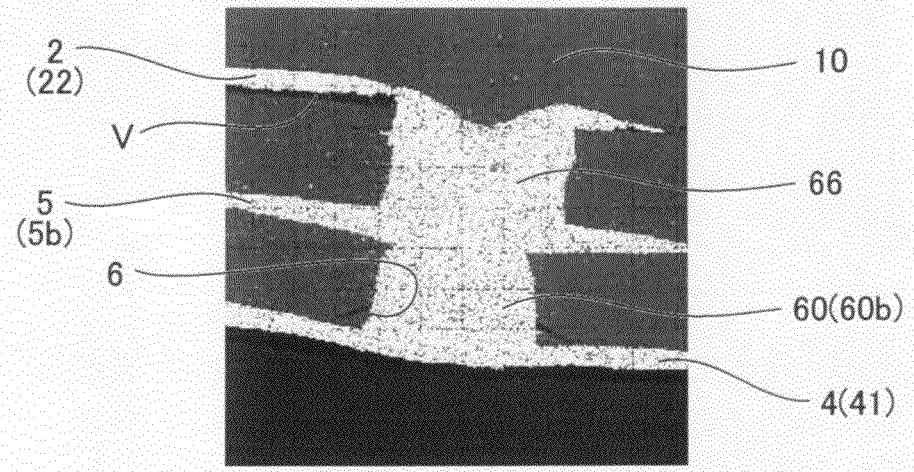
FIG. 11 is a microphotograph of a gas sensor in a comparative example.
Figure 12:
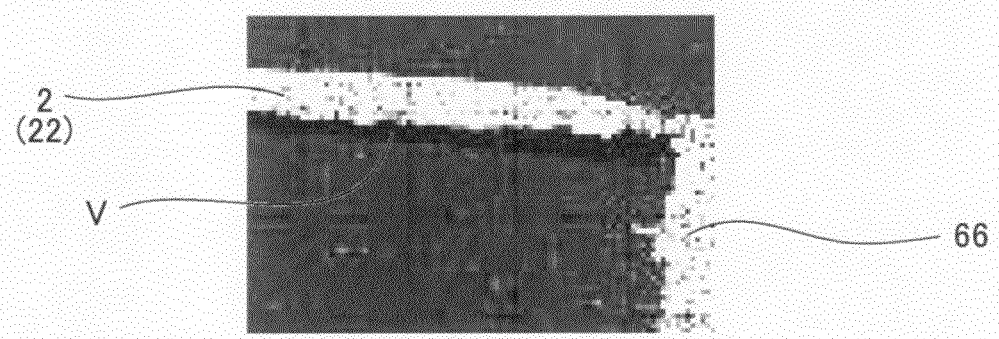
FIG. 12 is an enlarged photograph of a main section in FIG. 11.

Subsequently, Sample 1 and Sample 2 were fired for 120 minutes at 1450±50° C., Microphotographs of the obtained fired Sample 1 and Sample 2 were taken from the heater wiring 22 to the heater electrode 41. The microphotographs of Sample 1 are shown in FIG. 9 and FIG. 10. The microphotographs of Sample 2 are shown in FIG. 11 and FIG. 12.

As shown in FIG. 9 and FIG. 10, in Sample 1, the metal material of the peripheral portion 50 of the intermediate layer 5 moved, and the void V was formed in the peripheral portion 50. Conversely, as shown in FIG. 11 and FIG. 12, in Sample 2 of the comparative example, the void V was formed in the heater wiring 22.

Next, using Sample 1 and Sample 2, a cooling cycle test was conducted in which temperature change between 25° C. and 1000° C. is repeatedly performed. The change in electrical resistance between the heater wiring 22 and the heater electrode 41 was measured. In addition, whether or not a crack was formed between the heater wiring 22 and the heater electrode 41, between the measured gas wiring 20 and the electrode terminal 40a, and between the reference gas side wiring layer 21 and the electrode terminal 40b was evaluated.

Figure 13:
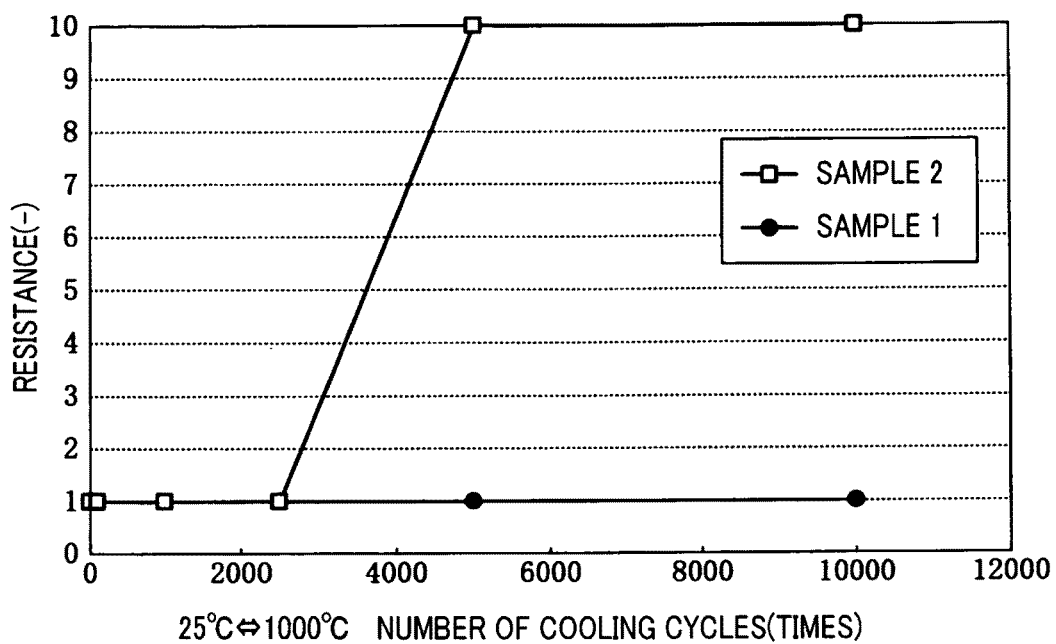
FIG. 13 is a graph showing a relationship between number of cooling cycles and sensor output in Example 1.

In the cooling cycle test, a single cycle is a process in which, after the temperature has been raised from 25° C. to 1000° C., the temperature is returned to 25° C. For each Sample 1 and Sample 2, the cooling cycle test was performed for a number of cycles shown in FIG. 13, and electrical resistance between the heater wiring 22 and the heater electrode 41 was measured. In FIG. 13, a horizontal axis indicates the "number of cycles". In a vertical axis, a value that is a measurement value of the electrical resistance between the heater wiring 22 and the heater electrode 41 divided by a measurement initial value is indicated as "resistance (−)". When the resistance (−) suddenly increases, a judgment is made that a crack has been formed. When the resistance (−) does not change, a judgment is made that a crack has not been formed. The results are shown in Table 1. Instances in which a crack has not been formed are indicated by ○. Instances in which a crack has been formed are indicated by x.

TABLE 1

| 25° C.⇔1000° C. Test of cooling cycles | | |
|---|---|---|
| Number of cooling cycles | Sample1 | Sample2 |
| 1 | ○ | ○ |
| 100 | ○ | ○ |

TABLE 1-continued

25° C.⇔1000° C. Test of cooling cycles

| Number of cooling cycles | Sample1 | Sample2 |
|---|---|---|
| 1000 | ○ | ○ |
| 2500 | ○ | ○ |
| 5000 | ○ | x |
| 10000 | ○ | x |

As shown in FIG. 13 and Table 1, a change in resistance did not occur in Sample 1 even when the cooling cycle was performed 10,000 times, and cracks were not formed, Conversely, in Sample 2 of the comparative example, electrical resistance increased at the 5000-th cycle, and a crack had been formed.

Figure 14:
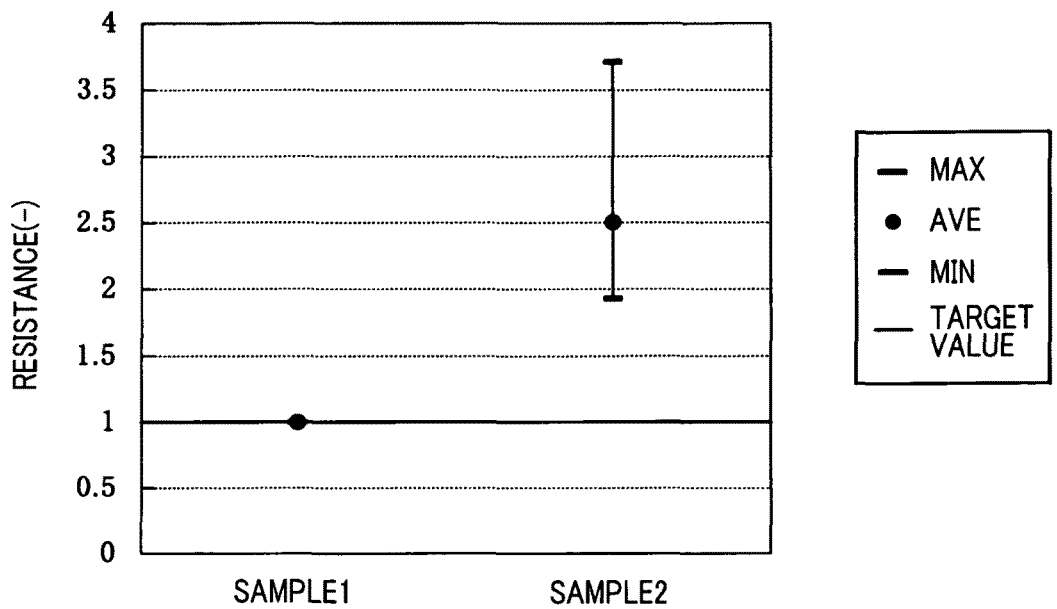
FIG. 14 is a graph comparing resistance values in Example 1.

Next, a plurality of Samples 1 and Samples 2 after firing were manufactured. Electrical resistance between the heater wiring 22 and the heater electrode 41 was measured. The results are shown in FIG. 14. In the vertical axis in FIG. 14, a value that is the measurement value of electrical resistance divided by a target value is indicated as "resistance (–)". Fifty samples were manufactured. As shown in FIG. 14, Sample 1 has an average value of 1, and the measurement value of electrical resistance is equal to the target value. In addition, the variation in measurement value of electrical resistance is small. Conversely, the average value of Sample 2 of the comparative example is a value 2.5 times the target value. Compared to Sample 1, the variation in measurement value of electrical resistance in Sample 2 is large.

Figure 15:
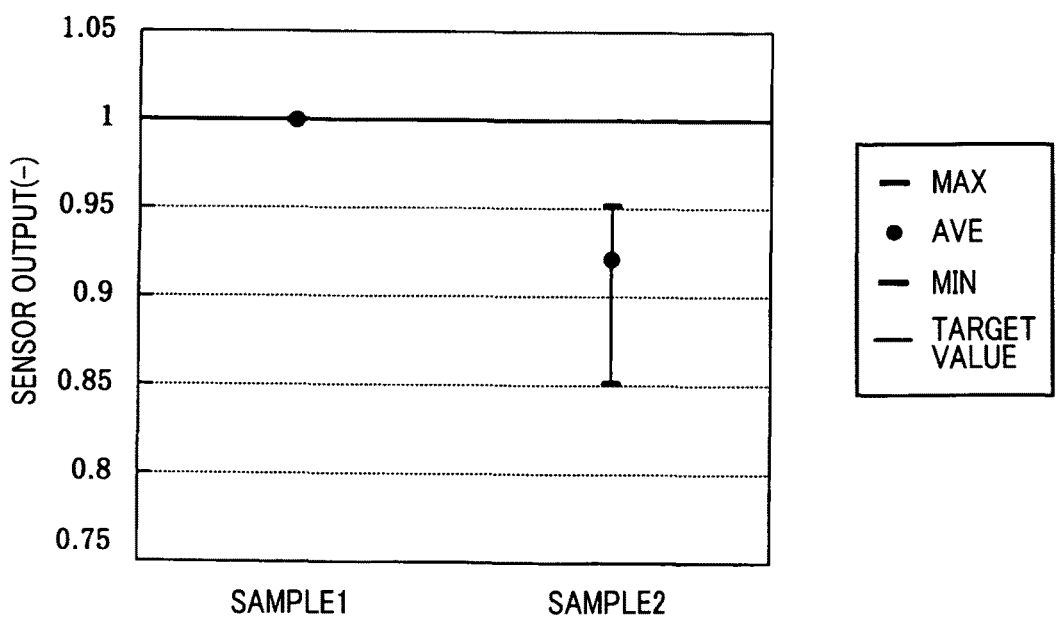
FIG. 15 is a graph comparing sensor output values in Example 1.

Next, using the manufactured Samples 1 and Samples 2, constant power (9 W) was applied to the heater to achieve an element target temperature (700° C.), and an atmospheric IL value that is a sensor output indicator was measured. The results are shown in FIG. 15. In the vertical axis, a value that is a measurement value of the output current when 0.4V is applied to the sensor section 13 divided by a target value is indicated as "sensor output (–)". Fifty samples were manufactured.

As shown in FIG. 15, an output average of Sample 1 is 1 and equal to the target value. In addition, variation in output current is small. Conversely, in Sample 2 of the comparative example, output current average decreased by 8%, and variation in output current is large. The following reasons can be considered regarding the above. Because a void is formed in the heater wiring 22 in Sample 2, electrical resistance increases compared to Sample 1 and the sensor element temperature decreases. In addition, a void is also formed in the measured gas side wiring 20 and the like, causing increase in electrical resistance. The current value when 0.4V is applied decreases, and sensor output decreases. Furthermore, because the variation in electrical resistance occurs, the sensor output also varies.

Table 2 shows judgment results regarding connection reliability between the wiring layer 2 and the electrode terminal 4, and sensor output. In Table 2, samples with favorable connection reliability and sensor output are indicated by ○, and samples with poor connection reliability and sensor output are indicated by x. Instances in which a void has not been formed in the wiring 2 and the like, and the measurement value of electrical resistance is within a target range (99% or more and 101% or less of a target value), or the measurement value of sensor output is within a target range (99% or more and 101% or less of a target value) are indicated by ○. Here, the target value refers to electrical resistance or sensor output empirically expected when a void is not formed.

TABLE 2

| | Judgement | |
|---|---|---|
| Sample | Connection reliability | Sensor output |
| 1 | ○ | ○ |
| 2 | x | x |

As shown in Table 2, Sample 1 has favorable connection reliability and sensor output, whereas Sample 2 has neither.

Next, Sample 3 to Sample 64 were manufactured by changing the ratio B/A of the outer diameter B of the intermediate layer 5a and the outer diameter A of the connecting member 60a, and the thickness d of the intermediate layer 5a as shown in Table 3 below. Other structures are similar to those of Sample 1.

TABLE 3 standard: 0.01 mm ≤ A ≤ 1.315 mm, 0.02 mm ≤ B ≤ 2.63 mm, B ≥ 2A, 0.01 mm ≤ d ≤ 0.1 mm

| Sample | TH diameter: A | Diameter of the intermediate layer: B | B/A | Thickness of the intermediate layer: d |
|---|---|---|---|---|
| 3 | 0.005 | 0.005 | 1.00 | 0.005 |
| 4 | 0.005 | 0.01 | 2.00 | 0.005 |
| 5 | 0.01 | 0.01 | 1.00 | 0.005 |
| 6 | 0.5 | 0.5 | 1.00 | 0.005 |
| 7 | 1 | 1 | 1.00 | 0.005 |
| 8 | 1.315 | 1.315 | 1.00 | 0.005 |
| 9 | 0.01 | 0.02 | 2.00 | 0.005 |
| 10 | 0.01 | 1 | 100.00 | 0.005 |
| 11 | 0.01 | 2.63 | 263.00 | 0.005 |
| 12 | 0.5 | 1 | 2.00 | 0.005 |
| 13 | 0.5 | 2.63 | 5.26 | 0.005 |
| 14 | 1 | 2 | 2.00 | 0.005 |
| 15 | 1 | 2.63 | 2.63 | 0.005 |
| 16 | 1.315 | 2.63 | 2.00 | 0.005 |
| 17 | 0.005 | 0.005 | 1.00 | 0.01 |
| 18 | 0.005 | 0.01 | 2.00 | 0.01 |
| 19 | 0.01 | 0.01 | 1.00 | 0.01 |
| 20 | 0.5 | 0.5 | 1.00 | 0.01 |
| 21 | 1 | 1 | 1.00 | 0.01 |
| 22 | 1.315 | 1.315 | 1.00 | 0.01 |
| 23 | 0.01 | 0.02 | 2.00 | 0.01 |
| 24 | 0.01 | 1 | 100.00 | 0.01 |
| 25 | 0.01 | 2.63 | 263.00 | 0.01 |
| 26 | 0.5 | 1 | 2.00 | 0.01 |
| 27 | 0.5 | 2.63 | 5.26 | 0.01 |
| 28 | 1 | 2 | 2.00 | 0.01 |
| 29 | 1 | 2.63 | 2.63 | 0.01 |
| 30 | 1.315 | 2.63 | 2.00 | 0.01 |
| 31 | 0.01 | 0.02 | 2.00 | 0.05 |
| 32 | 0.01 | 1 | 100.00 | 0.05 |
| 33 | 0.01 | 2.63 | 263.00 | 0.05 |
| 34 | 0.5 | 1 | 2.00 | 0.05 |
| 35 | 0.5 | 2.63 | 5.26 | 0.05 |
| 36 | 1 | 2 | 2.00 | 0.05 |
| 37 | 1 | 2.63 | 2.63 | 0.05 |
| 38 | 1.315 | 2.63 | 2.00 | 0.05 |
| 39 | 0.01 | 0.02 | 2.00 | 0.1 |
| 40 | 0.01 | 1 | 100.00 | 0.1 |
| 41 | 0.01 | 2.63 | 263.00 | 0.1 |
| 42 | 0.5 | 1 | 2.00 | 0.1 |
| 43 | 0.5 | 2.63 | 5.26 | 0.1 |
| 44 | 1 | 2 | 2.00 | 0.1 |
| 45 | 1 | 2.63 | 2.63 | 0.1 |
| 46 | 1.315 | 2.63 | 2.00 | 0.1 |
| 47 | 0.01 | 0.02 | 2.00 | 0.11 |
| 48 | 1.315 | 2.63 | 2.00 | 0.11 |
| 49 | 0.01 | 2.64 | 264.00 | 0.01 |
| 50 | 0.01 | 2.64 | 264.00 | 0.1 |
| 51 | 0.01 | 2.64 | 264.00 | 1.1 |
| 52 | 0.5 | 2.64 | 5.28 | 0.01 |

TABLE 3-continued standard: 0.01 mm ≤ A ≤ 1.315 mm, 0.02 mm ≤ B ≤ 2.63 mm,
B ≥ 2A, 0.01 mm ≤ d ≤ 0.1 mm

| Sample | TH diameter: A | Diameter of the intermediate layer: B | B/A | Thickness of the intermediate layer: d |
|---|---|---|---|---|
| 53 | 0.5 | 2.64 | 5.28 | 0.1 |
| 54 | 0.5 | 2.64 | 5.28 | 1.1 |
| 55 | 1 | 2.64 | 2.64 | 0.01 |
| 56 | 1 | 2.64 | 2.64 | 0.1 |
| 57 | 1 | 2.64 | 2.64 | 1.1 |
| 58 | 1.315 | 2.64 | 2.01 | 0.01 |
| 59 | 1.315 | 2.64 | 2.01 | 0.1 |
| 60 | 1.315 | 2.64 | 2.01 | 1.1 |
| 61 | 1.32 | 2.64 | 2.00 | 0.005 |
| 62 | 1.32 | 2.64 | 2.00 | 0.01 |
| 63 | 1.32 | 2.64 | 2.00 | 0.1 |
| 64 | 1.32 | 2.64 | 2.00 | 1.1 |

In each sample, electrical resistance between the heater wiring 22 and the heater electrode 41, and sensor output were studied. Samples with favorable connection reliability and sensor output are indicated by ○, and samples with poor connection reliability and sensor output are indicated by x. Instances in which a void has not been formed in the wiring 2 and the like, and the measurement value of electrical resistance is within a target range (99% or more and 101% or less of a target value), or the measurement value of sensor output is within a target range (99% or more and 101% or less of a target value), are indicated by ○. The results are shown in Table 4.

TABLE 4

| Sample | Judgement | |
|---|---|---|
| | Connection reliability | Sensor output |
| 3 | x | x |
| 4 | x | x |
| 5 | x | x |
| 6 | x | x |
| 7 | x | x |
| 8 | x | x |
| 9 | x | x |
| 10 | x | x |
| 11 | x | x |
| 12 | x | x |
| 13 | x | x |
| 14 | x | x |
| 15 | x | x |
| 16 | x | x |
| 17 | x | x |
| 18 | x | x |
| 19 | x | x |
| 20 | x | x |
| 21 | x | x |
| 22 | x | x |
| 23 | ○ | ○ |
| 24 | ○ | ○ |
| 25 | ○ | ○ |
| 26 | ○ | ○ |
| 27 | ○ | ○ |
| 28 | ○ | ○ |
| 29 | ○ | ○ |
| 30 | ○ | ○ |
| 31 | ○ | ○ |
| 32 | ○ | ○ |
| 33 | ○ | ○ |
| 34 | ○ | ○ |
| 35 | ○ | ○ |
| 36 | ○ | ○ |
| 37 | ○ | ○ |
| 38 | ○ | ○ |
| 39 | ○ | ○ |
| 40 | ○ | ○ |
| 41 | ○ | ○ |
| 42 | ○ | ○ |
| 43 | ○ | ○ |
| 44 | ○ | ○ |
| 45 | ○ | ○ |
| 46 | ○ | ○ |
| 47 | x | x |
| 48 | x | x |
| 49 | x | x |
| 50 | x | x |
| 51 | x | x |
| 52 | x | x |
| 53 | x | x |
| 54 | x | x |
| 55 | x | x |
| 56 | x | x |
| 57 | x | x |
| 58 | x | x |
| 59 | x | x |
| 60 | x | x |
| 61 | x | x |
| 62 | x | x |
| 63 | x | x |
| 64 | x | x |

Table 3 and Table 4 indicate that samples having the following ranges have favorable connection reliability and sensor output: 0.01 mm≤A≤1.315 mm, 0.02 mm≤B≤2.63 mm, and 0.01 mm≤d≤0.1 mm.

Next, Sample 65 to Sample 67 were manufactured by changing the Pt/Pd composition (see Table 5) of the first metal material composing the sensor electrode 40, the heater electrode 41, and the connecting members 60*a* and 60*b*. Other material compositions and structures are the same as those of Sample 1. For each sample, electrical resistance between the heater wiring 22 and the heater electrode 41, and sensor output were studied. Samples with favorable connection reliability and sensor output are indicated by ○, and samples with poor connection reliability and sensor output are indicated by x in Table 5. Instances in which a void has not been formed in the wiring 2 and the like, and the measurement value of electrical resistance is within a target range (99% or more and 101% or less of a target value), or the measurement value of sensor output is within a target range (99% or more and 101% or less of a target value), are indicated by ○.

TABLE 5

| Sample | Pt/Pd Composition ratio (wt %) | Judgement | |
|---|---|---|---|
| | | Connection reliability | Sensor output |
| 65 | 90/10 | ○ | ○ |
| 66 | 50/50 | ○ | ○ |
| 67 | 10/90 | ○ | ○ |

Table 5 indicates that even when the Pt/Pd composition ratio of the first metal material in Sample 65 to Sample 67 is changed between 90/10 and 10/90, connection reliability between the heater wiring 22 and the heater electrode 41, and sensor output are favorable.

Second Embodiment

Figure 16:
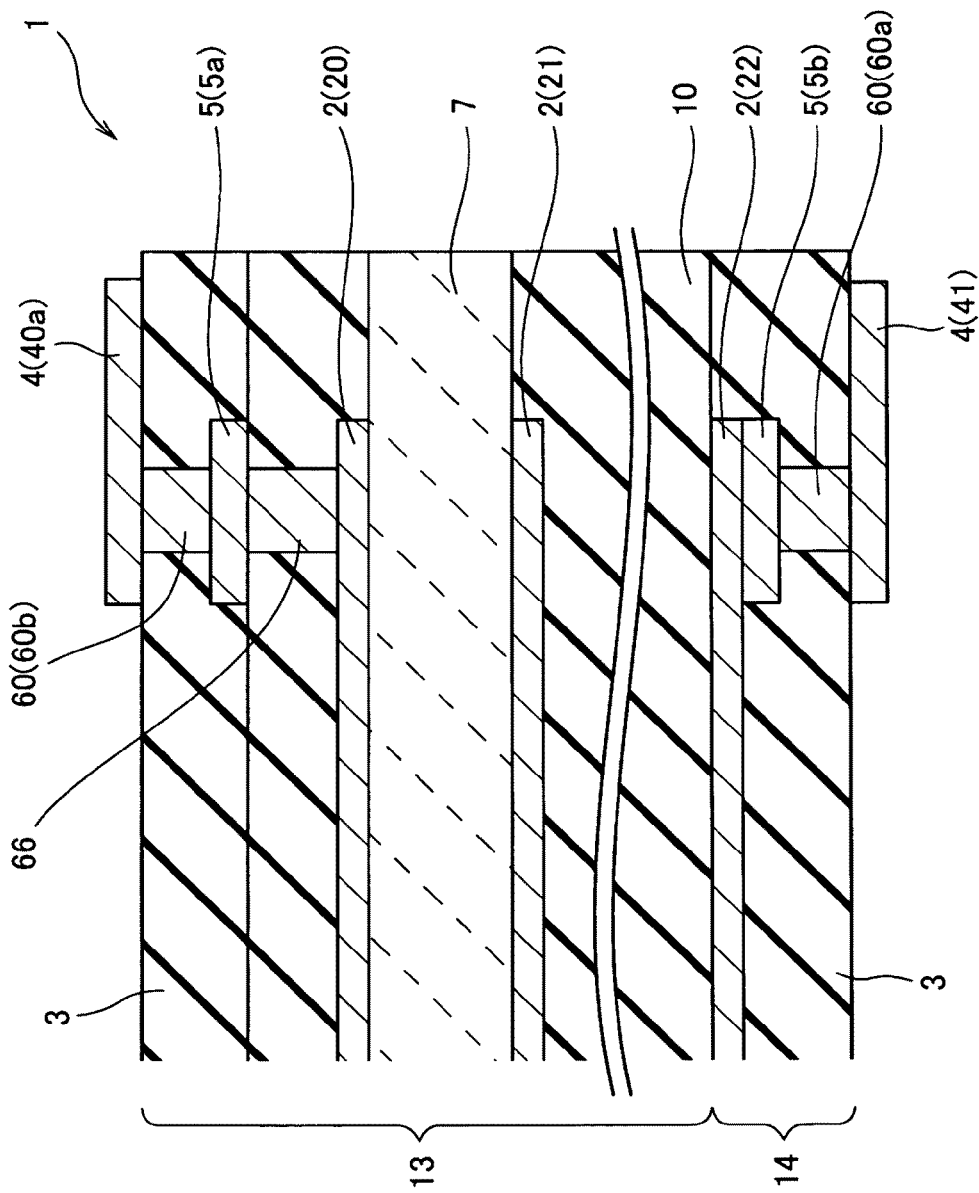
FIG. 16 is a cross-sectional view of a gas sensor element passing through a first sensor electrode 40a before firing according to a second embodiment of the present invention.
Figure 17:
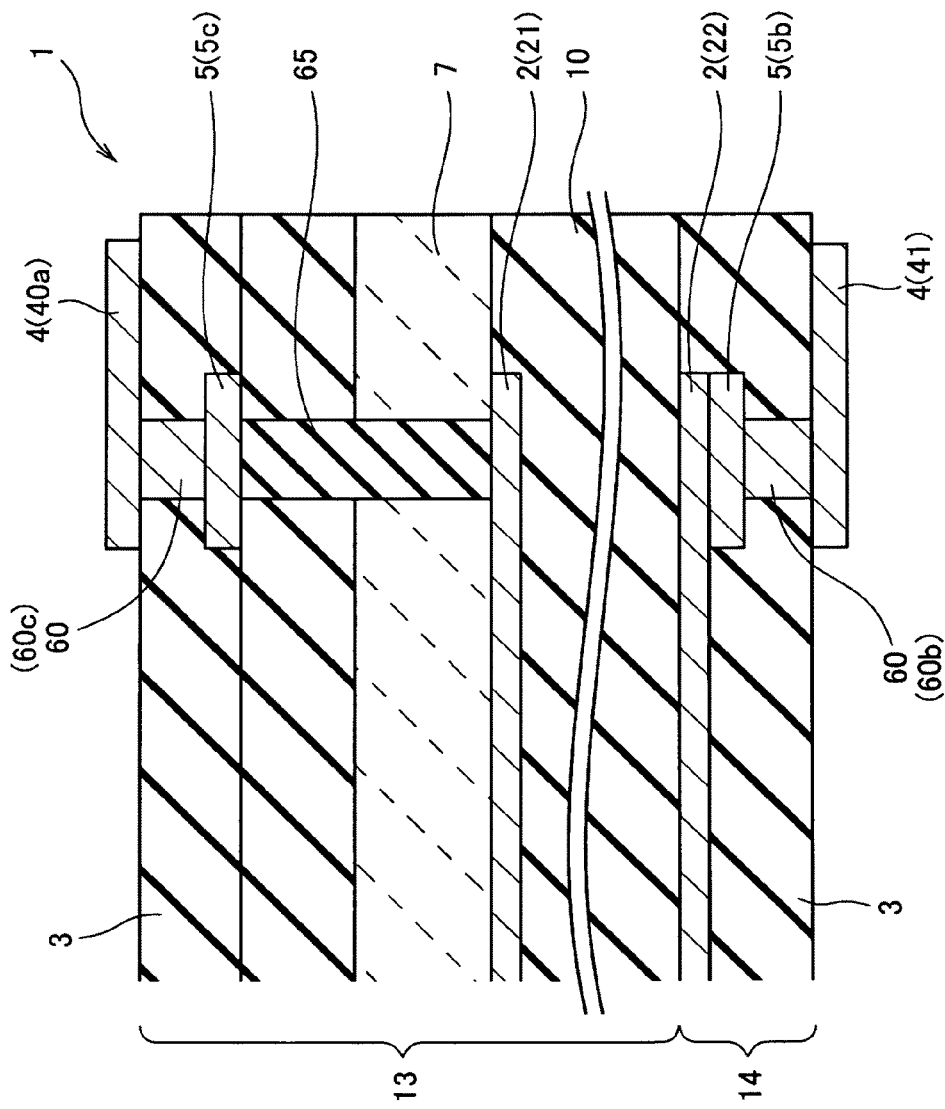
FIG. 17 is a cross-sectional view of a gas sensor element passing through a second sensor electrode 40b before firing according to a second embodiment of the present invention.

FIG. 16 and FIG. 17

According to a second embodiment, the connection structure of the electrode terminal 4 and the wiring layer 2 in the gas sensor element 1 according to the first embodiment is changed.

As shown in FIG. 16, the measured gas side wiring 20 is disposed within the sensor section 13, and the surface of the measured gas side wiring 20 is covered by the insulating layer 3. The first sensor electrode 40a is disposed on the main surface of the insulating layer 3 on the opposite side of the insulating layer 3 from the measured gas side wiring 20. The first connecting member 60b, the intermediate layer 5b, and the second connecting member 66 are interposed between the first sensor electrode 40a and the measured gas side wiring 20, and the first sensor electrode 40a is electrically connected to the measured gas side wiring 20.

The heater wiring 22 is disposed within the heater section 14, and the surface of the heater wiring 22 is covered by the insulating layer 3. The heater electrode 41 is disposed on the main surface of the insulating layer 3 on the opposite side of the insulating layer 3 from the heater wiring 22. The intermediate layer 5b and the connecting member 60a are interposed between the heater wiring 22 and the heater electrode 41, and the heater electrode 41 is electrically connected to the heater wiring 22. The intermediate layer 5 and the connecting member 60a are directly connected.

The first sensor electrode 40a, the first connecting member 60b, the connecting member 60a, and the heater electrode 41 are composed of the first metal material. The intermediate layers 5a and 5b, the second connecting members 66, the reference gas side wiring 21, and the heater wiring 22 are composed of the second metal material having a lower melting point than the first metal material.

As shown in FIG. 17, in the sensor section 13, the sensor side second connecting members 65 that pass through the sensor side first connecting member 60c, the intermediate layer 5c, and the solid electrolyte body 7 are disposed between the second sensor electrode 40b and the reference gas side wiring 21. The second sensor electrode 40b is electrically connected to the reference gas side wiring 21.

The second sensor electrode 40b and the sensor side first connecting member 60c are composed of the first metal material. The intermediate layer 5c, the sensor side second connecting member 65, and the reference gas side wiring 21 are composed of the second metal material having a lower melting point than the first metal material.

On the other hand, the heater section 14 is the same as the heater section 14 shown in FIG. 16.

Other configurations are similar to those according to the above-described first embodiment. Therefore, explanations thereof are omitted.

According to the second embodiment, the same operational effects as those according to the first embodiment can be achieved.

Third Embodiment

FIG. 18

According to a third embodiment, the connection structure of the electrode terminal 4 and the wiring layer 2 in the gas sensor element 1 according to the first embodiment is changed. Descriptions of sections that are the same as those in the gas sensor element 1 according to the first embodiment are omitted.

Figure 18:
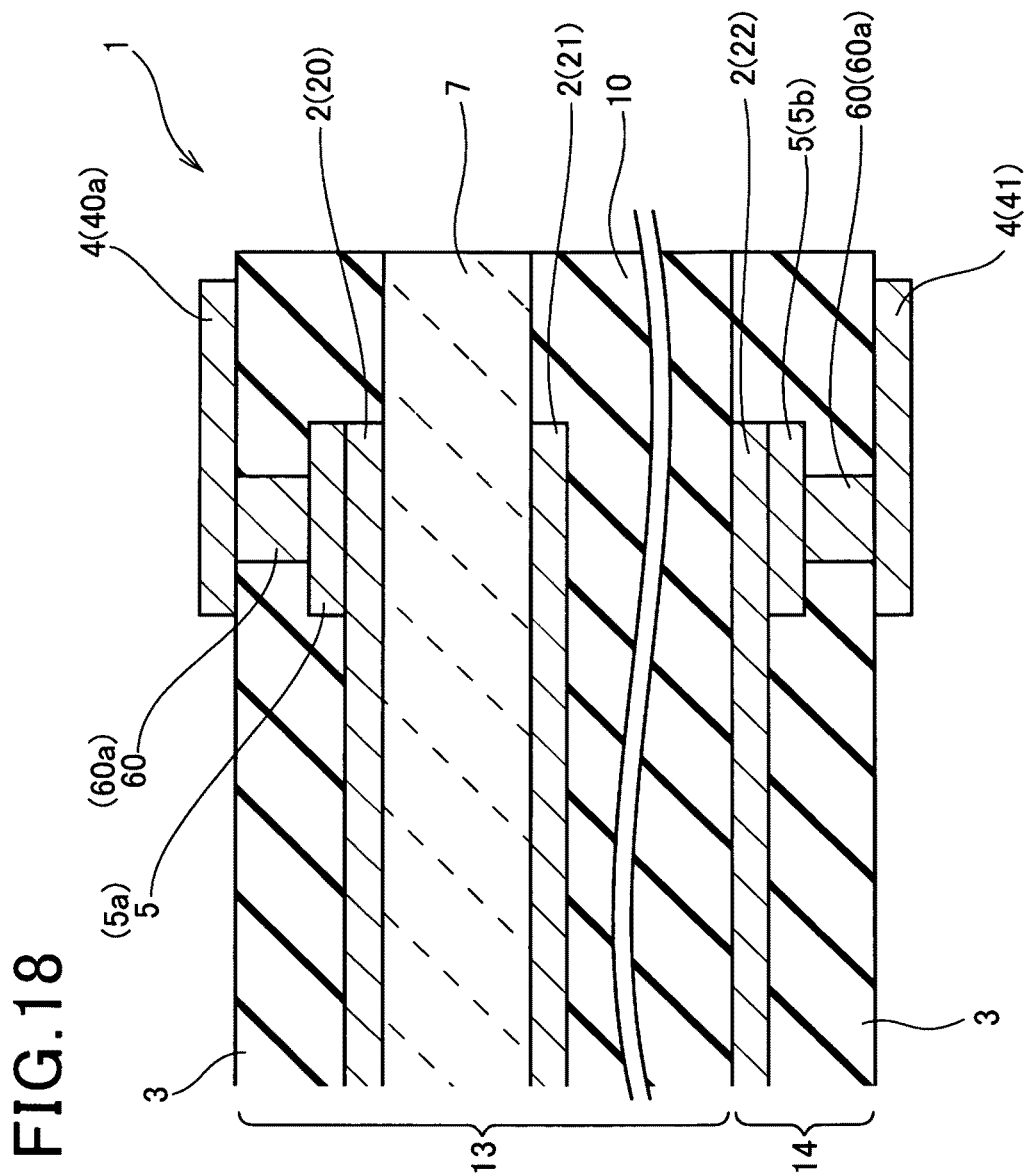
FIG. 18 is a cross-sectional view of a gas sensor element passing through a first sensor electrode 40a before firing according to a third embodiment of the present invention.

As shown in FIG. 18, the sensor section 13 has the same configuration and uses the same material as the sensor section 13 shown in FIG. 4. The heater section 14 has the same configuration and uses the same material as the heater section 14 shown in FIG. 16.

Other configurations are similar to those according to the above-described first embodiment. Therefore, explanations thereof are omitted.

According to the third embodiment, the same operational effects as those according to the first embodiment can be achieved.

Fourth Embodiment

FIG. 19

According to a fourth embodiment, the connection structure of the electrode terminal 4 and the wiring layer 2 in the gas sensor element 1 according to the first embodiment is changed.

Figure 19:
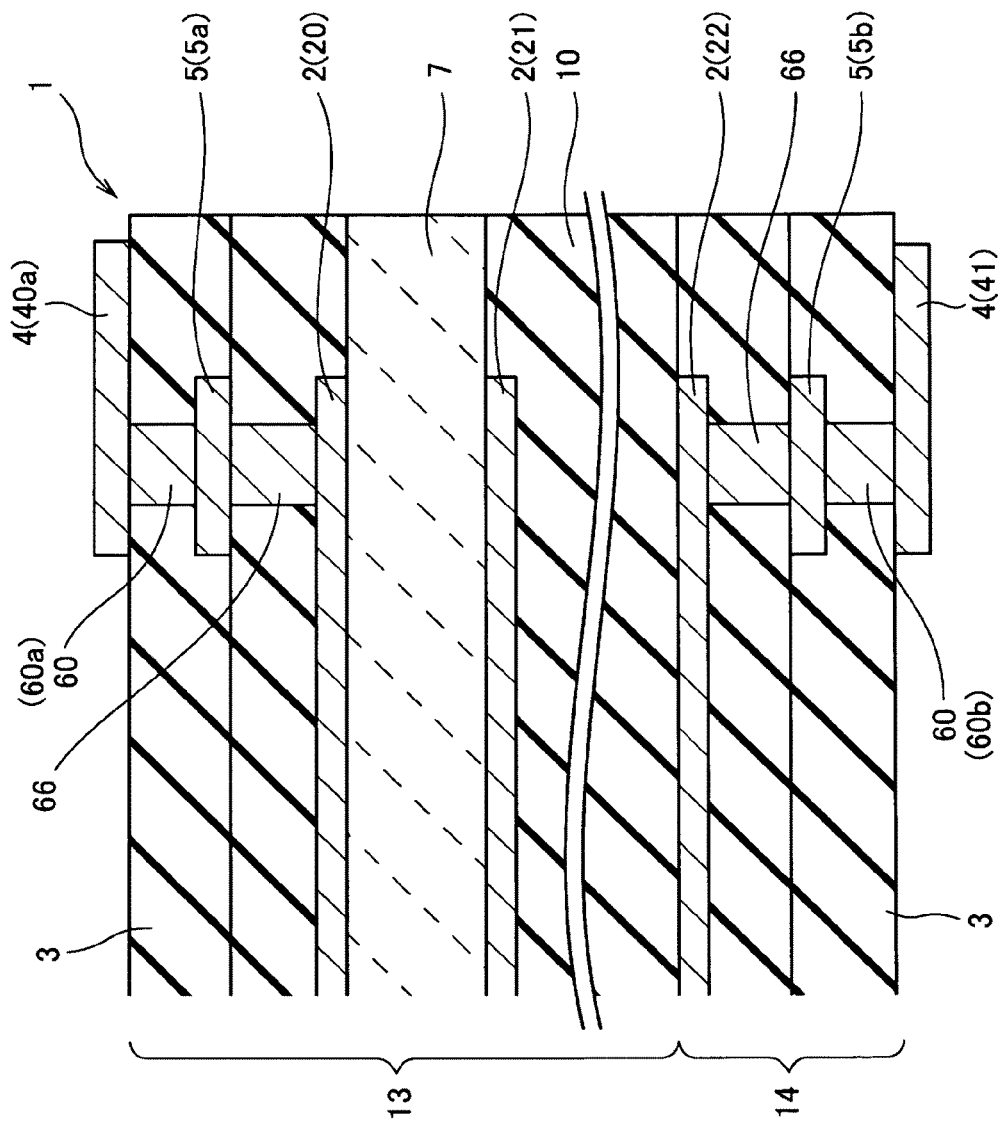
FIG. 19 is a cross-sectional view of a gas sensor element passing through a first sensor electrode 40a before firing according to a fourth embodiment of the present invention.

As shown in FIG. 19, the sensor section 13 has the same configuration and uses the same material as the sensor section 13 shown in FIG. 16. The heater section 14 has the same configuration and uses the same material as the heater section 14 shown in FIG. 4.

Other configurations are similar to those according to the above-described first embodiment. Therefore, explanations thereof are omitted.

According to the fourth embodiment, the same operational effects as those according to the first embodiment can be achieved.

Fifth Embodiment

FIG. 20

According to a fifth embodiment, the connection structure of the electrode terminal 4 and the wiring layer 2 in the gas sensor element 1 according to the first embodiment is changed.

Figure 20:
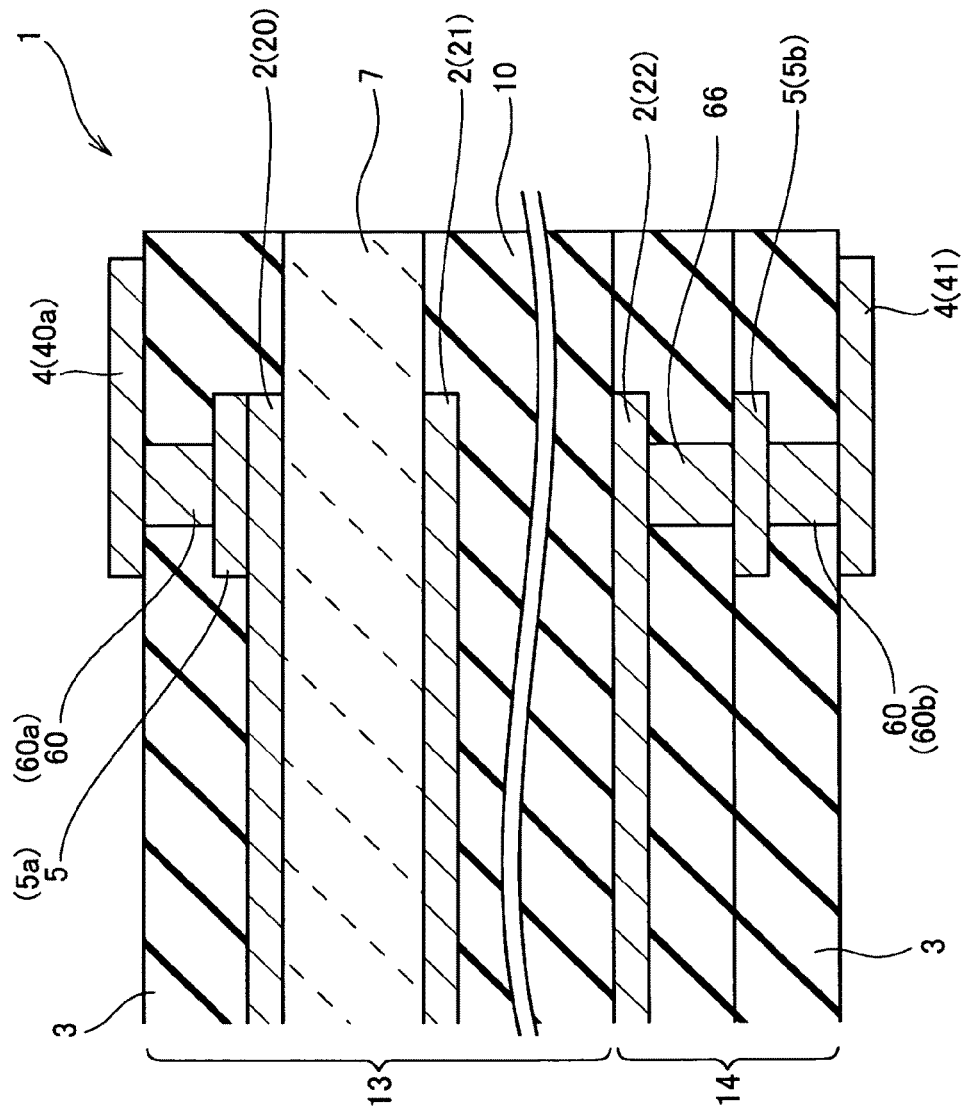
FIG. 20 is a cross-sectional view of a gas sensor element passing through a first sensor electrode 40a before firing according to a fifth embodiment of the present invention.

As shown in FIG. 20, the sensor section 13 has the same configuration as the sensor section 13 in FIG. 4. The difference with the sensor section 13 in FIG. 4 is that the metal material of the intermediate layer 5a, the measured gas side wiring 20, and the reference gas side wiring 21 has been changed from the second metal material to the first metal material.

The heater section 14 has the same configuration and uses the same material as the heater section 14 shown in FIG. 4.

Other configurations are similar to those according to the above-described first embodiment. Therefore, explanations thereof are omitted.

According to the fifth embodiment, the same operational effects as those according to the first embodiment can be achieved.

Hereafter, experiments were conducted to confirm the effects of the gas sensor element 1 according to a fifth embodiment using Example 2.

Example 2

In Example 2, a sample was manufactured having a similar structure as the gas sensor element 1 according to the fifth embodiment (FIG. 20) by stacking the electrode terminal 4, the insulating layer 3, the intermediate layer 5, and the like. Here, the first sensor electrode 40a, the connecting member 60a, the intermediate layer 5a, the measured gas side wiring 20, the reference gas side wiring 21, the first connecting member 60b, and the heater electrode 41 were composed of the first metal material. The heater wiring 22, the second connecting member 66, and the intermediate layer 5b were composed of the second metal material having a lower melting point than the first metal material.

Respective dimensions of the electrode terminal 4, the connecting member 60, the intermediate layers 5a and 5b, the wiring layers 20, 21, and 22, the insulating layers 3, the first heater substrate 31a, and the second heater substrate 31b are the same as those in Sample 1 in Example 1. The obtained sample is Sample 68 of the gas sensor element in Example 2. As a comparative example, Sample 69 was used having the same configuration as Sample 2 manufactured in Example 1.

Subsequently, Sample 68 and Sample 69 were fired for 120 minutes at 1450±50° C. A plurality of fired Samples 68 and Samples 69 were manufactured. Under the same conditions as those in Example 1, electrical resistance between the heater electrode 41 and the heater wiring 22 were measured, and the atmospheric IL value was measured. The number of measured samples was 50 samples each. From the measurement results, connection reliability between the heater electrode 41 and the heater wiring 22 and sensor output were judged. The results are shown in Table 6. Judgment criteria are the same as those in Example 1 and indicated using ○ and x,

TABLE 6

| Sample | Judgement | |
|---|---|---|
| | Connection reliability | Sensor output |
| 68 | ○ | ○ |
| 69 | x | x |

As shown in Table 6, Sample 68 has favorable connection reliability and sensor output. Neither connection reliability nor sensor output is favorable in Sample 69 of the comparative example.

Next, Sample 70 to Sample 131 were manufactured by changing the ratio EVA of the outer diameter 8 of the intermediate layer 5b and the outer diameter A of the connecting member 60a, and the thickness d of the intermediate layer 5b as shown in Table 7 and Table 8, below. Other structures were similar to those of Sample 68. Electrical resistance between the heater wiring 22 and the heater electrode 41, and sensor output were studied for each sample. The results are shown in Table 7 and Table 8. Judgment criteria are the same as those in Example 1 and indicated using ○ and x.

TABLE 7 standard: 0.01 mm ≤ A ≤ 1.315 mm, 0.02 mm ≤ B ≤ 2.63 mm, B ≥ 2A, 0.01 mm ≤ d ≤ 0.1 mm

| Sample | TH diameter: A | Diameter of the intermediate layer: B | B/A | Thickness of the intermediate layer: d |
|---|---|---|---|---|
| 70 | 0.005 | 0.005 | 1.00 | 0.005 |
| 71 | 0.005 | 0.01 | 2.00 | 0.005 |
| 72 | 0.01 | 0.01 | 1.00 | 0.005 |
| 73 | 0.5 | 0.5 | 1.00 | 0.005 |
| 74 | 1 | 1 | 1.00 | 0.005 |
| 75 | 1.315 | 1.315 | 1.00 | 0.005 |
| 76 | 0.01 | 0.02 | 2.00 | 0.005 |
| 77 | 0.01 | 1 | 100.00 | 0.005 |
| 78 | 0.01 | 2.63 | 263.00 | 0.005 |
| 79 | 0.5 | 1 | 2.00 | 0.005 |
| 80 | 0.5 | 2.63 | 5.26 | 0.005 |
| 81 | 1 | 2 | 2.00 | 0.005 |
| 82 | 1 | 2.63 | 2.63 | 0.005 |
| 83 | 1.315 | 2.63 | 2.00 | 0.005 |
| 84 | 0.005 | 0.005 | 1.00 | 0.01 |
| 85 | 0.005 | 0.01 | 2.00 | 0.01 |
| 86 | 0.01 | 0.01 | 1.00 | 0.01 |
| 87 | 0.5 | 0.5 | 1.00 | 0.01 |
| 88 | 1 | 1 | 1.00 | 0.01 |
| 89 | 1.315 | 1.315 | 1.00 | 0.01 |
| 90 | 0.01 | 0.02 | 2.00 | 0.01 |
| 91 | 0.01 | 1 | 100.00 | 0.01 |
| 92 | 0.01 | 2.63 | 263.00 | 0.01 |
| 93 | 0.5 | 1 | 2.00 | 0.01 |
| 94 | 0.5 | 2.63 | 5.26 | 0.01 |
| 95 | 1 | 2 | 2.00 | 0.01 |
| 96 | 1 | 2.63 | 2.63 | 0.01 |
| 97 | 1.315 | 2.63 | 2.00 | 0.01 |
| 98 | 0.01 | 0.02 | 2.00 | 0.05 |
| 99 | 0.01 | 1 | 100.00 | 0.05 |
| 100 | 0.01 | 2.63 | 263.00 | 0.05 |
| 101 | 0.5 | 1 | 2.00 | 0.05 |
| 102 | 0.5 | 2.63 | 5.26 | 0.05 |
| 103 | 1 | 2 | 2.00 | 0.05 |
| 104 | 1 | 2.63 | 2.63 | 0.05 |
| 105 | 1.315 | 2.63 | 2.00 | 0.05 |
| 106 | 0.01 | 0.02 | 2.00 | 0.1 |
| 107 | 0.01 | 1 | 100.00 | 0.1 |
| 108 | 0.01 | 2.63 | 263.00 | 0.1 |
| 109 | 0.5 | 1 | 2.00 | 0.1 |
| 110 | 0.5 | 2.63 | 5.26 | 0.1 |
| 111 | 1 | 2 | 2.00 | 0.1 |
| 112 | 1 | 2.63 | 2.63 | 0.1 |
| 113 | 1.315 | 2.63 | 2.00 | 0.1 |
| 114 | 0.01 | 0.02 | 2.00 | 0.11 |
| 115 | 1.315 | 2.63 | 2.00 | 0.11 |
| 116 | 0.01 | 2.64 | 264.00 | 0.01 |
| 117 | 0.01 | 2.64 | 264.00 | 0.1 |
| 118 | 0.01 | 2.64 | 264.00 | 1.1 |
| 119 | 0.5 | 2.64 | 5.28 | 0.01 |
| 120 | 0.5 | 2.64 | 5.28 | 0.1 |
| 121 | 0.5 | 2.64 | 5.28 | 1.1 |
| 122 | 1 | 2.64 | 2.64 | 0.01 |
| 123 | 1 | 2.64 | 2.64 | 0.1 |
| 124 | 1 | 2.64 | 2.64 | 1.1 |
| 125 | 1.315 | 2.64 | 2.01 | 0.01 |
| 126 | 1.315 | 2.64 | 2.01 | 0.1 |
| 127 | 1.315 | 2.64 | 2.01 | 1.1 |
| 128 | 1.32 | 2.64 | 2.00 | 0.005 |
| 129 | 1.32 | 2.64 | 2.00 | 0.01 |
| 130 | 1.32 | 2.64 | 2.00 | 0.1 |
| 131 | 1.32 | 2.64 | 2.00 | 1.1 |

TABLE 8

| Sample | Judgement | |
|---|---|---|
| | Connection reliability | Sensor output |
| 70 | x | x |
| 71 | x | x |
| 72 | x | x |
| 73 | x | x |
| 74 | x | x |
| 75 | x | x |
| 76 | x | x |

TABLE 8-continued

| Sample | Judgement Connection reliability | Sensor output |
|---|---|---|
| 77 | x | x |
| 78 | x | x |
| 79 | x | x |
| 80 | x | x |
| 81 | x | x |
| 82 | x | x |
| 83 | x | x |
| 84 | x | x |
| 85 | x | x |
| 86 | x | x |
| 87 | x | x |
| 88 | x | x |
| 89 | x | x |
| 90 | ○ | ○ |
| 91 | ○ | ○ |
| 92 | ○ | ○ |
| 93 | ○ | ○ |
| 94 | ○ | ○ |
| 95 | ○ | ○ |
| 96 | ○ | ○ |
| 97 | ○ | ○ |
| 98 | ○ | ○ |
| 99 | ○ | ○ |
| 100 | ○ | ○ |
| 101 | ○ | ○ |
| 102 | ○ | ○ |
| 103 | ○ | ○ |
| 104 | ○ | ○ |
| 105 | ○ | ○ |
| 106 | ○ | ○ |
| 107 | ○ | ○ |
| 108 | ○ | ○ |
| 109 | ○ | ○ |
| 110 | ○ | ○ |
| 111 | ○ | ○ |
| 112 | ○ | ○ |
| 113 | ○ | ○ |
| 114 | x | x |
| 115 | x | x |
| 116 | x | x |
| 117 | x | x |
| 118 | x | x |
| 119 | x | x |
| 120 | x | x |
| 121 | x | x |
| 122 | x | x |
| 123 | x | x |
| 124 | x | x |
| 125 | x | x |
| 126 | x | x |
| 127 | x | x |
| 128 | x | x |
| 129 | x | x |
| 130 | x | x |
| 131 | x | x |

Table 7 and Table 8 indicate that samples having the following ranges have favorable connection reliability and sensor output: 0.01 mm≤A≤1.315 mm, 0.02 mm≤B2.63 mm, B/A≥2, and 0.01 mm≤d≤0.1 mm.

Next, Sample 132 to Sample 134 were manufactured by changing the Pt/Pd composition (see Table 9) of the first metal material. Other material compositions and structures were the same as those of Sample 68. The electrical resistance between the heater wiring 22 and the heater electrode 41 and sensor output were studied for each sample. The results are shown in Table 9. Judgment criteria are the same as those in Example 1 and indicated using ○ and X.

TABLE 9

| | Pt/Pd Composition | Judgement | |
|---|---|---|---|
| Sample | ratio (wt %) | Connection reliability | Sensor output |
| 132 | 90/10 | ○ | ○ |
| 133 | 50/50 | ○ | ○ |
| 134 | 10/90 | ○ | ○ |

Table 9 indicates that even when the Pt/Pd composition ratio of the first metal material is changed between 90/10 and 10/90, connection reliability between the heater wiring 22 and the heater electrode 41, and sensor output in Sample 132 to Sample 134 are favorable.

Sixth Embodiment

FIG. 21

According to a sixth embodiment, the connection structure of the electrode terminal 4 and the wiring layer 2 is the same as that of the gas sensor element 1 according to the third embodiment (see FIG. 18). The material of the sensor section 13 is changed.

Figure 21:
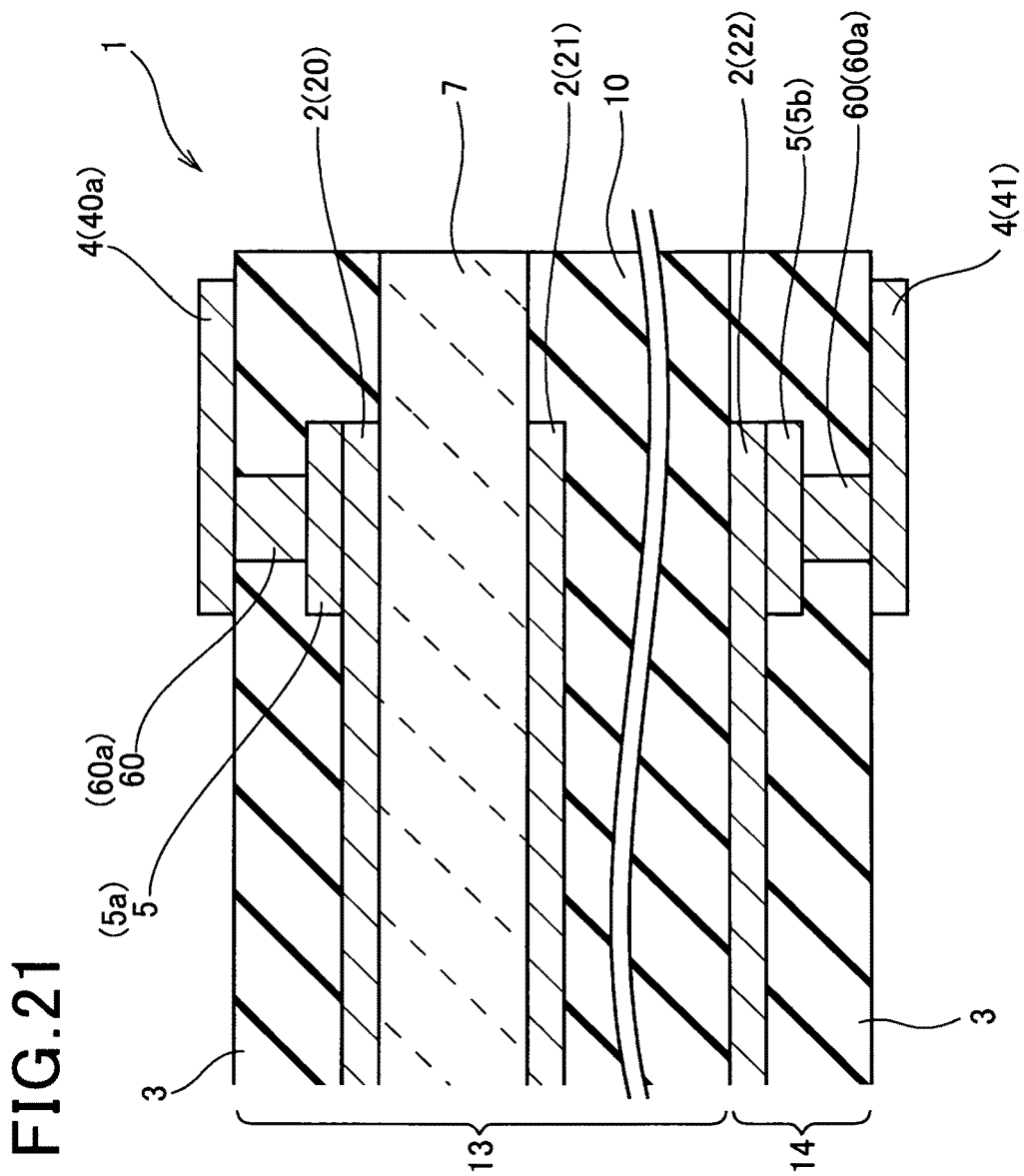
FIG. 21 is a cross-sectional view of a gas sensor element passing through a first sensor electrode 40a before firing according to a sixth embodiment of the present invention.

Specifically, as shown in FIG. 21, the difference with the gas sensor element 1 according to the third embodiment is that the intermediate layer 5a, the measured gas side wiring 20, and the reference gas side wiring 21 of the sensor section 13 are composed of the first metal material.

Other configurations are similar to those according to the above-described first embodiment. Therefore, explanations thereof are omitted.

According to the sixth embodiment, the same operational effects as those according to the first embodiment can be achieved.

Seventh Embodiment

FIG. 22

According to a seventh embodiment, the connection structure of the electrode terminal 4 and the wiring layer 2 is the same as that of the gas sensor element 1 according to the fourth embodiment (see FIG. 19). The material of the sensor section 13 is changed.

Figure 22:
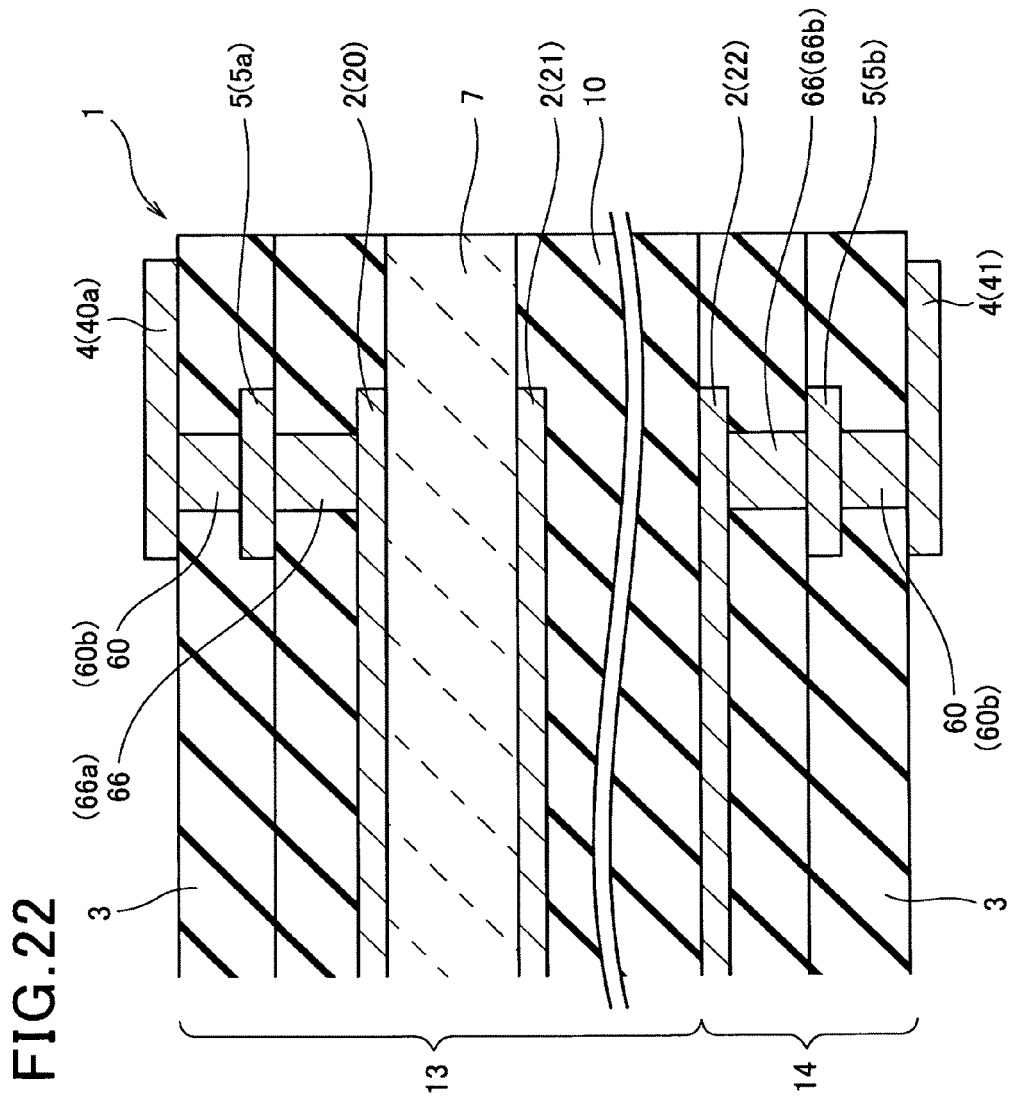
FIG. 22 is a cross-sectional view of a gas sensor element passing through a first sensor electrode 40a before firing according to a seventh embodiment of the present invention.

Specifically, as shown in FIG. 22, the difference with the gas sensor element 1 according to the fourth embodiment is that the intermediate layer 5a, the measured gas side second connecting member 66a, the measured gas side wiring 20, and the reference gas side wiring 21 are composed of the first metal material.

Other configurations are similar to those according to the above-described first embodiment. Therefore, explanations thereof are omitted.

According to the seventh embodiment, the same operational effects as those according to the first embodiment can be achieved.

Eighth Embodiment

FIG. 23

According to an eighth embodiment, the connection structure of the electrode terminal 4 and the wiring layer 2 is the same as that of the gas sensor element 1 according to the second embodiment (see FIG. 16). The material of the sensor section 13 is changed.

Figure 23:
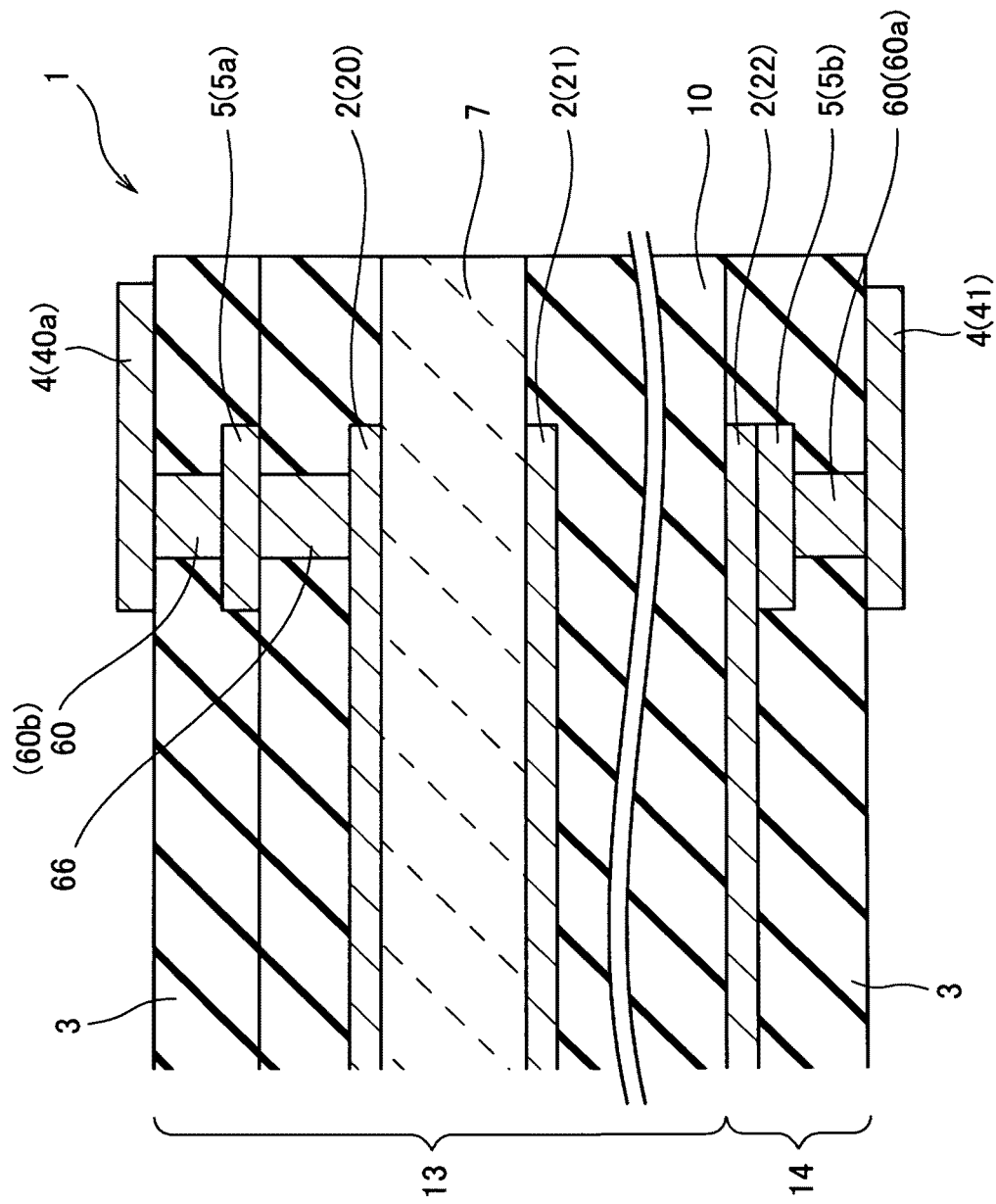
FIG. 23 is a cross-sectional view of a gas sensor element passing through a first sensor electrode 40a before firing according to an eighth embodiment of the present invention.

Specifically, as shown in FIG. 23, the difference with the gas sensor element 1 according to the second embodiment (see FIG. 16) is that the intermediate layer 5a, the second connecting member 66, the measured gas side wiring 20, and the reference gas side wiring 21 are composed of the first metal material.

Other configurations are similar to those according to the above-described first embodiment. Therefore, explanations thereof are omitted.

According to the eighth embodiment, the same operational effects as those according to the first embodiment can be achieved.

Ninth Embodiment

FIG. 24

According to a ninth embodiment, the connection structure of the electrode terminal 4 and the wiring layer 2 is the same as that of the gas sensor element 1 according to the first embodiment (FIG. 4). The material of the heater section 14 is changed.

Figure 24:
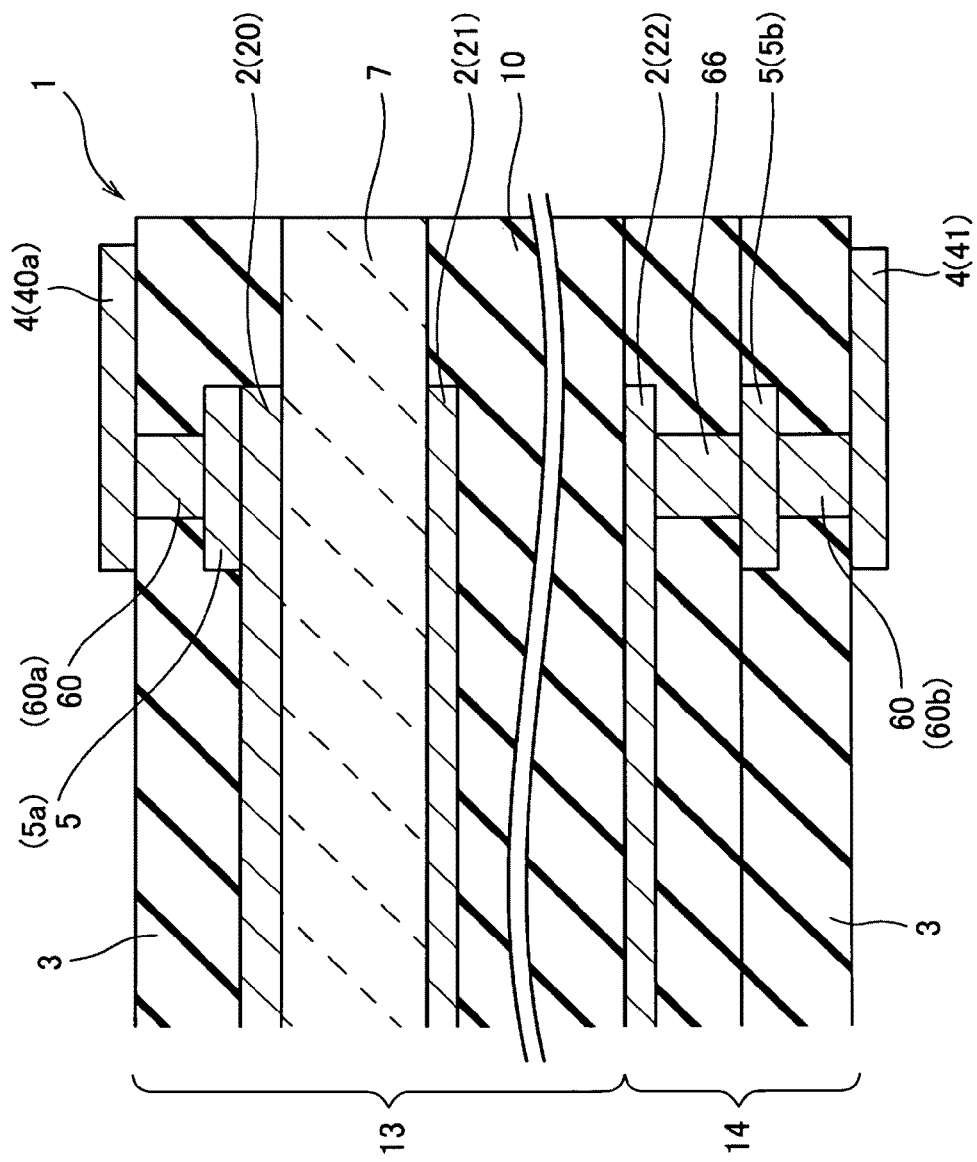
FIG. 24 is a cross-sectional view of a gas sensor element passing through a first sensor electrode 40a before firing according to a ninth embodiment of the present invention.

Specifically, as shown in FIG. 24, the difference with the gas sensor element 1 according to the first embodiment (FIG. 4) is that the heater wiring 2, the second connecting member 66, and the inter mediate layer 5b are composed of the first metal material.

Other configurations are similar to those according to the above-described first embodiment. Therefore, explanations thereof are omitted.

According to the ninth embodiment, the same operational effects as those according to the first embodiment can be achieved.

Example 3

In Example 3, a sample was manufactured having a similar structure as the gas sensor element 1 according to the ninth embodiment (FIG. 24) by stacking the electrode terminal 4, the insulating layer 3, the intermediate layer 5, and the like. Here, the first sensor electrode 40a, the connecting member 60a, the intermediate layer 5a, the heater wiring 22, the second connecting member 66, the intermediate layer 5b, the first connecting member 60b, and the heater electrode 41 were composed of the first metal material.

The intermediate layer 5b, the measured gas side wiring 20, and the reference gas side wiring 21 were composed of the second metal material having a lower melting point than the first metal material.

Respective dimensions of the electrode terminal 4, the connecting member 60, the intermediate layers 5a and 5b, the wiring layers 20, 21, and 22, the insulating layers 3, the first heater substrate 31a, and the second heater substrate 31b are the same as those in Sample 1 in Example 1. The obtained sample is Sample 135 of the gas sensor element in Example 3. As a comparative example, Sample 136 was used having the same configuration as Sample 2 manufactured in Example 1.

Subsequently, Sample 135 and Sample 136 were fired for 120 minutes at 1450±50° C. A plurality of fired Samples 135 and Samples 136 were manufactured. Under the same conditions as those in Example 1, electrical resistance between the first sensor electrode 40a and the measured gas side wiring 20 were measured, and the atmospheric IL value was measured. The number of measured samples was 50 samples each. From the measurement results, connection reliability between the heater electrode 41 and the heater wiring 22 and sensor output were judged. The results are shown in Table 10. Judgment criteria are the same as those in Example 1 and indicated using ○ and x.

TABLE 10

| | Judgement | |
|---|---|---|
| Sample | Connection reliability | Sensor output |
| 135 | ○ | ○ |
| 136 | x | x |

As shown in Table 10, Sample 135 has favorable connection reliability and sensor output. Neither connection reliability nor sensor output is favorable in Sample 136 of the comparative example.

Next, Sample 137 to Sample 198 were manufactured by changing the ratio B/A of the outer diameter B of the intermediate layer 5b and the outer diameter A of the connecting member 60a, and the thickness d of the inter mediate layer 5b as shown in Table 11 below. Other structures were similar to those of Sample 135. Electrical resistance between the first sensor electrode 40a and the measured gas side wiring 20, and sensor output were studied for each sample. The results are shown in Table 12. Judgment criteria are the same as those in Example 1 and indicated using ○ and x.

TABLE 11 standard: 0.01 mm ≤ A ≤ 1.315 mm, 0.02 mm ≤ B ≤ 2.63 mm,
B ≥ 2A, 0.01 mm ≤ d ≤ 0.1 mm

| Sample | TH diameter A | Diameter of the intermediate layer B | B/A | Thickness of the intermediate layer: d |
|---|---|---|---|---|
| 137 | 0.005 | 0.005 | 1.00 | 0.005 |
| 138 | 0.005 | 0.01 | 2.00 | 0.005 |
| 139 | 0.01 | 0.01 | 1.00 | 0.005 |
| 140 | 0.5 | 0.5 | 1.00 | 0.005 |
| 141 | 1 | 1 | 1.00 | 0.005 |
| 142 | 1.315 | 1.315 | 1.00 | 0.005 |
| 143 | 0.01 | 0.02 | 2.00 | 0.005 |
| 144 | 0.01 | 1 | 100.00 | 0.005 |
| 145 | 0.01 | 2.63 | 263.00 | 0.005 |
| 146 | 0.5 | 1 | 2.00 | 0.005 |
| 147 | 0.5 | 2.63 | 5.26 | 0.005 |
| 148 | 1 | 2 | 2.00 | 0.005 |
| 149 | 1 | 2.63 | 2.63 | 0.005 |
| 150 | 1.315 | 2.63 | 2.00 | 0.005 |
| 151 | 0.005 | 0.005 | 1.00 | 0.01 |
| 152 | 0.005 | 0.01 | 2.00 | 0.01 |
| 153 | 0.01 | 0.01 | 1.00 | 0.01 |
| 154 | 0.5 | 0.5 | 1.00 | 0.01 |
| 155 | 1 | 1 | 1.00 | 0.01 |
| 156 | 1.315 | 1.315 | 1.00 | 0.01 |
| 157 | 0.01 | 0.02 | 2.00 | 0.01 |
| 158 | 0.01 | 1 | 100.00 | 0.01 |
| 159 | 0.01 | 2.63 | 263.00 | 0.01 |
| 160 | 0.5 | 1 | 2.00 | 0.01 |
| 161 | 0.5 | 2.63 | 5.26 | 0.01 |
| 162 | 1 | 2 | 2.00 | 0.01 |
| 163 | 1 | 2.63 | 2.63 | 0.01 |
| 164 | 1.315 | 2.63 | 2.00 | 0.01 |
| 165 | 0.01 | 0.02 | 2.00 | 0.05 |
| 166 | 0.01 | 1 | 100.00 | 0.05 |
| 167 | 0.01 | 2.63 | 263.00 | 0.05 |
| 168 | 0.5 | 1 | 2.00 | 0.05 |
| 169 | 0.5 | 2.63 | 5.26 | 0.05 |
| 170 | 1 | 2 | 2.00 | 0.05 |
| 171 | 1 | 2.63 | 2.63 | 0.05 |
| 172 | 1.315 | 2.63 | 2.00 | 0.05 |
| 173 | 0.01 | 0.02 | 2.00 | 0.1 |
| 174 | 0.01 | 1 | 100.00 | 0.1 |
| 175 | 0.01 | 2.63 | 263.00 | 0.1 |

TABLE 11-continued standard: 0.01 mm ≤ A ≤ 1.315 mm, 0.02 mm ≤ B ≤ 2.63 mm,
B ≥ 2A, 0.01 mm ≤ d ≤ 0.1 mm

| Sample | TH diameter A | Diameter of the intermediate layer B | B/A | Thickness of the intermediate layer: d |
|---|---|---|---|---|
| 176 | 0.5 | 1 | 2.00 | 0.1 |
| 177 | 0.5 | 2.63 | 5.26 | 0.1 |
| 178 | 1 | 2 | 2.00 | 0.1 |
| 179 | 1 | 2.63 | 2.63 | 0.1 |
| 180 | 1.315 | 2.63 | 2.00 | 0.1 |
| 181 | 0.01 | 0.02 | 2.00 | 0.11 |
| 182 | 1.315 | 2.63 | 2.00 | 0.11 |
| 183 | 0.01 | 2.64 | 264.00 | 0.01 |
| 184 | 0.01 | 2.64 | 264.00 | 0.1 |
| 185 | 0.01 | 2.64 | 264.00 | 1.1 |
| 186 | 0.5 | 2.64 | 5.28 | 0.01 |
| 187 | 0.5 | 2.64 | 5.28 | 0.1 |
| 188 | 0.5 | 2.64 | 5.28 | 1.1 |
| 189 | 1 | 2.64 | 2.64 | 0.01 |
| 190 | 1 | 2.64 | 2.64 | 0.1 |
| 191 | 1 | 2.64 | 2.64 | 1.1 |
| 192 | 1.315 | 2.64 | 2.01 | 0.01 |
| 193 | 1.315 | 2.64 | 2.01 | 0.1 |
| 194 | 1.315 | 2.64 | 2.01 | 1.1 |
| 195 | 1.32 | 2.64 | 2.00 | 0.005 |
| 196 | 1.32 | 2.64 | 2.00 | 0.01 |
| 197 | 1.32 | 2.64 | 2.00 | 0.1 |
| 198 | 1.32 | 2.64 | 2.00 | 1.1 |

TABLE 12

| Sample | Judgement Connection reliability | Judgement Sensor output |
|---|---|---|
| 137 | x | x |
| 138 | x | x |
| 139 | x | x |
| 140 | x | x |
| 141 | x | x |
| 142 | x | x |
| 143 | x | x |
| 144 | x | x |
| 145 | x | x |
| 146 | x | x |
| 147 | x | x |
| 148 | x | x |
| 149 | x | x |
| 150 | x | x |
| 151 | x | x |
| 152 | x | x |
| 153 | x | x |
| 154 | x | x |
| 155 | x | x |
| 156 | x | x |
| 157 | ○ | ○ |
| 158 | ○ | ○ |
| 159 | ○ | ○ |
| 160 | ○ | ○ |
| 161 | ○ | ○ |
| 162 | ○ | ○ |
| 163 | ○ | ○ |
| 164 | ○ | ○ |
| 165 | ○ | ○ |
| 166 | ○ | ○ |
| 167 | ○ | ○ |
| 168 | ○ | ○ |
| 169 | ○ | ○ |
| 170 | ○ | ○ |
| 171 | ○ | ○ |
| 172 | ○ | ○ |
| 173 | ○ | ○ |
| 174 | ○ | ○ |
| 175 | ○ | ○ |
| 176 | ○ | ○ |
| 177 | ○ | ○ |
| 178 | ○ | ○ |
| 179 | ○ | ○ |
| 180 | ○ | ○ |
| 181 | x | x |
| 182 | x | x |
| 183 | x | x |
| 184 | x | x |
| 185 | x | x |
| 186 | x | x |
| 187 | x | x |
| 188 | x | x |
| 189 | x | x |
| 190 | x | x |
| 191 | x | x |
| 192 | x | x |
| 193 | x | x |
| 194 | x | x |
| 195 | x | x |
| 196 | x | x |
| 197 | x | x |
| 198 | x | x |

Table 11 and Table 12 indicate that samples having the following ranges have favorable connection reliability and sensor output: 0.01 mm≤A≤1.315 mm, 0.02 mm≤B2.63 mm, B/A≥2, and 0.01 mm≤d≤0.1 mm.

Next, Sample 199 to Sample 201 were manufactured by changing the Pt/Pd composition (see Table 13) of the first metal material. Other material compositions and structures were the same as those of Sample 135. The electrical resistance between the first sensor electrode 40a and the measured gas side wiring 20, and sensor output were studied for each sample. The results are shown in Table 13. Judgment criteria are the same as those in Example 1 and indicated using ○ and x.

TABLE 13

| Sample | Pt/Pd Composition ratio (wt %) | Judgement Connection reliability | Judgement Sensor output |
|---|---|---|---|
| 199 | 90/10 | ○ | ○ |
| 200 | 50/50 | ○ | ○ |
| 201 | 10/90 | ○ | ○ |

Table 13 indicates that even when the Pt/Pd composition ratio of the first metal material is changed between 90/10 and 10/90, connection reliability between the first sensor electrode 40a and the measured gas side wiring 20, and sensor output in Sample 199 to Sample 201 are favorable.

Tenth Embodiment

FIG. 25

According to a tenth embodiment, the connection structure of the electrode terminal 4 and the wiring layer 2 is the same as that of the gas sensor element 1 according to the third embodiment (FIG. 18). The material of the heater section 14 is changed.

Figure 25:
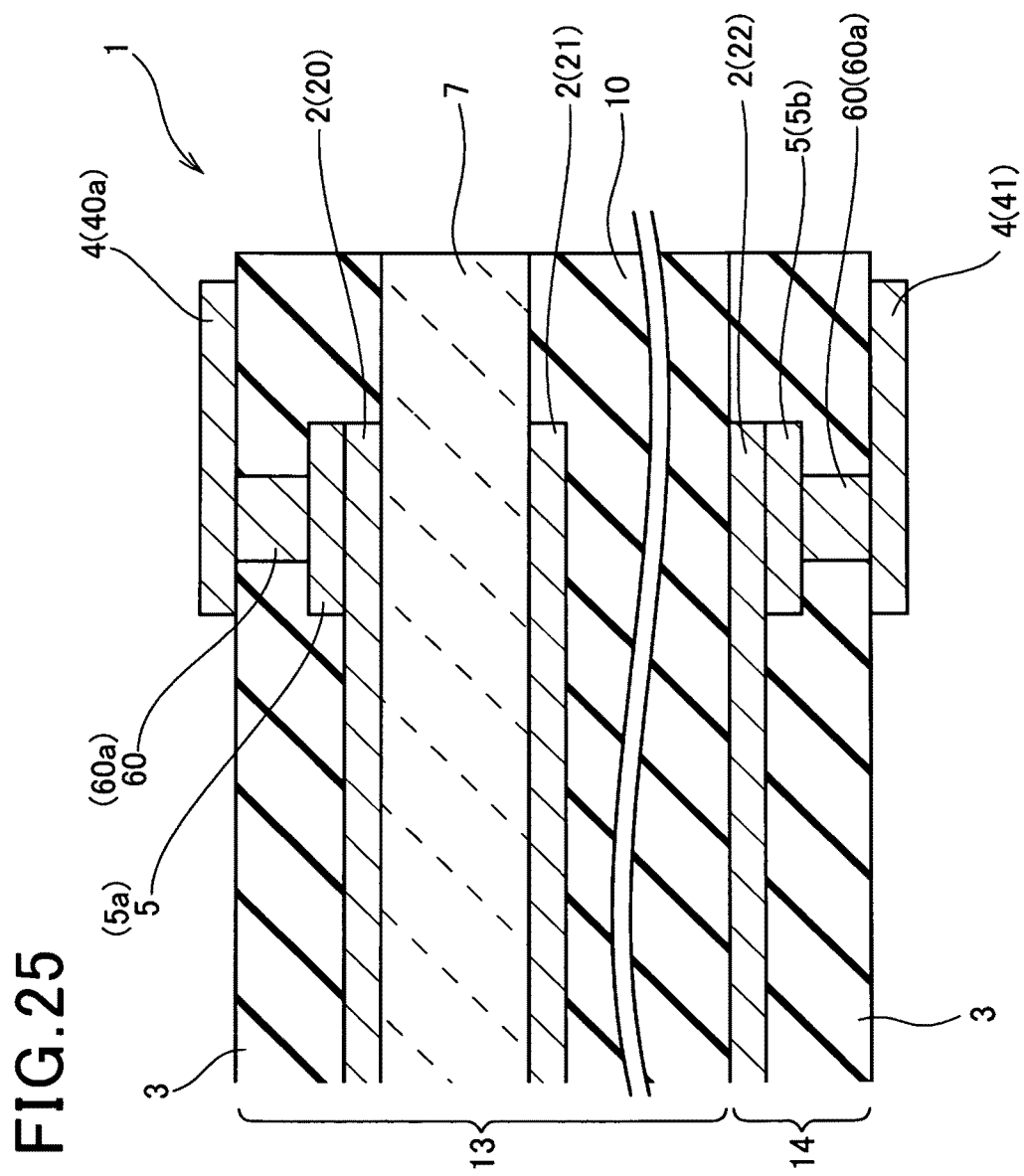
FIG. 25 is a cross-sectional view of a gas sensor element passing through a first sensor electrode 40a before firing according to a tenth embodiment of the present invention.

Specifically, as shown in FIG. 25, the difference with the gas sensor element 1 according to the third embodiment (FIG. 18) is that the heater wiring 2, and the intermediate layer 5b are composed of the first metal material.

Other configurations are similar to those according to the above-described first embodiment. Therefore, explanations thereof are omitted.

According to the tenth embodiment, the same operational effects as those according to the first embodiment can be achieved.

Eleventh Embodiment

FIG. 26

According to an eleventh embodiment, the connection structure of the electrode terminal 4 and the wiring layer 2 is the same as that of the gas sensor element 1 according to the fourth embodiment (FIG. 19). The material of the heater section 14 is changed.

Figure 26:
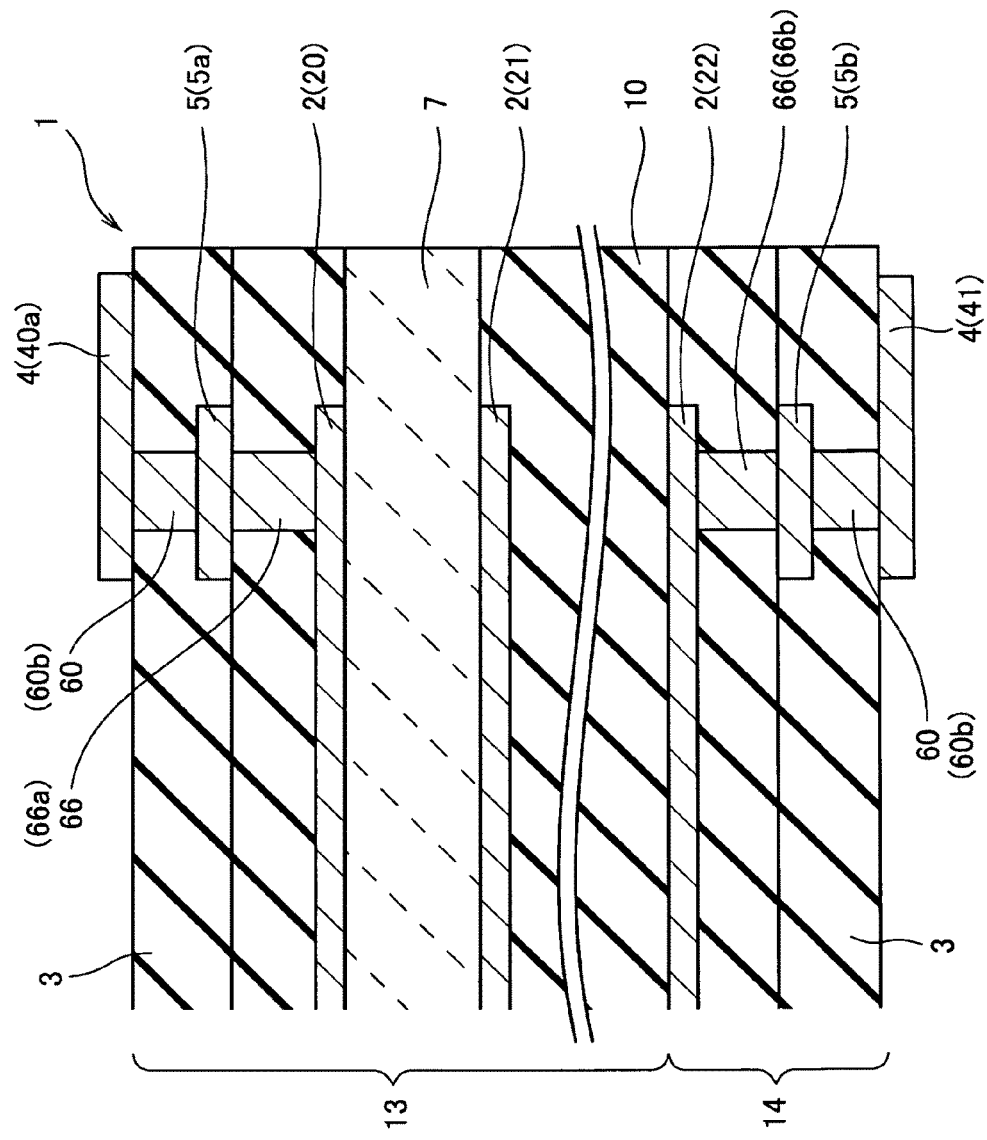
FIG. 26 is a cross-sectional view of a gas sensor element passing through a first sensor electrode 40a before firing according to an eleventh embodiment of the present invention.

Specifically, as shown in FIG. 26, the difference with the gas sensor element 1 according to the fourth embodiment (FIG. 19) is that the heater wiring 22, the heater side second connecting member 66b, and the intermediate layer 5b are composed of the first metal material.

Other configurations are similar to those according to the above-described first embodiment. Therefore, explanations thereof are omitted.

According to the eleventh embodiment, the same operational effects as those according to the first embodiment can be achieved.

Twelfth Embodiment

FIG. 27

According to a twelfth embodiment, the connection structure of the electrode terminal 4 and the wiring layer 2 is the same as that of the gas sensor element 1 according to the second embodiment (FIG. 16). The material of the heater section 14 is changed.

Figure 27:
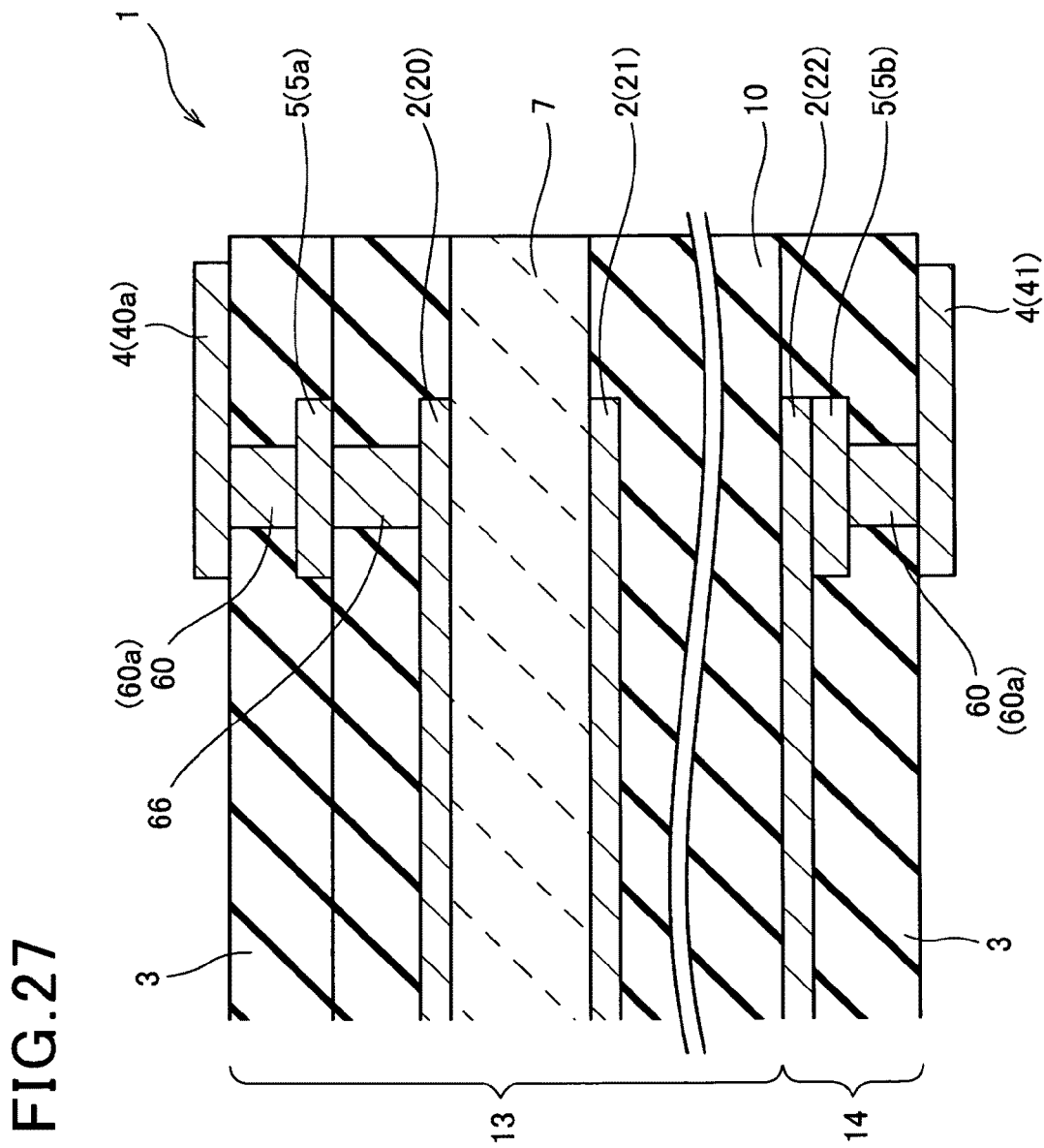
FIG. 27 is a cross-sectional view of a gas sensor element passing through a first sensor electrode 40a before firing according to a twelfth embodiment of the present invention.

Specifically, as shown in FIG. 27, the difference with the gas sensor element 1 in FIG. 16 is that the heater wiring 22, and the intermediate layer 5b are composed of the first metal material.

Other configurations are similar to those according to the above-described first embodiment. Therefore, explanations thereof are omitted.

According to the twelfth embodiment, the same operational effects as those according to the first embodiment can be achieved.

Thirteenth Embodiment

Figure 28:
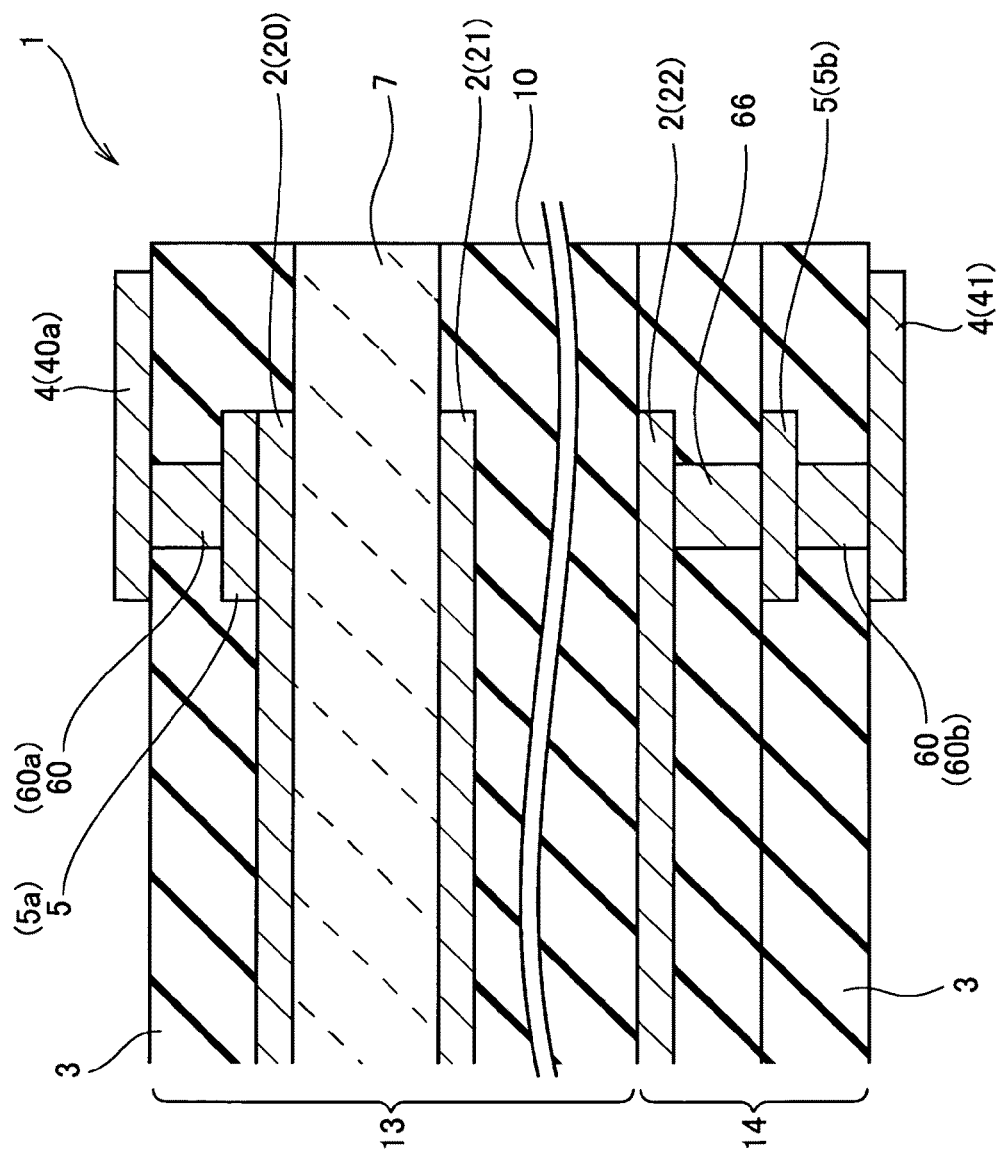
FIG. 28 is a cross-sectional view of a gas sensor element passing through a first sensor electrode 40a before firing according to a thirteenth embodiment of the present invention.
Figure 29:
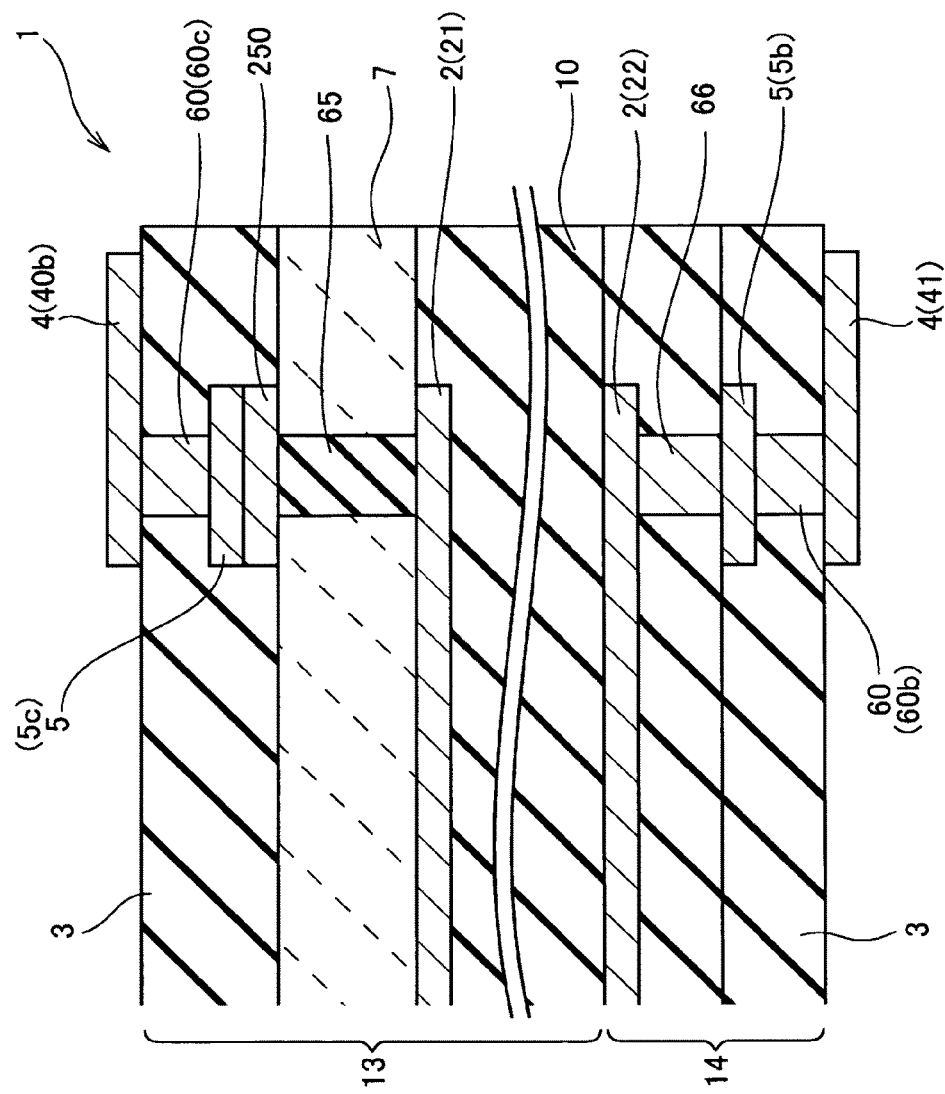
FIG. 29 is a cross-sectional view of a gas sensor element passing through a second sensor electrode 40b before firing according to a thirteenth embodiment of the present invention.

FIG. 28 and FIG. 29

According to a thirteenth embodiment, the connection structure of the electrode terminal 4 and the wiring layer 2 is the same as that of the gas sensor element 1 according to the first embodiment (FIG. 4 and FIG. 5). The material of the sensor section 13 is changed.

Specifically, the gas sensor element 1 shown in FIG. 28 has the same configuration as the gas sensor element 1 shown in FIG. 4. The difference with the gas sensor element 1 in FIG. 4 is that the reference gas side wiring 21 of the sensor section 13 is composed of the first metal material.

In addition, the gas sensor 1 in FIG. 29 has the same configuration as the gas sensor element 1 in FIG. 5. The difference with the gas sensor element 1 in FIG. 5 is that the intermediate layer 5c, the connecting layer 250, the sensor side second connecting member 65, and the reference gas side wiring 21 are composed of the first metal material.

Other configurations are similar to those according to the above-described first embodiment. Therefore, explanations thereof are omitted.

According to the thirteenth embodiment, the same operational effects as those according to the first embodiment can be achieved.

Example 4

In Example 4, a sample was manufactured having a similar structure as the gas sensor element 1 according to the thirteenth embodiment (FIG. 28, FIG. 29) by stacking the electrode terminal 4, the insulating layer 3, the intermediate layer 5, and the like.

The first sensor electrode 40a, the connecting member 60a, the reference gas side wiring 21, the first connecting member 60b, the heater electrode 41, the second sensor electrode 40b, the sensor side first connecting member 60c, the intermediate layer 5c, the connecting layer 250 and the sensor side second connecting member 65 were composed of the first metal material. The intermediate layer 5a, the measured gas side wiring 20, the heater wiring 22, the second connecting member 66 and the intermediate layer 5b were composed of the second metal material having a lower melting point than the first metal material.

Respective dimensions of the electrode terminal 4, the connecting member 60, the intermediate layers 5a and 5b, the wiring layers 20, 21, and 22, the insulating layer 3, the first heater substrate 31a, and the second heater substrate 31b are the same as those in Sample 1 in Example 1. The obtained sample is Sample 202 of the gas sensor element in Example 3. As a comparative example, Sample 203 was used having the same configuration as Sample 2 manufactured in Example 1.

Subsequently, Sample 202 and Sample 203 were fired for 120 minutes at 1450±50° C. A plurality of fired Samples 202 and Samples 203 were manufactured. Under the same conditions as those in Example 1, electrical resistance between the first sensor electrode 40a and the measured gas side wiring 20 were measured, and the atmospheric IL value was measured. The number of measured samples was 50 samples each. From the measurement results, connection reliability between the heater electrode 41 and the heater wiring 22 and sensor output were judged. The results are shown in Table 14. Judgment criteria are the same as those in Example 1 and indicated using ○ and x.

TABLE 14

| Sample | Judgement | |
|---|---|---|
|  | Connection reliability | Sensor output |
| 202 | ○ | ○ |
| 203 | x | x |

As shown in Table 14, Sample 202 has favorable connection reliability and sensor output. Neither connection reliability nor sensor output is favorable in Sample 203 of the comparative example.

Next, Sample 204 to Sample 265 were manufactured by changing the ratio B/A of the outer diameter B of the intermediate layer 5b and the outer diameter A of the connecting member 60a, and the thickness d of the intermediate layer 5b as shown in Table 15 below. Other structures were similar to those of Sample 202. Electrical resistance between the heater wiring 22 and the heater electrode 41, and sensor output were studied for each sample. The results are shown in Table 16. Judgment criteria are the same as those in Example 1 and indicated using o and x.

TABLE 15 standard: 0.01 mm ≤ A ≤ 1.315 mm, 0.02 mm ≤ B ≤ 2.63 mm, B ≥ 2A, 0.01 mm ≤ d ≤ 0.1 mm

| Sample | TH Diameter: A | Diameter of the intermediate layer: B | B/A | Thickness of the intermediate layer: d |
|---|---|---|---|---|
| 204 | 0.005 | 0.005 | 1.00 | 0.005 |
| 205 | 0.005 | 0.01 | 2.00 | 0.005 |
| 206 | 0.01 | 0.01 | 1.00 | 0.005 |
| 207 | 0.5 | 0.5 | 1.00 | 0.005 |
| 208 | 1 | 1 | 1.00 | 0.005 |
| 209 | 1.315 | 1.315 | 1.00 | 0.005 |
| 210 | 0.01 | 0.02 | 2.00 | 0.005 |
| 211 | 0.01 | 1 | 100.00 | 0.005 |
| 212 | 0.01 | 2.63 | 263.00 | 0.005 |
| 213 | 0.5 | 1 | 2.00 | 0.005 |
| 214 | 0.5 | 2.63 | 5.26 | 0.005 |
| 215 | 1 | 2 | 2.00 | 0.005 |
| 216 | 1 | 2.63 | 2.63 | 0.005 |
| 217 | 1.315 | 2.63 | 2.00 | 0.005 |
| 218 | 0.005 | 0.005 | 1.00 | 0.01 |
| 219 | 0.005 | 0.01 | 2.00 | 0.01 |
| 220 | 0.01 | 0.01 | 1.00 | 0.01 |
| 221 | 0.5 | 0.5 | 1.00 | 0.01 |
| 222 | 1 | 1 | 1.00 | 0.01 |
| 223 | 1.315 | 1.315 | 1.00 | 0.01 |
| 224 | 0.01 | 0.02 | 2.00 | 0.01 |
| 225 | 0.01 | 1 | 100.00 | 0.01 |
| 226 | 0.01 | 2.63 | 263.00 | 0.01 |
| 227 | 0.5 | 1 | 2.00 | 0.01 |
| 228 | 0.5 | 2.63 | 5.26 | 0.01 |
| 229 | 1 | 2 | 2.00 | 0.01 |
| 230 | 1 | 2.63 | 2.63 | 0.01 |
| 231 | 1.315 | 2.63 | 2.00 | 0.01 |
| 232 | 0.01 | 0.02 | 2.00 | 0.05 |
| 233 | 0.01 | 1.00 | 100.00 | 0.05 |
| 234 | 0.01 | 2.63 | 263.00 | 0.05 |
| 235 | 0.50 | 1.00 | 2.00 | 0.05 |
| 236 | 0.50 | 2.63 | 5.26 | 0.05 |
| 237 | 1.00 | 2.00 | 2.00 | 0.05 |
| 238 | 1.00 | 2.63 | 2.63 | 0.05 |
| 239 | 1.32 | 2.63 | 2.00 | 0.05 |
| 240 | 0.01 | 0.02 | 2.00 | 0.1 |
| 241 | 0.01 | 1 | 100.00 | 0.1 |
| 242 | 0.01 | 2.63 | 263.00 | 0.1 |
| 243 | 0.5 | 1 | 2.00 | 0.1 |
| 244 | 0.5 | 2.63 | 5.26 | 0.1 |
| 245 | 1 | 2 | 2.00 | 0.1 |
| 246 | 1 | 2.63 | 2.63 | 0.1 |
| 247 | 1.315 | 2.63 | 2.00 | 0.1 |
| 248 | 0.01 | 0.02 | 2.00 | 0.11 |
| 249 | 1.315 | 2.63 | 2.00 | 0.11 |
| 250 | 0.01 | 2.64 | 264.00 | 0.01 |
| 251 | 0.01 | 2.64 | 264.00 | 0.1 |
| 252 | 0.01 | 2.64 | 264.00 | 1.1 |
| 253 | 0.5 | 2.64 | 5.28 | 0.01 |
| 254 | 0.5 | 2.64 | 5.28 | 0.1 |
| 255 | 0.5 | 2.64 | 5.28 | 1.1 |
| 256 | 1 | 2.64 | 2.64 | 0.01 |
| 257 | 1 | 2.64 | 2.64 | 0.1 |
| 258 | 1 | 2.64 | 2.64 | 1.1 |
| 259 | 1.315 | 2.64 | 2.01 | 0.01 |
| 260 | 1.315 | 2.64 | 2.01 | 0.1 |
| 261 | 1.315 | 2.64 | 2.01 | 1.1 |
| 262 | 1.32 | 2.64 | 2.00 | 0.005 |
| 263 | 1.32 | 2.64 | 2.00 | 0.01 |
| 264 | 1.32 | 2.64 | 2.00 | 0.1 |
| 265 | 1.32 | 2.64 | 2.00 | 1.1 |

TABLE 16

| Sample | Judgement Connection reliability | Sensor output |
|---|---|---|
| 204 | x | x |
| 205 | x | x |
| 206 | x | x |
| 207 | x | x |
| 208 | x | x |
| 209 | x | x |
| 210 | x | x |
| 211 | x | x |
| 212 | x | x |
| 213 | x | x |
| 214 | x | x |
| 215 | x | x |
| 216 | x | x |
| 217 | x | x |
| 218 | x | x |
| 219 | x | x |
| 220 | x | x |
| 221 | x | x |
| 222 | x | x |
| 223 | x | x |
| 224 | o | o |
| 225 | o | o |
| 226 | o | o |
| 227 | o | o |
| 228 | o | o |
| 229 | o | o |
| 230 | o | o |
| 231 | o | o |
| 232 | o | o |
| 233 | o | o |
| 234 | o | o |
| 235 | o | o |
| 236 | o | o |
| 237 | o | o |
| 238 | o | o |
| 239 | o | o |
| 240 | o | o |
| 241 | o | o |
| 242 | o | o |
| 243 | o | o |
| 244 | o | o |
| 245 | o | o |
| 246 | o | o |
| 247 | o | o |
| 248 | x | x |
| 249 | x | x |
| 250 | x | x |
| 251 | x | x |
| 252 | x | x |
| 253 | x | x |
| 254 | x | x |
| 255 | x | x |
| 256 | x | x |
| 257 | x | x |
| 258 | x | x |
| 259 | x | x |
| 260 | x | x |
| 261 | x | x |
| 262 | x | x |
| 263 | x | x |
| 264 | x | x |
| 265 | x | x |

Table 15 and Table 16 indicate that samples having the following ranges have favorable connection reliability and sensor output: 0.01 mm≤A≤1.315 mm, 0.02 mm≤B≤2.63 mm, B/A≥2, and 0.01 mm≤d≤0.1 mm.

Next, Sample 266 to Sample 268 were manufactured by changing the Pt/Pd composition (see Table 17) of the first metal material. Other material compositions and structures were the same as those of Sample 202. The electrical resistance between the first sensor electrode 40a and the measured gas side wiring 20, and sensor output were studied for each sample. The results are shown in Table 17. Judgment criteria are the same as those in Example 1 and indicated using ○ and x.

TABLE 17

| Sample | Pt/Pd Composition ratio (wt %) | Judgement Connection reliability | Sensor output |
|---|---|---|---|
| 266 | 90/10 | ○ | ○ |
| 267 | 50/50 | ○ | ○ |
| 268 | 10/90 | ○ | ○ |

Table 17 indicates that even when the Pt/Pd composition ratio of the first metal material is changed between 90/10 and 10/90, connection reliability between the first sensor electrode 40a and the measured gas side wiring 20, and sensor output in Sample 266 to Sample 268 are favorable.

Fourteenth Embodiment

FIG. 30

According to a fourteenth embodiment, the connection structure of the electrode terminal 4 and the wiring layer 2 is the same as that of the gas sensor element 1 according to the fourth embodiment (FIG. 19). The material of the sensor section 13 is changed.

Figure 30:
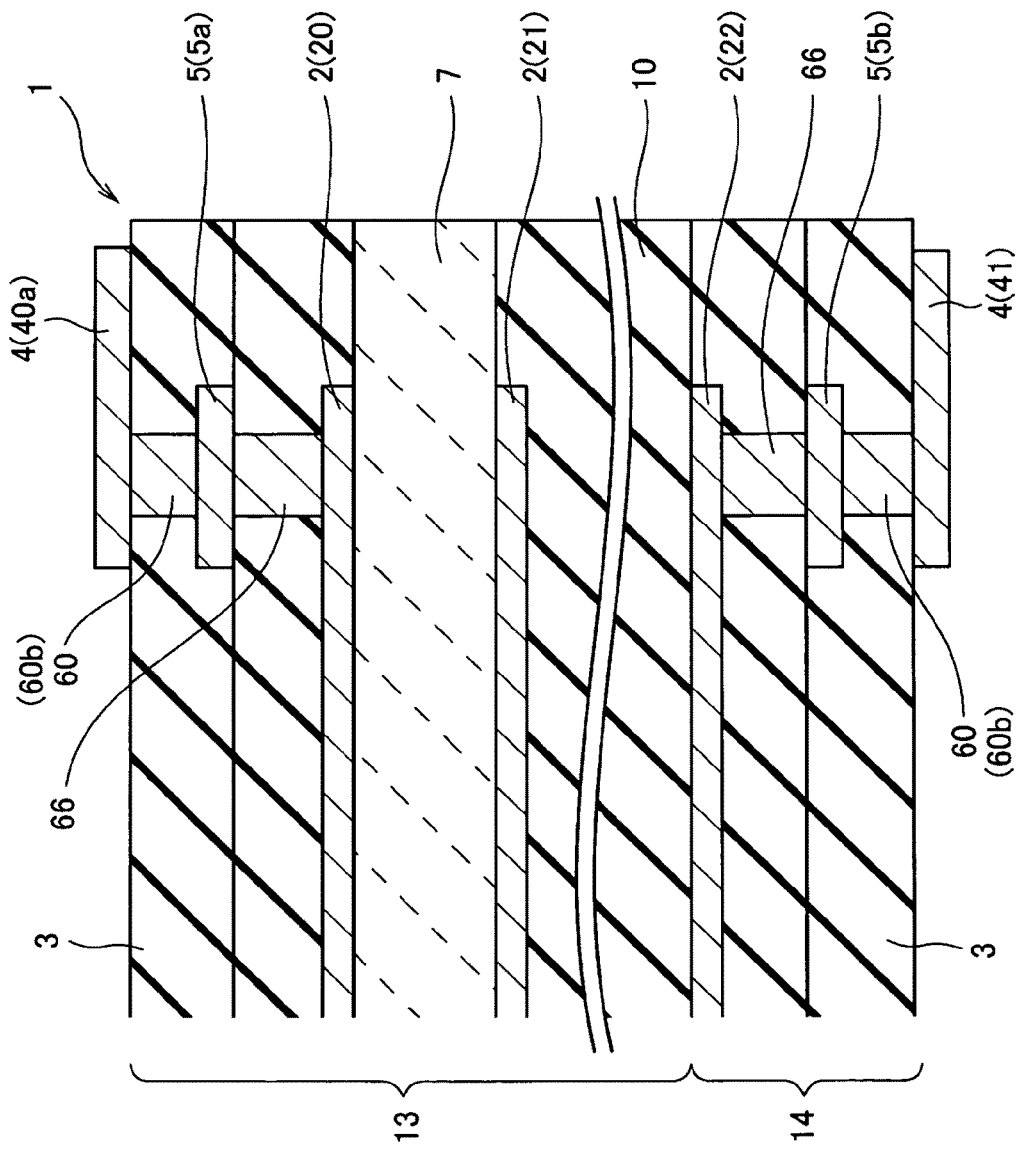
FIG. 30 is a cross-sectional view of a gas sensor element passing through a first sensor electrode 40a before firing according to a fourteenth embodiment of the present invention.

Specifically, as shown in FIG. 30, the difference with the gas sensor element 1 in FIG. 19 is that the reference gas side wiring 21 of the sensor section 13 is composed of the first metal material.

Other configurations are similar to those according to the above-described first embodiment. Therefore, explanations thereof are omitted.

According to the fourteenth embodiment, the same operational effects as those according to the first embodiment can be achieved.

Fifteenth Embodiment

FIG. 31

According to a fifteenth embodiment, the connection structure of the electrode terminal 4 and the wiring layer 2 is the same as that of the gas sensor element 1 according to the third embodiment (FIG. 18). The material of the sensor section 13 is changed.

Figure 31:
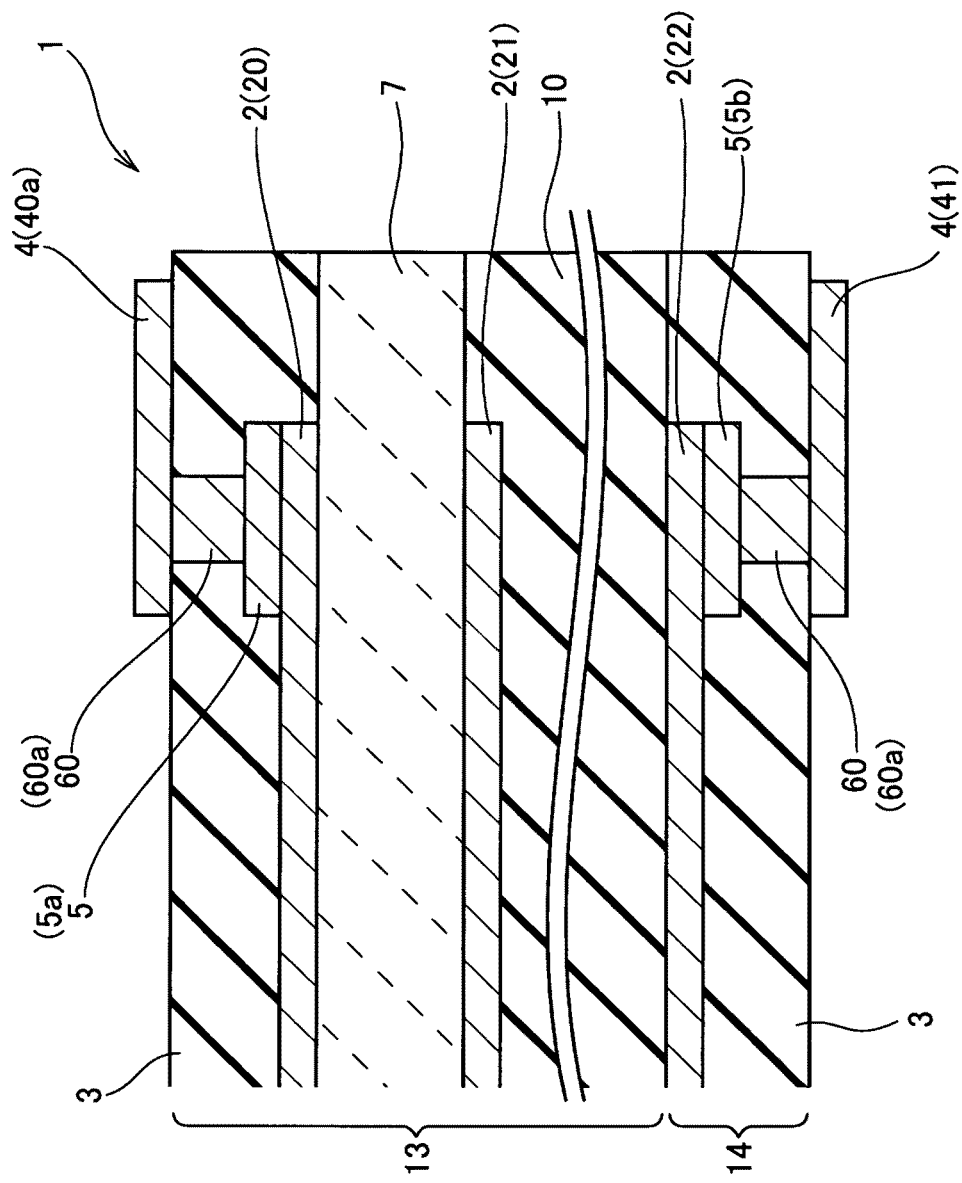
FIG. 31 is a cross-sectional view of a gas sensor element passing through a first sensor electrode 40a before firing according to a fifteenth embodiment of the present invention.

Specifically, as shown in FIG. 31, the difference with the gas sensor element 1 in FIG. 18 is that the reference gas side wiring 21 of the sensor section 13 is composed of the first metal material.

Other configurations are similar to those according to the first embodiment and, therefore, descriptions thereof are omitted.

According to the fifteenth embodiment, operational effects similar to those according to the first embodiment can be achieved.

Sixteenth Embodiment

FIG. 32

According to a sixteenth embodiment, the connection structure of the electrode terminal 4 and the wiring layer 2 is the same as that of the gas sensor element 1 according to the second embodiment (FIG. 16). The material of the sensor section 13 is changed.

Figure 32:
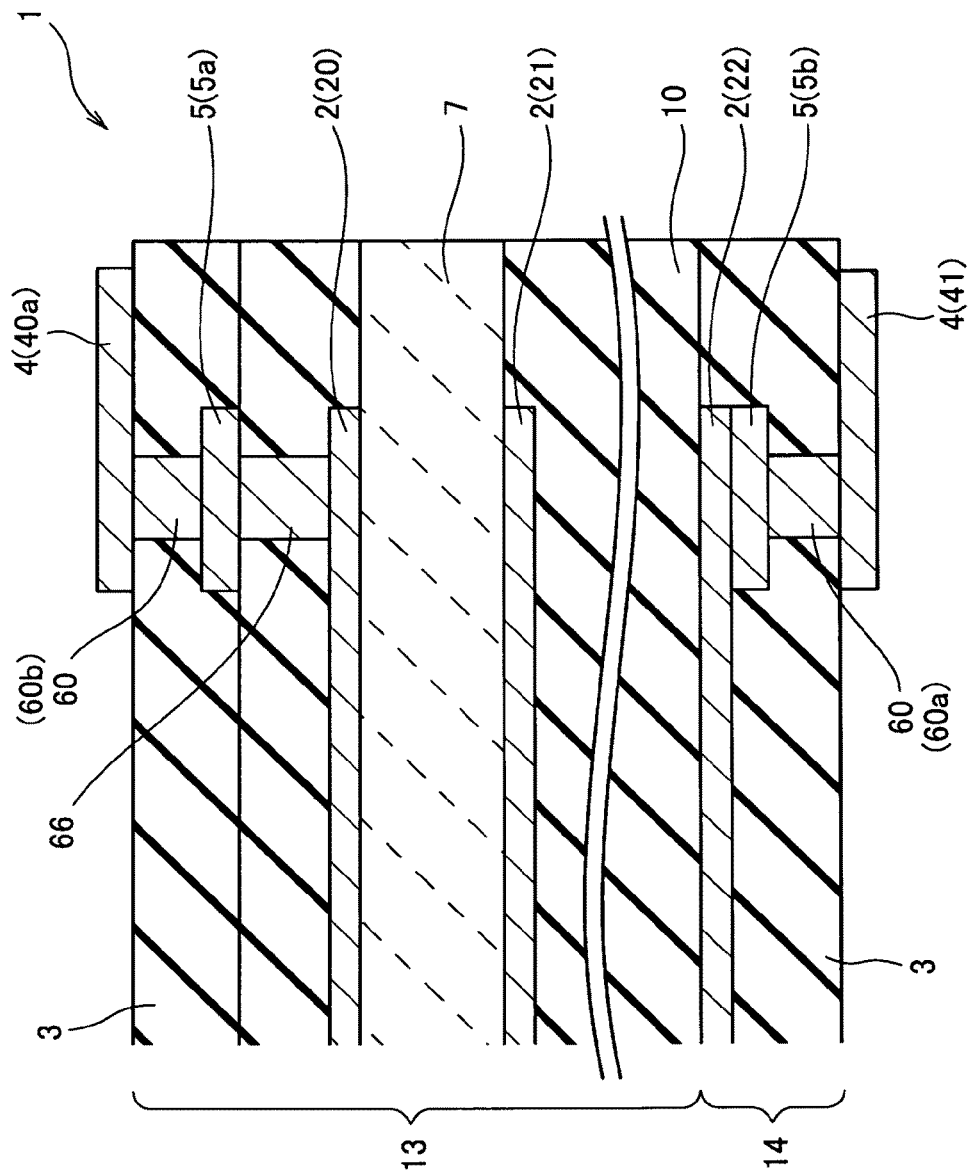
FIG. 32 is a cross-sectional view of a gas sensor element passing through a first sensor electrode 40a before firing according to a sixteenth embodiment of the present invention.

Specifically, as shown in FIG. 32, the difference with the gas sensor element 1 in FIG. 16 is that the reference gas side wiring 21 of the sensor section 13 is composed of the first metal material.

Other configurations are similar to those according to the first embodiment and, therefore, descriptions thereof are omitted.

According to the sixteenth embodiment, operational effects similar to those according to the first embodiment can be achieved.

Seventeenth Embodiment

Figure 33:
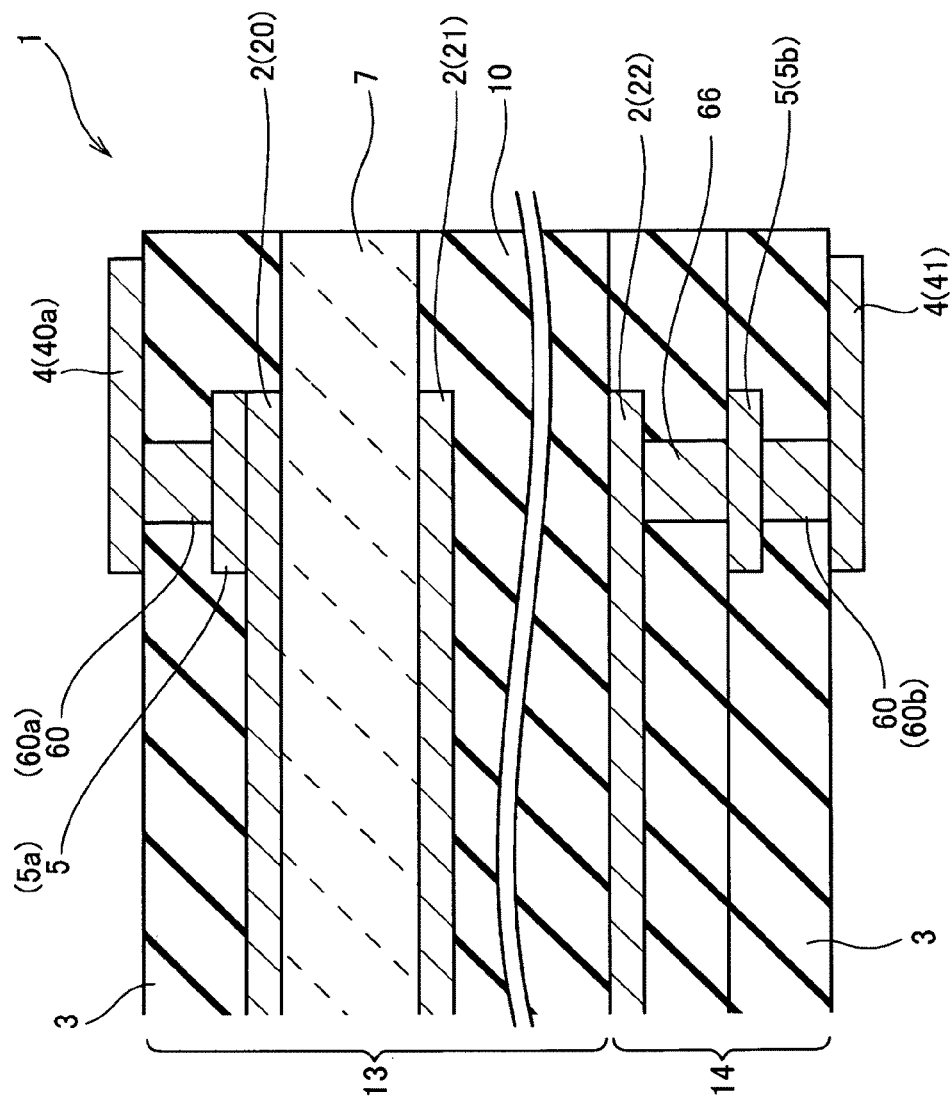
FIG. 33 is a cross-sectional view of a gas sensor element passing through a first sensor electrode 40a before firing according to a seventeenth embodiment of the present invention.
Figure 34:
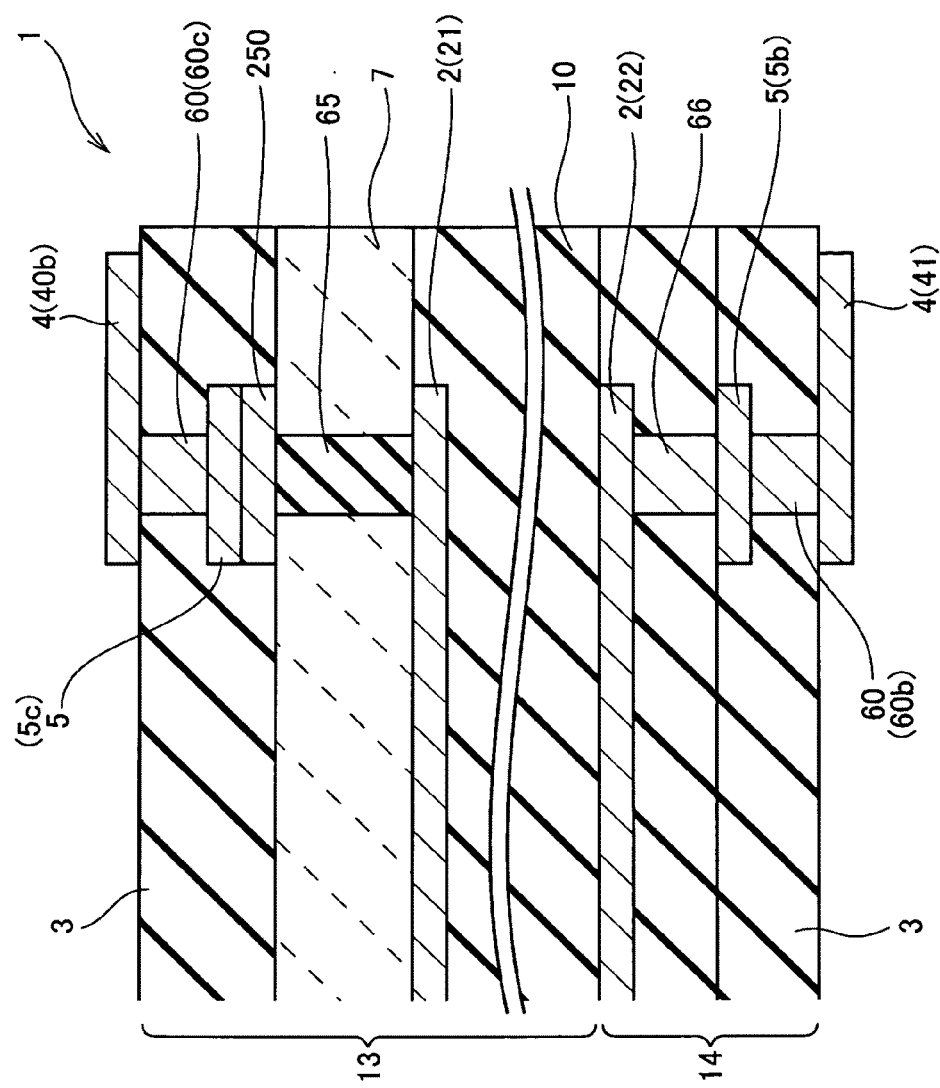
FIG. 34 is a cross-sectional view of a gas sensor element passing through a second sensor electrode 40b before firing according to a seventeenth embodiment of the present invention.

FIG. 33 and FIG. 34

According to a seventeenth embodiment, the connection structure of the electrode terminal 4 and the wiring layer 2 is the same as that of the gas sensor element 1 according to the first embodiment (FIG. 4 and FIG. 5). The material of the sensor section 13 is changed.

Specifically, the configuration of the gas sensor element 1 in FIG. 33 is the same as that of the gas sensor element 1 in FIG. 4. The difference with the gas sensor element 1 in FIG. 4 is that the intermediate layer 5a and the measured gas side wiring 20 of the sensor section 13 are composed of the first metal material.

The gas sensor element 1 in FIG. 34 has the same configuration and uses the same materials as the gas sensor element 1 shown in FIG. 5.

Other configurations are similar to those according to the first embodiment and, therefore, descriptions thereof are omitted.

According to the seventeenth embodiment, operational effects similar to those according to the first embodiment can be achieved.

Example 5

In Example 5, a sample was manufactured having a similar structure as the gas sensor element 1 according to the seventeenth embodiment (FIG. 33, FIG. 34) by stacking the electrode terminal 4, the insulating layer 3, the intermediate layer 5, and the like.

The first sensor electrode 40a, the connecting member 60a, the intermediate layer 5a, the measured gas side wiring 20, the first connecting member 60b, the heater electrode 41, the second sensor electrode 40b, and the sensor side first connecting member 60e were composed of the first metal material. The reference gas side wiring 21, the heater wiring 22, the second connecting member 66, the intermediate layers 5b and 5c, the connecting layer 250 and the sensor side second connecting member 65 were composed of the second metal material having a lower melting point than the first metal material. The composition of the first metal material and the second metal material is the same as those of the Example 1.

Respective dimensions of the electrode terminal 4, the connecting member 60, the intermediate layers 5a and 5b, the wiring layers 20, 21, and 22, the insulating layer 3, the first heater substrate 31a, and the second heater substrate 31b are the same as those in Sample 1 in Example 1. The obtained sample is Sample 269 of the gas sensor element in Example 5. As a comparative example, Sample 270 was used having the same configuration as Sample 2 manufactured in Example 1.

Subsequently, Sample 269 and Sample 270 were fired for 120 minutes at 1450±50° C. A plurality of fired Samples 269 and Samples 270 were manufactured. Under the same conditions as those in Example 1, electrical resistance between the heater electrode 41 and the heater wiring 22 were measured, and the atmospheric IL value was measured. The number of measured samples was 50 samples each. From the measurement results, connection reliability between the heater electrode 41 and the heater wiring 22 and sensor output were judged. The results are shown in Table 18. Judgment criteria are the same as those in Example 1 and indicated using ○ and x.

TABLE 18

| Sample | Judgement Connection reliability | Sensor output |
|---|---|---|
| 269 | ○ | ○ |
| 270 | x | x |

As shown in Table 18, Sample 269 has favorable connection reliability and sensor output. Neither connection reliability nor sensor output is favorable in Sample 270 of the comparative example.

Next, Sample 271 to Sample 332 were manufactured by changing the ratio B/A of the outer diameter B of the intermediate layer 5b and the outer diameter A of the connecting member 60a, and the thickness d of the intermediate layer 5a as shown in Table 19 below. Other structures were similar to those of Sample 269.

TABLE 19 standard: 0.01 mm ≤ A ≤ 1.315 mm, 0.02 mm ≤ B ≤ 2.63 mm, B ≥ 2A, 0.01 mm ≤ d ≤ 0.1 mm

| Sample | TH diameter: A | Diameter of the intermediate layer: B | B/A | Thickness of the intermediate layer: d |
|---|---|---|---|---|
| 271 | 0.005 | 0.005 | 1.00 | 0.005 |
| 272 | 0.005 | 0.01 | 2.00 | 0.005 |
| 273 | 0.01 | 0.01 | 1.00 | 0.005 |
| 274 | 0.5 | 0.5 | 1.00 | 0.005 |
| 275 | 1 | 1 | 1.00 | 0.005 |
| 276 | 1.315 | 1.315 | 1.00 | 0.005 |
| 277 | 0.01 | 0.02 | 2.00 | 0.005 |
| 278 | 0.01 | 1 | 100.00 | 0.005 |
| 279 | 0.01 | 2.63 | 263.00 | 0.005 |
| 280 | 0.5 | 1 | 2.00 | 0.005 |
| 281 | 0.5 | 2.63 | 5.26 | 0.005 |
| 282 | 1 | 2 | 2.00 | 0.005 |
| 283 | 1 | 2.63 | 2.63 | 0.005 |
| 284 | 1.315 | 2.63 | 2.00 | 0.005 |
| 285 | 0.005 | 0.005 | 1.00 | 0.01 |
| 286 | 0.005 | 0.01 | 2.00 | 0.01 |
| 287 | 0.01 | 0.01 | 1.00 | 0.01 |
| 288 | 0.5 | 0.5 | 1.00 | 0.01 |
| 289 | 1 | 1 | 1.00 | 0.01 |
| 290 | 1.315 | 1.315 | 1.00 | 0.01 |
| 291 | 0.01 | 0.02 | 2.00 | 0.01 |
| 292 | 0.01 | 1 | 100.00 | 0.01 |
| 293 | 0.01 | 2.63 | 263.00 | 0.01 |
| 294 | 0.5 | 1 | 2.00 | 0.01 |
| 295 | 0.5 | 2.63 | 5.26 | 0.01 |
| 296 | 1 | 2 | 2.00 | 0.01 |
| 297 | 1 | 2.63 | 2.63 | 0.01 |
| 298 | 1.315 | 2.63 | 2.00 | 0.01 |
| 299 | 0.01 | 0.02 | 2.00 | 0.05 |
| 300 | 0.01 | 1.00 | 100.00 | 0.05 |
| 301 | 0.01 | 2.63 | 263.00 | 0.05 |
| 302 | 0.5 | 1 | 2.00 | 0.05 |
| 303 | 0.5 | 2.63 | 5.26 | 0.05 |

TABLE 19-continued standard: 0.01 mm ≤ A ≤ 1.315 mm, 0.02 mm ≤ B ≤ 2.63 mm, B ≥ 2A, 0.01 mm ≤ d ≤ 0.1 mm

| Sample | TH diameter: A | Diameter of the intermediate layer: B | B/A | Thickness of the intermediate layer: d |
|---|---|---|---|---|
| 304 | 1 | 2 | 2.00 | 0.05 |
| 305 | 1 | 2.63 | 2.63 | 0.05 |
| 306 | 1.315 | 2.63 | 2.00 | 0.05 |
| 307 | 0.01 | 0.02 | 2.00 | 0.1 |
| 308 | 0.01 | 1 | 100.00 | 0.1 |
| 309 | 0.01 | 2.63 | 263.00 | 0.1 |
| 311 | 0.5 | 2.63 | 5.26 | 0.1 |
| 312 | 1 | 2 | 2.00 | 0.1 |
| 313 | 1 | 2.63 | 2.63 | 0.1 |
| 314 | 1.315 | 2.63 | 2.00 | 0.1 |
| 315 | 0.01 | 0.02 | 2.00 | 0.11 |
| 316 | 1.315 | 2.63 | 2.00 | 0.11 |
| 317 | 0.01 | 2.64 | 264.00 | 0.01 |
| 318 | 0.01 | 2.64 | 264.00 | 0.1 |
| 319 | 0.01 | 2.64 | 264.00 | 1.1 |
| 320 | 0.5 | 2.64 | 5.28 | 0.01 |
| 321 | 0.5 | 2.64 | 5.28 | 0.1 |
| 322 | 0.5 | 2.64 | 5.28 | 1.1 |
| 323 | 1 | 2.64 | 2.64 | 0.01 |
| 324 | 1 | 2.64 | 2.64 | 0.1 |
| 325 | 1 | 2.64 | 2.64 | 1.1 |
| 326 | 1.315 | 2.64 | 2.01 | 0.01 |
| 327 | 1.315 | 2.64 | 2.01 | 0.1 |
| 328 | 1.315 | 2.64 | 2.01 | 1.1 |
| 329 | 1.32 | 2.64 | 2.00 | 0.005 |
| 330 | 1.32 | 2.64 | 2.00 | 0.01 |
| 331 | 1.32 | 2.64 | 2.00 | 0.1 |
| 332 | 1.32 | 2.64 | 2.00 | 1.1 |

Electrical resistance between the heater wiring 22 and the heater electrode 41, and sensor output were studied for each sample. The results are shown in Table 20. Judgment criteria are the same as those in Example 1 and indicated using ○ and x,

TABLE 20

| Sample | Judgement Connection reliability | Sensor output |
|---|---|---|
| 271 | x | x |
| 272 | x | x |
| 273 | x | x |
| 274 | x | x |
| 275 | x | x |
| 276 | x | x |
| 277 | x | x |
| 278 | x | x |
| 279 | x | x |
| 280 | x | x |
| 281 | x | x |
| 282 | x | x |
| 283 | x | x |
| 284 | x | x |
| 285 | x | x |
| 286 | x | x |
| 287 | x | x |
| 288 | x | x |
| 289 | x | x |
| 290 | x | x |
| 291 | ○ | ○ |
| 292 | ○ | ○ |
| 293 | ○ | ○ |
| 294 | ○ | ○ |
| 295 | ○ | ○ |
| 296 | ○ | ○ |
| 297 | ○ | ○ |
| 298 | ○ | ○ |
| 299 | ○ | ○ |

TABLE 20-continued

| Sample | Judgement | |
|---|---|---|
| | Connection reliability | Sensor output |
| 300 | ○ | ○ |
| 301 | ○ | ○ |
| 302 | ○ | ○ |
| 303 | ○ | ○ |
| 304 | ○ | ○ |
| 305 | ○ | ○ |
| 306 | ○ | ○ |
| 307 | ○ | ○ |
| 308 | ○ | ○ |
| 309 | ○ | ○ |
| 311 | ○ | ○ |
| 312 | ○ | ○ |
| 313 | ○ | ○ |
| 314 | ○ | ○ |
| 315 | x | x |
| 316 | x | x |
| 317 | x | x |
| 318 | x | x |
| 319 | x | x |
| 320 | x | x |
| 321 | x | x |
| 322 | x | x |
| 323 | x | x |
| 324 | x | x |
| 325 | x | x |
| 326 | x | x |
| 327 | x | x |
| 328 | x | x |
| 329 | x | x |
| 330 | x | x |
| 331 | x | x |
| 332 | x | x |

Table 19 and Table 20 indicate that samples having the following ranges have favorable connection reliability and sensor output: 0.01 mm≤A≤1.315 mm, 0.02 mm≤B2.63 mm, B/A≥2, and 0.01 mm≤d≤0.1 mm.

Next, Sample 333 to Sample 335 were manufactured by changing the Pt/Pd composition (see Table 21) of the first metal material. Other material compositions and structures were the same as those of Sample 269. The electrical resistance between the first sensor electrode 40a and the measured gas side wiring 20, and sensor output were studied for each sample. The results are shown in Table 21. Judgment criteria are the same as those in Example 1 and indicated using ○ and x.

TABLE 21

| Sample | Pt/Pd Composition ratio (wt %) | Judgement | |
|---|---|---|---|
| | | Connection reliability | Sensor output |
| 333 | 90/10 | ○ | ○ |
| 334 | 50/50 | ○ | ○ |
| 335 | 10/90 | ○ | ○ |

Table 21 indicates that even when the Pt/Pd composition ratio of the first metal material is changed between 90/10 and 10/90, connection reliability between the first sensor electrode 40a and the measured gas side wiring 20, and sensor output in Sample 333 to Sample 335 are favorable.

Eighteenth Embodiment

FIG. 35

According to an eighteenth embodiment, the connection structure and the materials of the electrode terminal 4 and the wiring layer 2 are changed in the heater section 14 of the gas sensor element 1 according to the first embodiment (FIG. 5).

Figure 35:
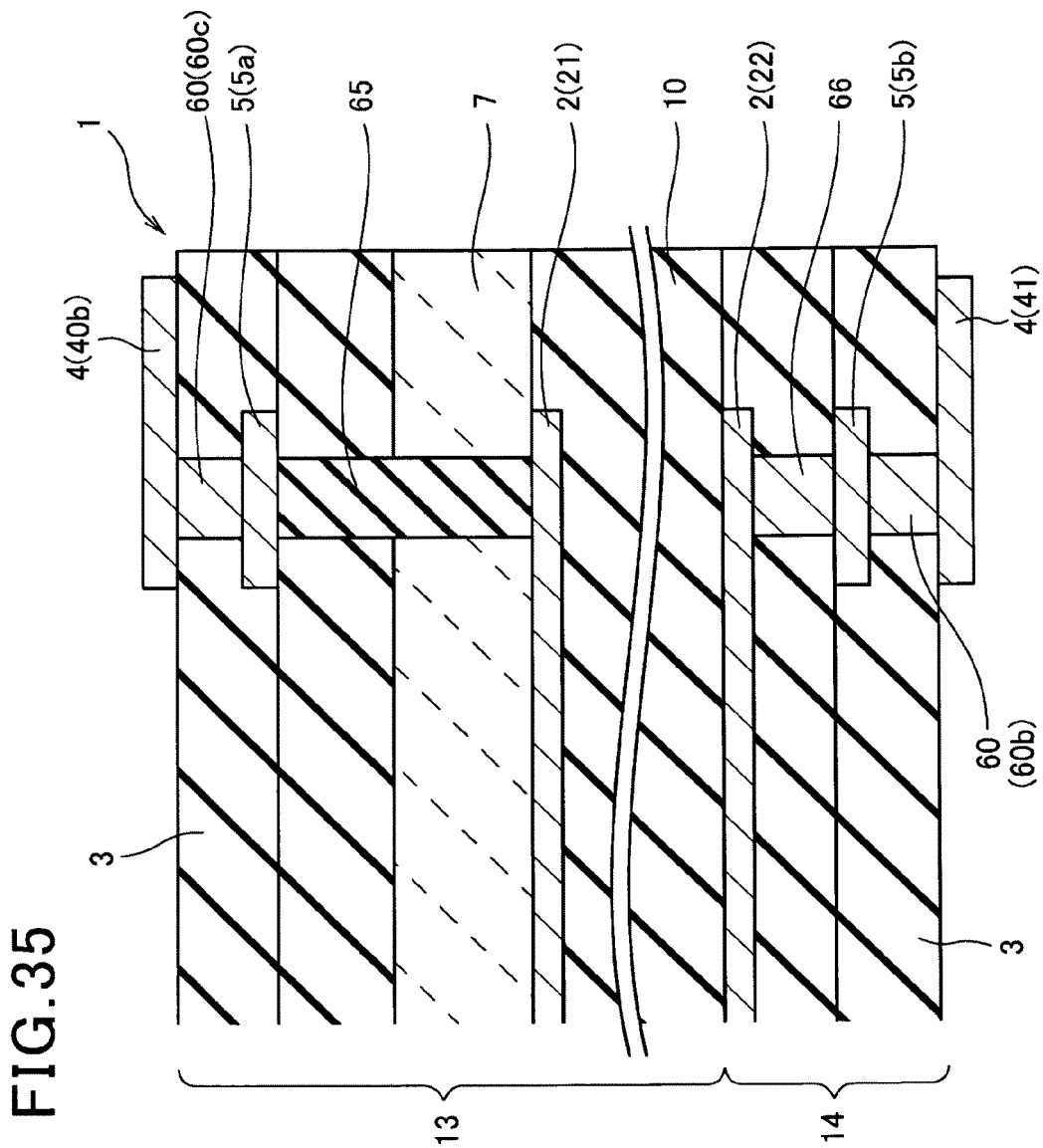
FIG. 35 is a cross-sectional view of a gas sensor element passing through a second sensor electrode 40*b* before firing according to a eighteenth embodiment of the present invention.

As shown in FIG. 35, the sensor section 13 has the same configuration and uses the same material as the sensor section 13 of the gas sensor element 1 shown in FIG. 5.

The heater section 14 has the same configuration and uses the same material as the heater section 14 of the gas sensor element 1 according to the first embodiment (FIG. 4).

The connection structure of the first sensor electrode 40a and the measured gas side wiring 20 (not shown) is similar to the structure of the sensor section 13 according to the above-described fourth embodiment (FIG. 30).

Other configurations are similar to those according to the first embodiment and, therefore, descriptions thereof are omitted.

According to the eighteenth embodiment, operational effects similar to those according to the first embodiment can be achieved.

Nineteenth Embodiment

FIG. 36

According to a nineteenth embodiment, the connection structure and the materials of the electrode terminal 4 and the wiring layer 2 are changed in the heater section 14 of the gas sensor element 1 according to the first embodiment (FIG. 5).

As shown in FIG. 36, the sensor section 13 has the same configuration and uses the same material as the sensor section 13 of the gas sensor element 1 shown in FIG. 5.

The heater section 14 has the same configuration and uses the same material as the heater section 14 of the gas sensor element 1 according to the twelfth embodiment (FIG. 27).

The connection structure of the first sensor electrode 40a and the measured gas side wiring 20 (not shown) is similar to that of the sensor section 13 according to the above-described tenth embodiment.

Other configurations are similar to those according to the first embodiment and, therefore, descriptions thereof are omitted.

According to the nineteenth embodiment, operational effects similar to those according to the first embodiment can be achieved.

Twentieth Embodiment

FIG. 37

According to a twentieth embodiment, the connection structure of the electrode terminal 4 and the wiring layer 2 is the same as that of the gas sensor element 1 according to the second embodiment (FIG. 17). The material of the heater section 14 is changed.

Specifically, as shown in FIG. 37, the difference with the heater section 14 of the gas sensor element 1 shown in FIG. 17 is that the heater wiring 22 and the intermediate layer 5b in the heater section 14 are composed of the first metal material.

The connection structure of the first sensor electrode 40a and the measured gas side wiring 20 (not shown) is similar to the structure of the sensor section 13 according to the twelfth embodiment (FIG. 27).

Other configurations are similar to those according to the first embodiment and, therefore, descriptions thereof are omitted.

According to the twentieth embodiment, operational effects similar to those according to the first embodiment can be achieved.

What is claimed is:

1. A gas sensor element that detects concentration of a specific gas within a measured gas, the gas sensor element comprising:
a wiring layer formed inside the gas sensor element;
an insulating layer covering a front surface of the wiring layer;
an electrode terminal provided on a main surface of the insulating layer on an opposite side of the insulating layer to the wiring layer, and electrically connected to the wiring layer;
an intermediate layer interposed between the electrode terminal and the wiring layer, and electrically connecting the electrode terminal and the wiring layer; and
a metal connecting member having electrical conductivity,
wherein the insulating layer is provided with a through hole formed to pass through the insulating layer, the metal connecting member is disposed within the through hole, the through hole has a smaller outer diameter than that of the intermediate layer, and the metal connecting member electrically connects the intermediate layer and the electrode terminal, wherein
the connecting member and the electrode terminal are composed of a first metal material, the wiring layer and the intermediate layer are composed of a second metal material, and the second metal material is lower in melting point than the first metal material.

2. The gas sensor element according to claim 1, wherein a void is formed in the peripheral portion of the intermediate layer that is the periphery of an interface with the intermediate layer that is in contact with the connecting member composed of a metal material differing from that of the intermediate layer.

3. The gas sensor element according to claim 1, wherein a relationship B/A≥2 is established between an outer diameter A of the through hole and an outer diameter B of the intermediate layer, and a thickness d of the intermediate layer is 0.01 mm or more.

4. A gas sensor including a gas sensor element according to claim 3.

5. A gas sensor element that detects concentration of a specific gas within a measured gas, the gas sensor element comprising:
a wiring layer formed inside the gas sensor element;
an insulating layer covering a front surface of the wiring layer;
an electrode terminal provided on a main surface of the insulating layer on an opposite side of the insulating layer to the wiring layer, and electrically connected to the wiring layer;
an intermediate layer interposed between the electrode terminal and the wiring layer, and electrically connecting the electrode terminal and the wiring layer;
a first through hole that passes through the insulating layer, has a metal first connecting member disposed within, has a smaller outer diameter than the intermediate layer, and connects the intermediate layer and the electrode terminal; and
a second through hole that passes through the insulating layer, has a metal second connecting member disposed within, has a smaller outer diameter than the intermediate layer, and connects the wiring layer and the intermediate layer, wherein
the first connecting member and the electrode terminal are composed of a first metal material, the wiring layer and the second connecting member are composed of a second metal material, and the intermediate layer is composed of whichever of the first metal material and the second metal material has the lower melting point.

6. The gas sensor element according to claim 5, wherein a void is formed in the peripheral portion of the intermediate layer that is the periphery of an interface with the intermediate layer that is in contact with the connecting member composed of whichever of the first metal material and the second metal material has the higher melting point.

7. The gas sensor element according to claim 5, wherein a void is formed in the peripheral portion of the intermediate layer that is the periphery of an interlace with the intermediate layer that is in contact with the connecting member composed of whichever of the first metal material and the second metal material has the higher melting point,
wherein
a relationship B/A≥2 is established between an outer diameter A of the first through hole and an outer diameter B of the intermediate layer,
a relationship B/A≥2 is established between an outer diameter A of the second through hole and an outer diameter B of the intermediate layer,
and a thickness d of the intermediate layer is 0.01 mm or more.

8. A gas sensor including a gas sensor element according to claim 7.

9. The gas sensor element according to claim 5, wherein a void is formed in the peripheral portion of the intermediate layer that is the periphery of an interface with the intermediate layer that is in contact with the connecting member composed of a metal material differing from that of the intermediate layer.

10. The gas sensor element according to claim 5, wherein a relationship B/A≥2 is established between an outer diameter A of the through hole and an outer diameter B of the intermediate layer, and a thickness d of the intermediate layer is 0.01 mm or more.

* * * * *